US011975079B2

(12) United States Patent
Chen et al.

(10) Patent No.: US 11,975,079 B2
(45) Date of Patent: May 7, 2024

(54) TRUNCATED EVANS BLUE MODIFIED FIBROBLAST ACTIVATION PROTEIN INHIBITOR, PREPARATION METHOD AND APPLICATION THEREOF

(71) Applicant: YANTAI LANNACHENG BIOTECHNOLOGY CO., LTD., Shandong (CN)

(72) Inventors: Xiaoyuan Chen, Shandong (CN); Pengfei Xu, Shandong (CN); Zhide Guo, Shandong (CN); Xiaoming Wu, Shandong (CN); Qingbao Yang, Shandong (CN); Tian He, Shandong (CN)

(73) Assignee: YANTAI LANNACHENG BIOTECHNOLOGY CO., LTD., Shengdong (CN)

( * ) Notice: Subject to any disclaimer, the term of this patent is extended or adjusted under 35 U.S.C. 154(b) by 0 days.

(21) Appl. No.: 18/257,063

(22) PCT Filed: Jul. 11, 2021

(86) PCT No.: PCT/CN2021/105637

§ 371 (c)(1),
(2) Date: Jun. 12, 2023

(87) PCT Pub. No.: WO2022/170732

PCT Pub. Date: Aug. 18, 2022

(65) Prior Publication Data

US 2023/0390421 A1 Dec. 7, 2023

(30) Foreign Application Priority Data

Feb. 10, 2021 (CN) ......................... 202110182478.0
Jul. 3, 2021 (CN) ......................... 202110753794.9

(51) Int. Cl.
*A61K 51/00* (2006.01)
*A61K 9/00* (2006.01)
(Continued)

(52) U.S. Cl.
CPC ........ *A61K 51/0482* (2013.01); *A61K 9/0019* (2013.01); *C07D 401/14* (2013.01); *A61K 2123/00* (2013.01)

(58) Field of Classification Search
CPC .............. A61K 51/0482; A61K 9/0019; A61K 2123/00; C07D 401/14
See application file for complete search history.

(56) References Cited

U.S. PATENT DOCUMENTS

2016/0287730 A1 10/2016 Chen et al.

FOREIGN PATENT DOCUMENTS

CN 109153641 A 1/2019
CN 111699181 A 9/2020
(Continued)

OTHER PUBLICATIONS

Chen et al. (J. Nucl. Med. 2017, 58, 590-597).*
Loktev et al. (J. Nucl. Med. 2018, 59, 1423-1429).*
Linder et al. (J. Nucl. Med. 2018, 59, 1414-1422).*
International Search Report (with English translation) and Written Opinion issued in PCT/CN2021/105637, dated Mar. 30, 2022, 34 pages provided.
(Continued)

*Primary Examiner* — Michael G. Hartley
*Assistant Examiner* — Melissa J Perreira
(74) *Attorney, Agent, or Firm* — HSML P.C.

(57) ABSTRACT

The present disclosure provides a truncated Evans Blue modified fibroblast activation protein inhibitor compound. The compound is formed by connecting truncated Evans Blue, a fibroblast activation protein inhibitor and a nuclide chelating group by means of connecting groups $L_1$, $L_2$, $L_3$, $L_4$ and X. The compound has the following structure shown in Formula (I), where $R_1$ is a fibroblast activation protein inhibitor; $L_1$ is lysine, glutamic acid, or a derivative structure thereof; $L_2$ is $-(CH_2)_n-$, n is an integer from 0 to 30, and each $-CH_2-$ may be individually substituted or unsubstituted with $-O-$, $-NH-$, $-(CO)-$, $-NH(CO)-$, or $-(CO)-NH-$; $L_3$ is $-(CH_2)_m-$, m is an integer from 0 to 30, and each $-CH_2-$ may be individually substituted or unsubstituted with $-O-$ or $-(CO)-$; $L_4$ is $-(CH_2)_p-$, p is an integer from 0 to 30, and each $-CH_2-$ may be individually substituted or unsubstituted with $-O-$, $-NH-$, $-(CO)-$, $-NH(CO)-$, or $-(CO)-NH-$; X is selected from N, C, O, S, or

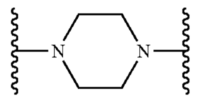

, 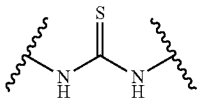 ,

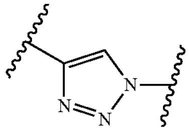

, and 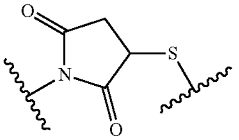 ;

and $R_2$ is a nuclide chelating group. The present disclosure also provides a radiolabeled complex based on the structure of the compound. The compound and the radiolabeled complex have the characteristics of significantly prolonging the half-life in blood circulation, improving the uptake and enrichment in tumors and prolonging the retention time, and are suitable for nuclide therapy and imaging of tumors with high expression of FAP.

Formula (I)

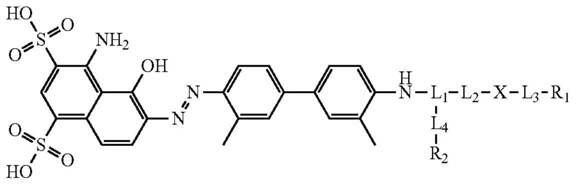

8 Claims, 12 Drawing Sheets

(51) Int. Cl.

*A61K 51/04* (2006.01)
*A61M 36/14* (2006.01)
*C07D 401/14* (2006.01)

(56) References Cited

FOREIGN PATENT DOCUMENTS

| | | | |
|---|---|---|---|
| CN | 113004371 | A | 6/2021 |
| WO | 2020160222 | A2 | 8/2020 |
| WO | 2021005125 | A1 | 1/2021 |

OTHER PUBLICATIONS

Kelly James M.et al.,“A Trifunctional Theranostic Ligand Targeting Fibroblast Activation Protein-α (FAPα),”, Molecular Imaging and Biology,vol. 23, Mar. 15, 2021, pp. 686-696; Cited in ISR.

Lau Joseph et al., “Bench to Bedside: Albumin Binders for Improved Cancer Radioligand Therapies,”, BC Bioconjugate Chemistry, vol. 30, Jan. 8, 2019, pp. 487-502; Cited in ISR.

Jacobson Orit et al., “Albumin-Binding Evans Blue Derivatives for Diagnostic Imaging and Production of Long-Acting Therapeutics,”, BC Bioconjugate Chemistry, vol. 27, Sep. 28, 2016, pp. 2239-2247; Cited in ISR.

Office Action issued in CN202110182478.0, dated Jun. 28, 2022, with English translation.

Notice of Allowance issued in CN202110182478.0, dated Jan. 11, 2023, with English translation.

* cited by examiner

TRUNCATED EVANS BLUE MODIFIED FIBROBLAST ACTIVATION PROTEIN INHIBITOR, PREPARATION METHOD AND APPLICATION THEREOF

TECHNICAL FIELD

The present disclosure relates to the fields of nuclear medicine and molecular imaging, and specifically relates to a truncated Evans Blue modified fibroblast activation protein inhibitor, preparation and labelling thereof and application thereof.

BACKGROUND

A fibroblast activation protein (FAP) is a membrane serine peptidase that is expressed on the surface of a tumor stroma activated fibroblast and plays an important role in generation and development processes of tumors. Previous studies show that the FAP is generally not expressed in normal human tissues, but selectively highly expressed on surfaces of stromal fibroblasts of more than 90% of epithelial malignant tumors, including breast cancer, ovarian cancer, lung cancer, colorectal cancer, gastric cancer and pancreatic cancer. In view of widespread expression and important role in tumors, the FAP has become an important target for imaging and therapy of tumors.

At present, a radionuclide labeled fibroblast activation protein inhibitor (FAPI), represented by a quinolinic acid derivative, has made important progress in the field of accurate imaging of tumors. For example, PET/CT imaging agents such as PHEAPI-02 and PHEAPi-04 have realized specific imaging of more than 30 different types of tumors. Compared with FDG imaging, FAPI imaging has lower background in brain, liver and oropharyngeal mucosa and higher detection rate of tumor lesions. According to current reports, the FAPI is rapidly cleared in blood circulation and rapidly eluted at a tumor site. Such metabolic characteristics are favorable for imaging because clean background can be provided. However, the metabolic characteristics are unfavorable for therapy because rapid metabolism and elution lead to low effective dose and short retention time at a tumor site, high dose or a more frequent administration method is required to meet therapeutic needs, and the possibility of adverse reactions is increased.

For example, FAPI-02 is completely cleared in blood circulation within one hour, and 24 hours later, the retained dose at a tumor site is decreased by about 75%. Although a non-pharmacophore part of the structure of the FAPI has been optimized in recent research work, the dose uptake of the FAPI in tumors and the retention time are improved to an extremely limited extent, and the needs of therapeutic use cannot be met. Persons of ordinary skill in the field know that when a small molecule medicine has too short circulation time in blood vessels or is quickly cleared by the body, binding of the medicine to a target will be insufficient. Therefore, during preparation of an FAPI probe, it is possible to increase the dose uptake and prolong the retention time of the probe at a target site when the half-life of the probe in blood circulation is properly prolonged.

Therefore, a new strategy is required to prolong the half-life of the FAPI probe in blood circulation, so that the FAPI probe can have appropriate metabolic dynamics, higher dose uptake in tumors and longer retention time in tumors to meet requirements of nuclide therapy and imaging.

SUMMARY

Based on the above background, a primary purpose of the present disclosure is to develop a kind of conjugates of truncated Evans Blue (tEB) and a fibroblast activation protein inhibitor (FAPI). The conjugate is characterized in that through effective binding of the truncated Evans Blue to serum albumin, the albumin is used as a delivery carrier of the FAPI, so that the half-life of the FAPI in peripheral blood is prolonged, the uptake and accumulation in tumors are increased, and the retention time is prolonged. According to the tEB-FAPI conjugates developed by the present disclosure, the defects of too fast metabolism of the small molecule FAPI and too short retention time in a target organ can be overcome, nuclide therapy and imaging effects of targeting FAP are improved, and the potential for clinical application and popularization is achieved.

Another purpose of the present disclosure is to provide a radiolabeled fibroblast activation protein inhibitor modified by truncated Evans Blue (tEB-FAPI) with a long half-life in blood circulation.

Another purpose of the present disclosure is to provide a preparation method of a radiolabeled tEB-FAPI complex.

Another purpose of the present disclosure is to provide application of the complex in nuclide imaging and therapy by targeting FAP tumors.

Technical solutions for realizing the above primary purpose of the present disclosure include the following two aspects: synthesis of ligands and radiolabeling of the ligands.

In a first aspect, the present disclosure provides a truncated Evans Blue (tEB) modified fibroblast activation protein inhibitor (FAPI). The compound has the following structure shown in Formula (I), and is denoted as "tEB-FAPI":

Formula (I)

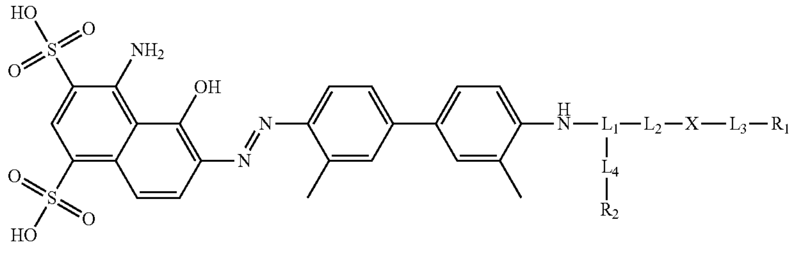

wherein $L_1$ is a lysine or glutamic acid structure, or a derivative compound structure containing a lysine or glutamic acid structure;

$L_2$ is $-(CH_2)_n-$, wherein n is an integer from 0 to 30, wherein each $CH_2$ can be individually substituted or unsubstituted with $-O-$, $-NH-$, $-(CO)-$, $-NH$ (CO)—, or —(CO)—NH—, provided that no two adjacent $CH_2$ groups are substituted;

$L_3$ is $—(CH_2)_m—$, wherein m is an integer from 0 to 30, wherein each $CH_2$ can be individually substituted or unsubstituted with —O— or —(CO)—, provided that no two adjacent $CH_2$ groups are substituted;

$L_4$ is $—(CH_2)_p—$, wherein p is an integer from 0 to 30, wherein each $CH_2$ can be individually substituted or unsubstituted with —O—, —NH—, —(CO)—, —NH(CO)—, or —(CO)—NH—, provided that no two adjacent $CH_2$ groups are substituted;

X is selected from N, C, O, S, or any one of the following structures:

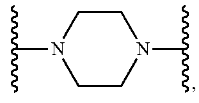,
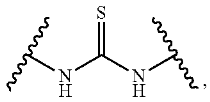,
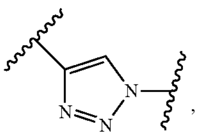, and
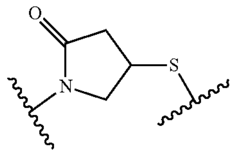;

$R_1$ is the following structure of a fibroblast activation protein inhibitor:

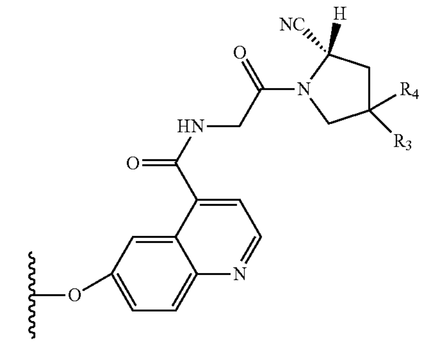

$R_2$ is a nuclide chelating group, and is selected from any one of the following structures:

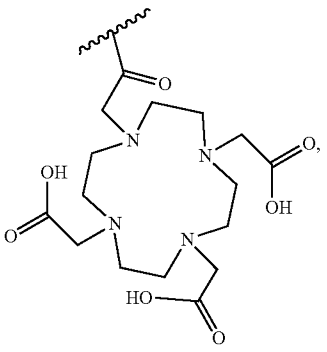,

-continued

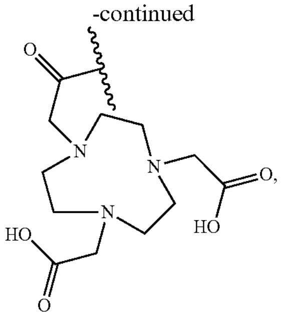,

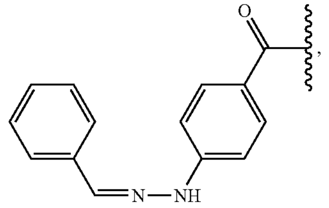, and

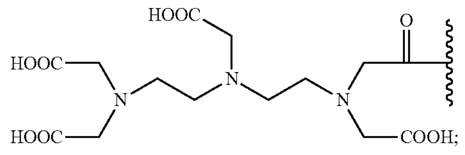;

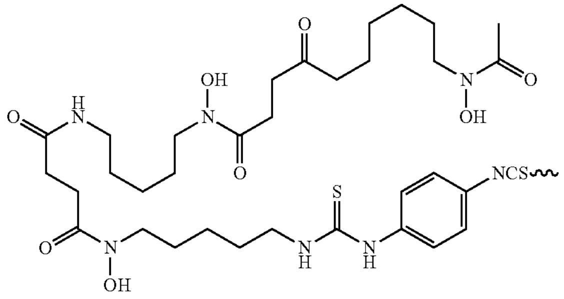

and $R_3$-$R_4$ are the same or different, and are independently selected from H or F.

In a preferred solution of the present disclosure, the $L_2$ in Formula (I) is $—(CH_2)_n—$; n is an integer from 0 to 16, is more preferably an integer from 0 to 12, and is further preferably 0, 3, or 10; and each $—CH_2—$ may be individually substituted or unsubstituted with —O—, —NH—, or —(CO)—, provided that no two adjacent $—CH_2—$ groups are substituted.

In a preferred solution of the present disclosure, the $L_3$ in Formula (I) is $—(CH_2)_m—$; m is an integer from 0 to 20, is more preferably an integer from 1 to 6, and is further preferably 2 or 3; and each $—CH_2—$ may be individually substituted or unsubstituted with —O—, provided that no two adjacent $—CH_2—$ groups are substituted.

In a preferred solution of the present disclosure, the $L_4$ in Formula (I) is $—(CH_2)_p—$; p is an integer from 0 to 20, is more preferably an integer from 0 to 12, is further preferably 3, 4, 9, or 12, and is most preferably 3; and each $—CH_2—$ may be individually substituted or unsubstituted with —O—, —NH—, —(CO)—, —NH(CO)—, or —(CO)—NH—, provided that no two adjacent $—CH_2—$ groups are substituted.

In a preferred embodiment of the present disclosure, the X in Formula (I) is

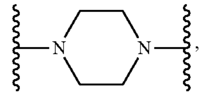 [SMILES: *N1CCN(*)CC1]

the $L_3$ is $-(CH_2)_3-$, the $L_4$ is $-(CH_2)_0-$, and the $R_2$ is DOTA. That is to say, a preferred compound tEB-FAPI of the present disclosure has the following structure shown in Formula II:

Formula (II)

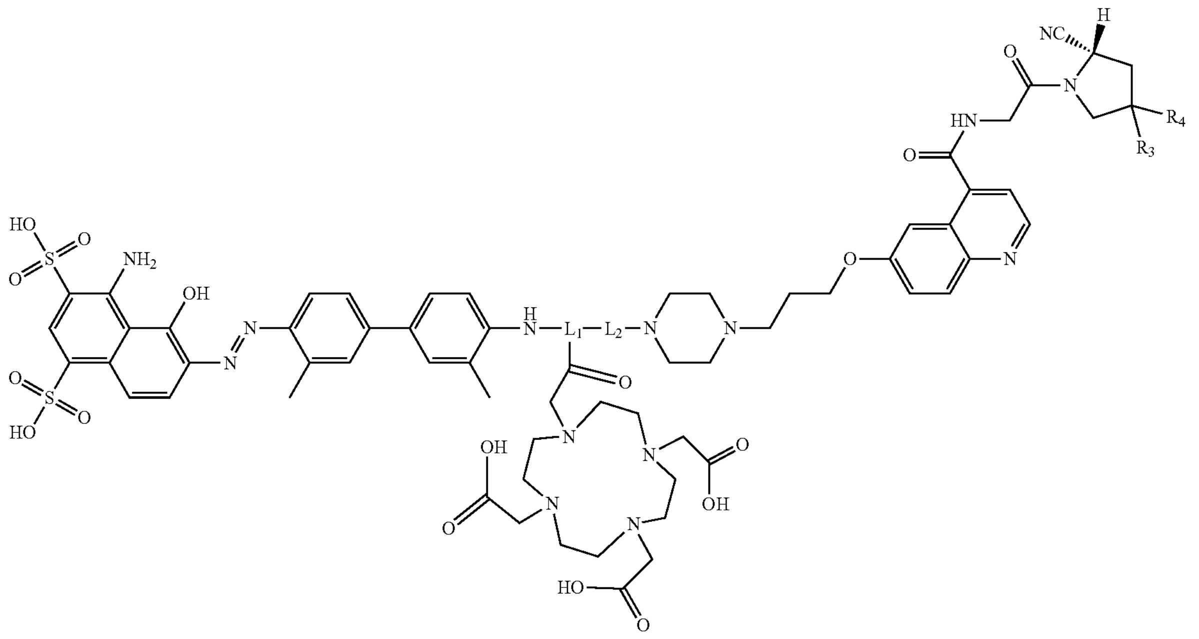

wherein $R_3$ and $R_4$ are both H or both F, $L_1$ is a glutamic acid or lysine structure, and $L_2$ is $-(CH_2)_0$, $-NH-CH_2-(CO)-$, $-NH-CH_2-(CH_2OCH_2)_2-CH_2-(CO)-$, $-NH-CH_2-(CH_2OCH_2)_4-CH_2(CO)-$, $-(CO)-CH_2-(CO)-$, $-(CO)-(CH_2)_2-(CO)-$, $-(CO)-CH_2-(CH_2OCH_2)_2-CH_2(CO)-$, or $-(CO)-CH_2-(CH_2OCH_2)_4-CH_2(CO)-$.

In a more preferred embodiment of the present disclosure, the X in Formula (I) is

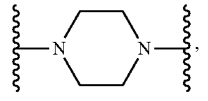 [SMILES: *N1CCN(*)CC1]

the $L_1$ is a glutamic acid structure, the $L_2$ is $-(CH_2)_0-$, $-NH-CH_2-(CO)-$, $-NH-CH_2-(CH_2OCH_2)_2-CH_2-(CO)-$, or $-NH-CH_2-(CH_2OCH_2)_4-CH_2(CO)-$, the $L_3$ is $-(CH_2)_3-$, the $L_4$ is $-(CH_2)_0-$, the $R_2$ is DOTA, and the $R_3$ and $R_4$ are both H or both F.

In another more preferred embodiment of the present disclosure, the X in Formula (I) is

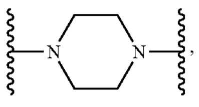

the $L_1$ is a lysine structure, the $L_2$ is $-(CO)-CH_2-(CO)-$, $-(CO)-(CH_2)_2-(CO)-$, $-(CO)-CH_2-(CH_2OCH_2)_2-CH_2(CO)-$, or $-(CO)-CH_2-(CH_2OCH_2)_4-CH_2(CO)-$, the $L_3$ is $-(CH_2)_3-$, the $L_4$ is $-(CH_2)_0-$, the $R_2$ is DOTA, and the $R_3$ and $R_4$ are both H or both F.

In a further preferred solution of the present disclosure, the compound tEB-FAPI has any one of the following structures shown in Formula (II-1) to Formula (II-16):

Formula (II-1)
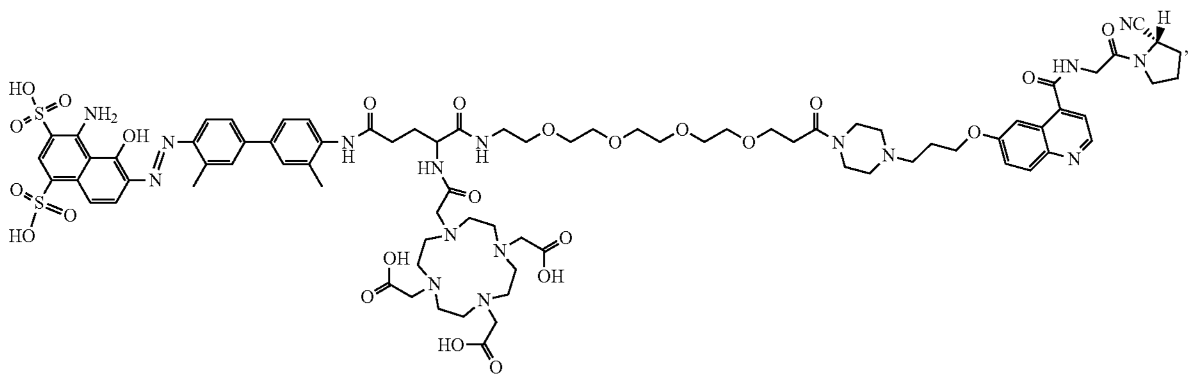
Formula (II-2)
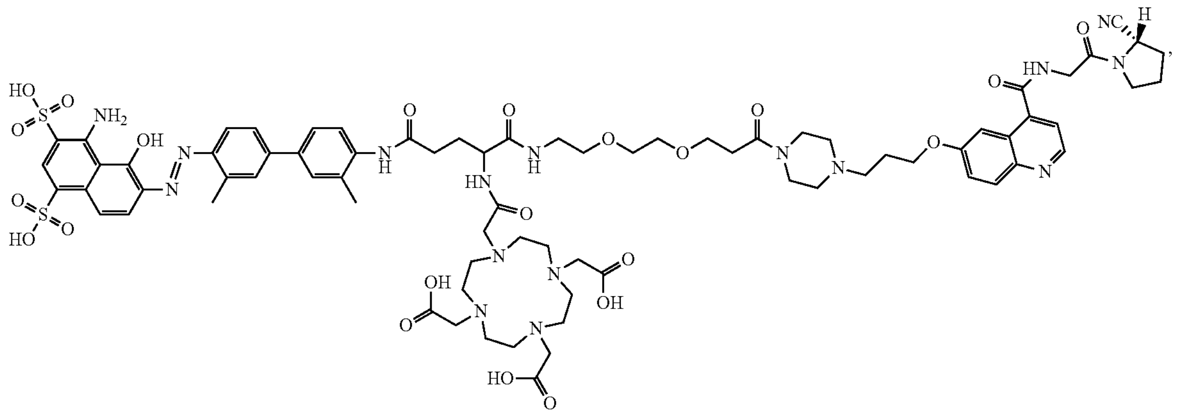
Formula (II-3)
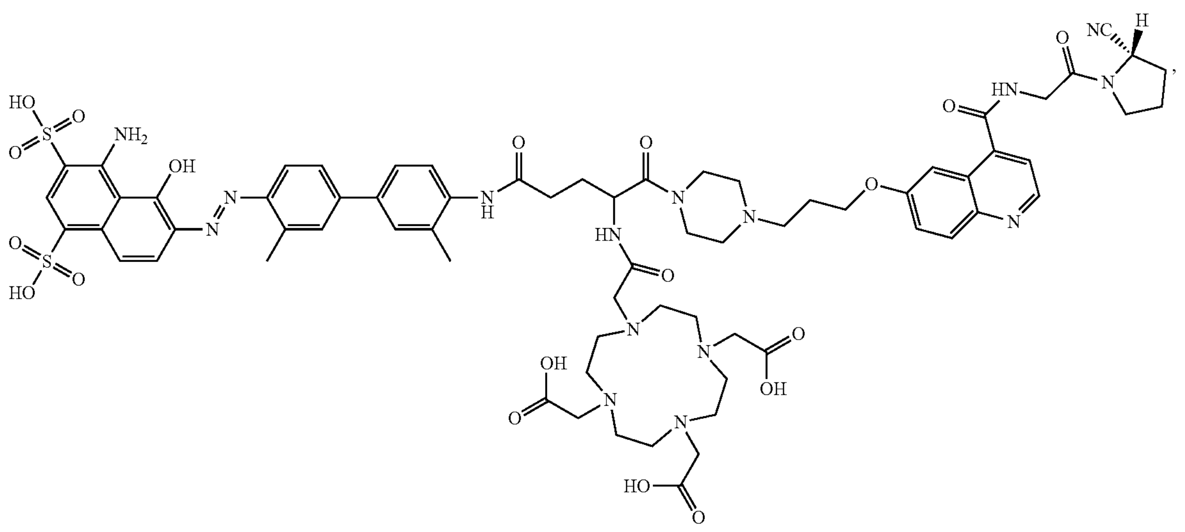

-continued
Formula (II-4)
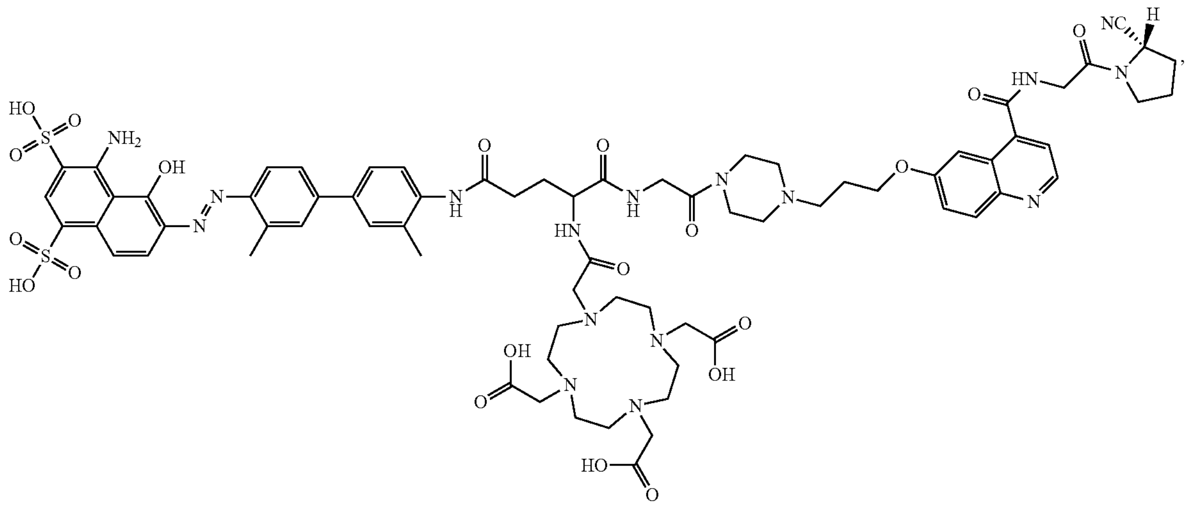
Formula (II-5)
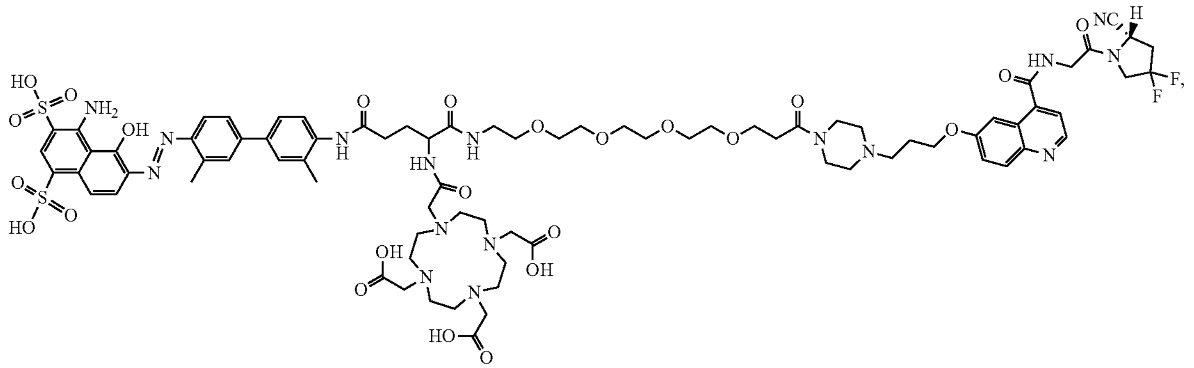
Formula (II-6)
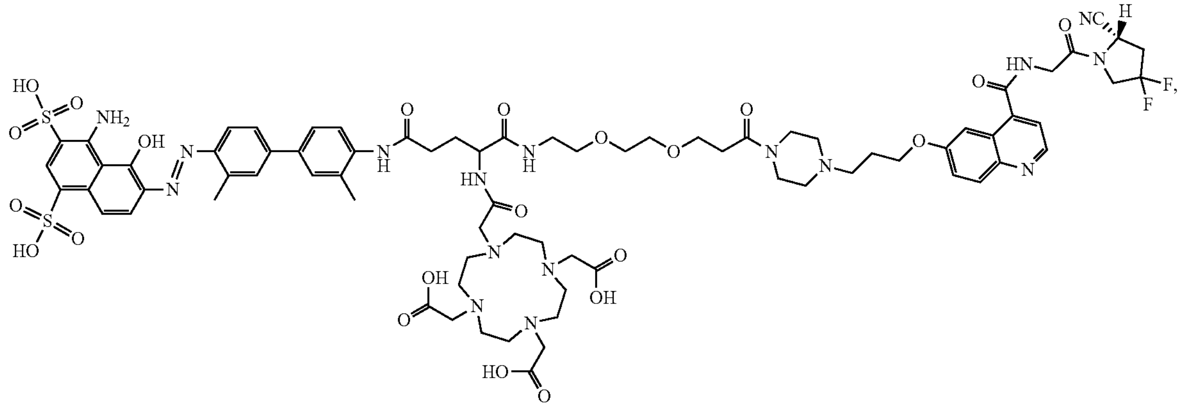

-continued
Formula (II-7)
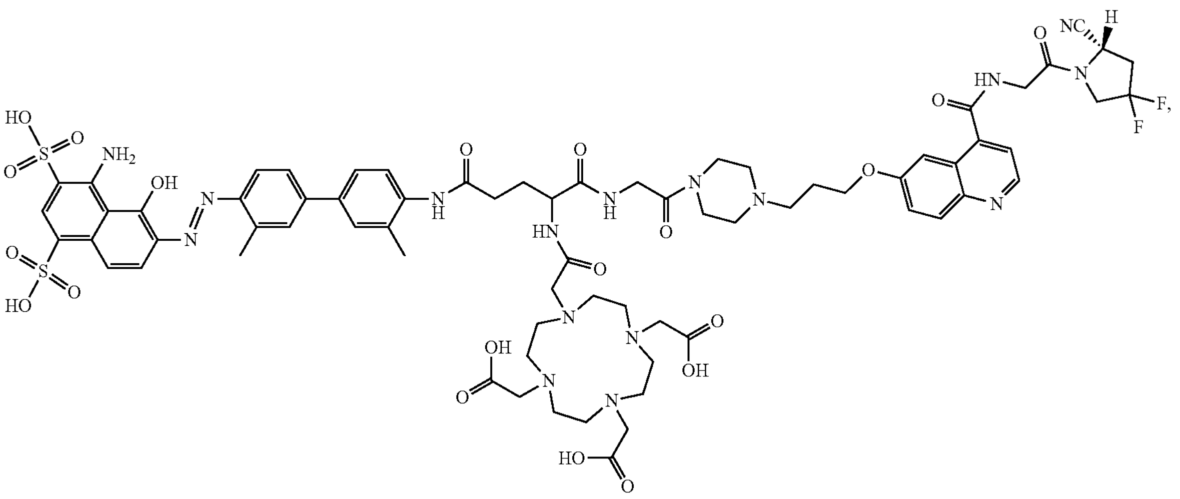
Formula (II-8)
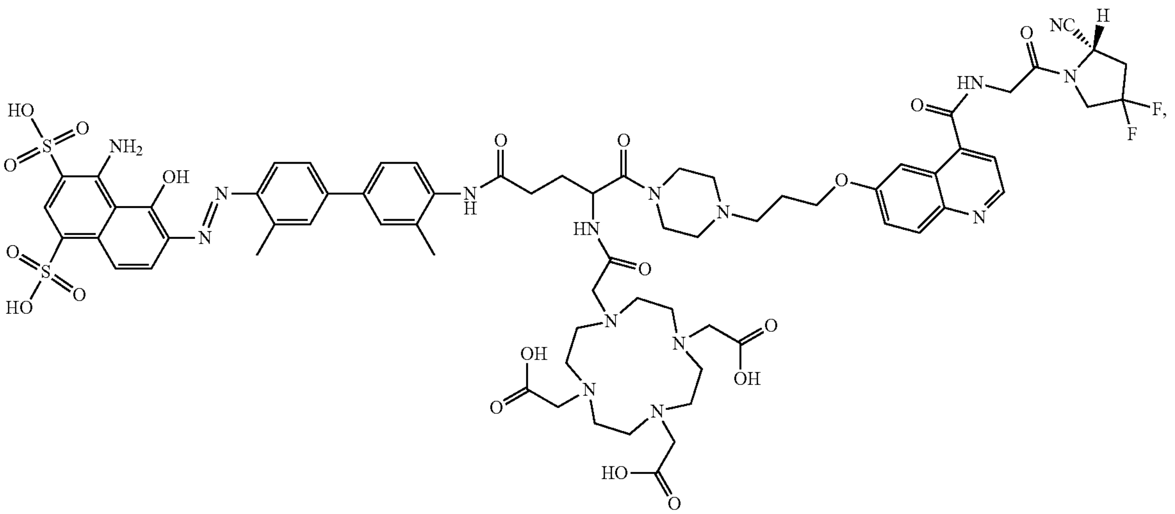
Formula (II-9)
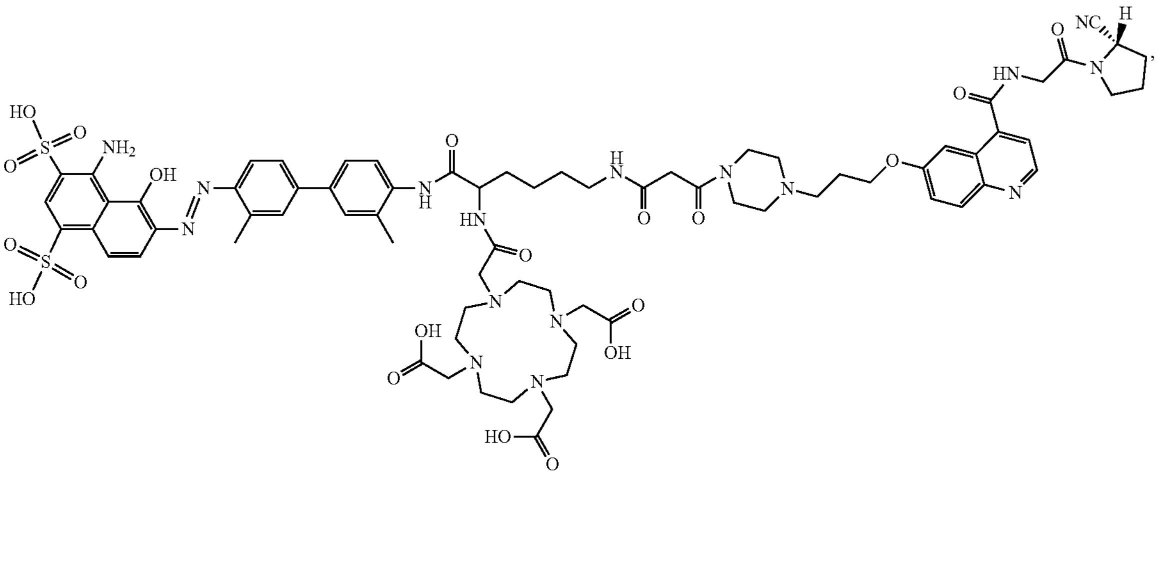

-continued
Formula (II-10)
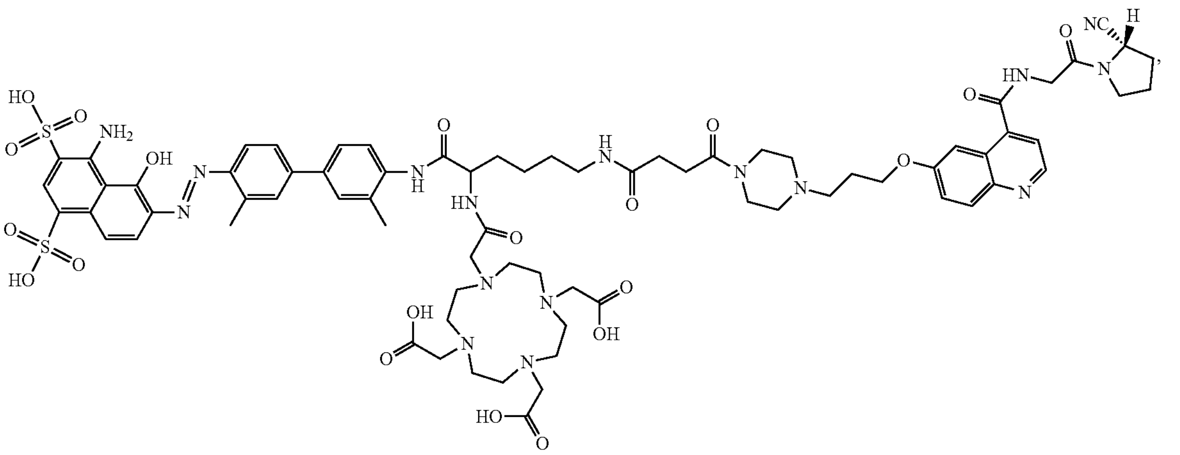
Formula (II-11)
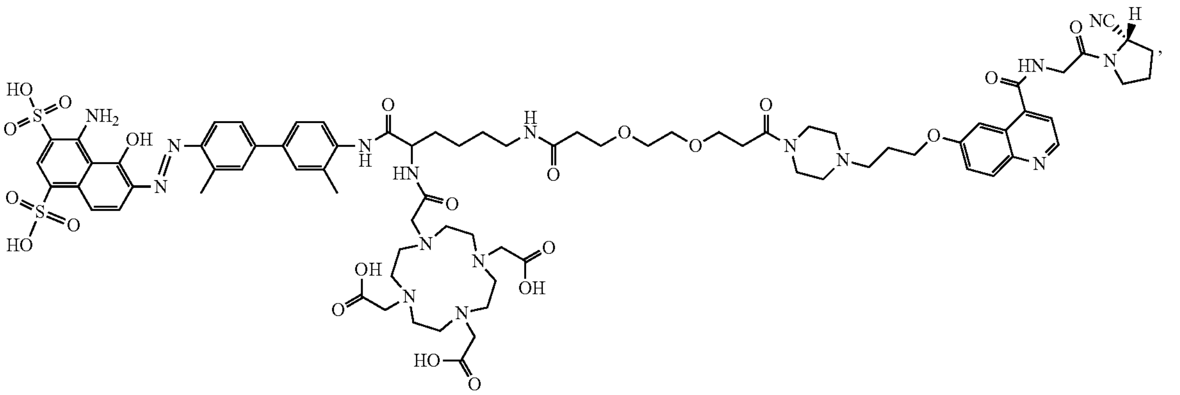
Formula (II-12)
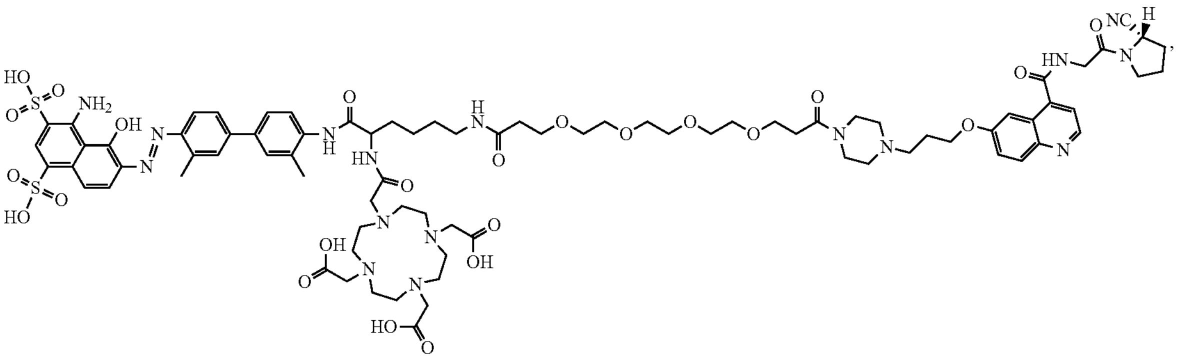

-continued
Formula (II-13)
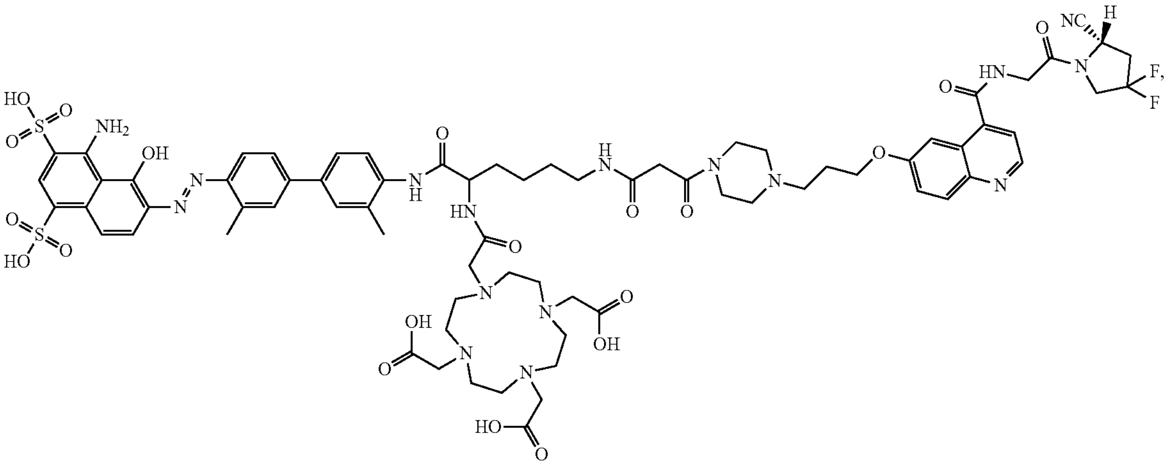
Formula (II-14)
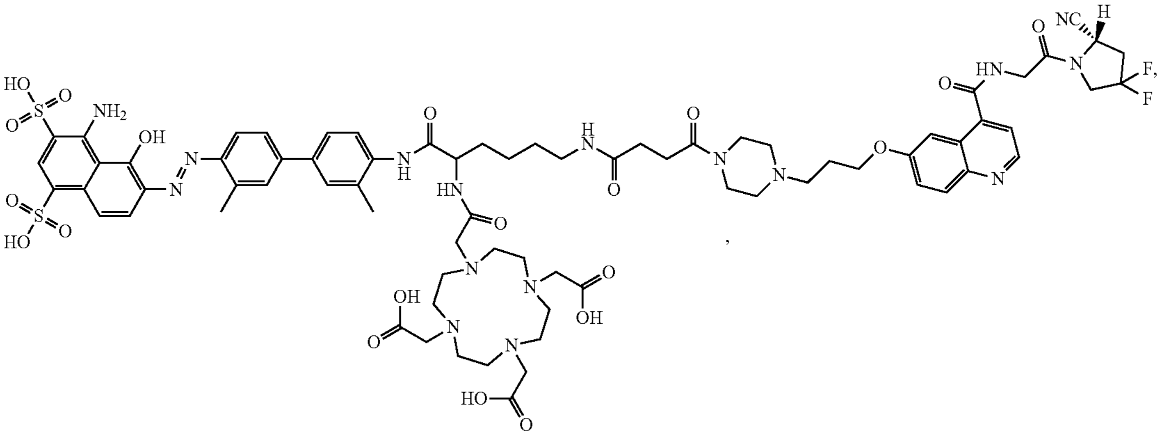
,
Formula (II-15)
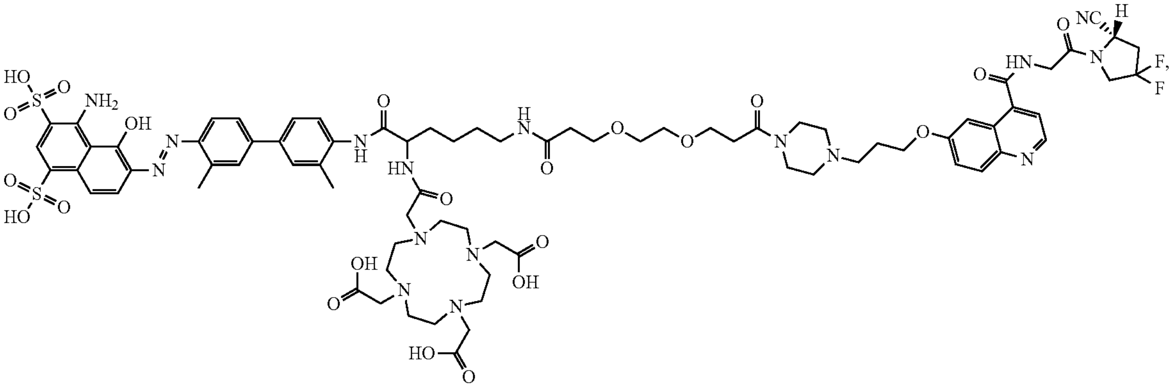
or -continued Formula (II-16)

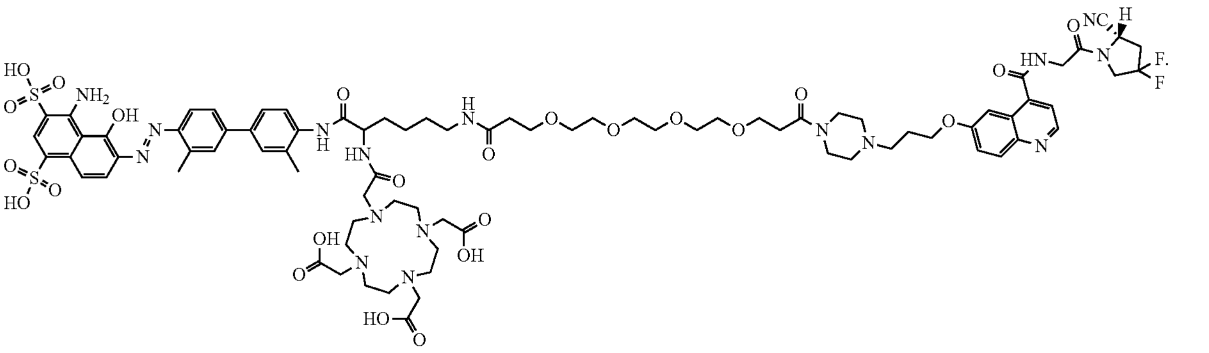

On the above basis, the present disclosure further provides a method for preparing the compound tEB-FAPI shown in Formula (II-1). The method includes the following steps:

① reacting 6-hydroxy-4-quinolinecarboxylic acid with tert-butyl glycinate by amide condensation, followed by reactions with 1-bromo-3-chloropropane and tert-butyl 1-piperazinecarboxylate in sequence; then, removing Boc and tert-butyl protective groups under the action of TFA, and introducing a Boc protective group to amino, followed by an amide condensation reaction with (S)-pyrrolidene-2-carbonitrile hydrochloride; then, removing the Boc protective group using p-toluenesulfonic acid, followed by a condensation reaction with 5,8,11,14-tetraoxa-2-azaheptadecanedioic acid-1-tert-butyl ester; and removing the Boc protective group again under the action of p-toluenesulfonic acid to obtain an intermediate compound A;

② introducing a Boc protective group to one end of 4,4'-diamino-3,3'-dimethyl biphenyl, followed by a reaction with monosodium 1-amino-8-naphthol-2,4-disulfonate to prepare a truncated Evans Blue derivative; removing the Boc protective group, followed by an amide condensation reaction with N-tert-butyloxycarbonyl-L-glutamic acid-1-tert-butyl ester; then, removing Boc and tert-butyl protective groups under the action of TFA; and then carrying out a reaction with di-tert-butyl dicarbonate, and introducing a Boc protective group to amino to obtain an intermediate compound B; and ③ reacting the intermediate compound A with the intermediate compound B by amide condensation; then removing the Boc protective group using p-toluenesulfonic acid; and finally, carrying out a reaction with DOTA-NHS to obtain the compound shown in Formula (II-1).

A preferred method for preparing the compound tEB-FAPI shown in Formula (II-1) of the present disclosure specifically includes the following steps:

dissolving 6-hydroxy-4-quinolinecarboxylic acid (compound 1) and tert-butyl glycinate in N,N-dimethylformamide, and adding HATU to obtain a compound 2; dissolving the compound 2 in N,N-dimethylformamide, adding 1-bromo-3-chloropropane and potassium carbonate, and heating the reaction system to 60° C. for a certain period of time to obtain a compound 3; dissolving the compound 3 in N,N-dimethylformamide, and adding tert-butyl 1-piperazinecarboxylate and potassium iodide for a reaction to obtain a compound 4; dissolving the compound 4 in a trifluoroacetic acid solution for removing protective groups to obtain a compound 5; dissolving the compound 5 in N,N-dimethylformamide, and adding di-tert-butyl dicarbonate and an acid binding agent to obtain a compound 6; the compound 6 reacting with (S)-pyrrolidene-2-carbonitrile hydrochloride under the action of HATU and DIPEA to make a condensation to obtain a compound 7; removing a protective group of the compound 7 under the action of p-toluenesulfonic acid to obtain a compound 8; the compound 8 reacting with 5,8,11,14-tetraoxa-2-azaheptadecanedioic acid-1-tert-butyl ester under the action of HATU and DIPEA to make a condensation to obtain a compound 9; and removing a protective group of the compound 9 under the action of p-toluenesulfonic acid to obtain a compound 10 (namely, the intermediate compound A);

reacting 4,4'-diamino-3,3'-dimethyl biphenyl (compound 11) with di-tert-butyl dicarbonate to obtain a compound 12; reacting the compound 12 with monosodium 1-amino-8-naphthol-2,4-disulfonate and sodium nitrite to prepare a truncated Evans Blue derivative (compound 13); removing a Boc protective group of the compound 13 to obtain a compound 14; reacting the compound 14 with N-tert-butyloxycarbonyl-L-glutamic acid-1-tert-butyl ester under the action of HATU and DIPEA to make a condensation to obtain a compound 15; dissolving the compound 15 in a trifluoroacetic acid solution for removing a protective group to obtain a compound 16; and dissolving the compound 16 in N,N-dimethylformamide, and adding di-tert-butyl dicarbonate and an acid binding agent to obtain a compound 17 (namely, the intermediate compound B); and reacting the compound 17 with the compound 10 under the action of HATU and DIPEA to make a condensation to obtain a compound 18; then removing a protective group of the compound 18 under the action of p-toluenesulfonic acid to obtain a compound 19; and reacting the compound 19 with DOTA-NHS to obtain the final compound 20 shown in Formula (II-1).

A synthesis route in the above specific steps is as follows:

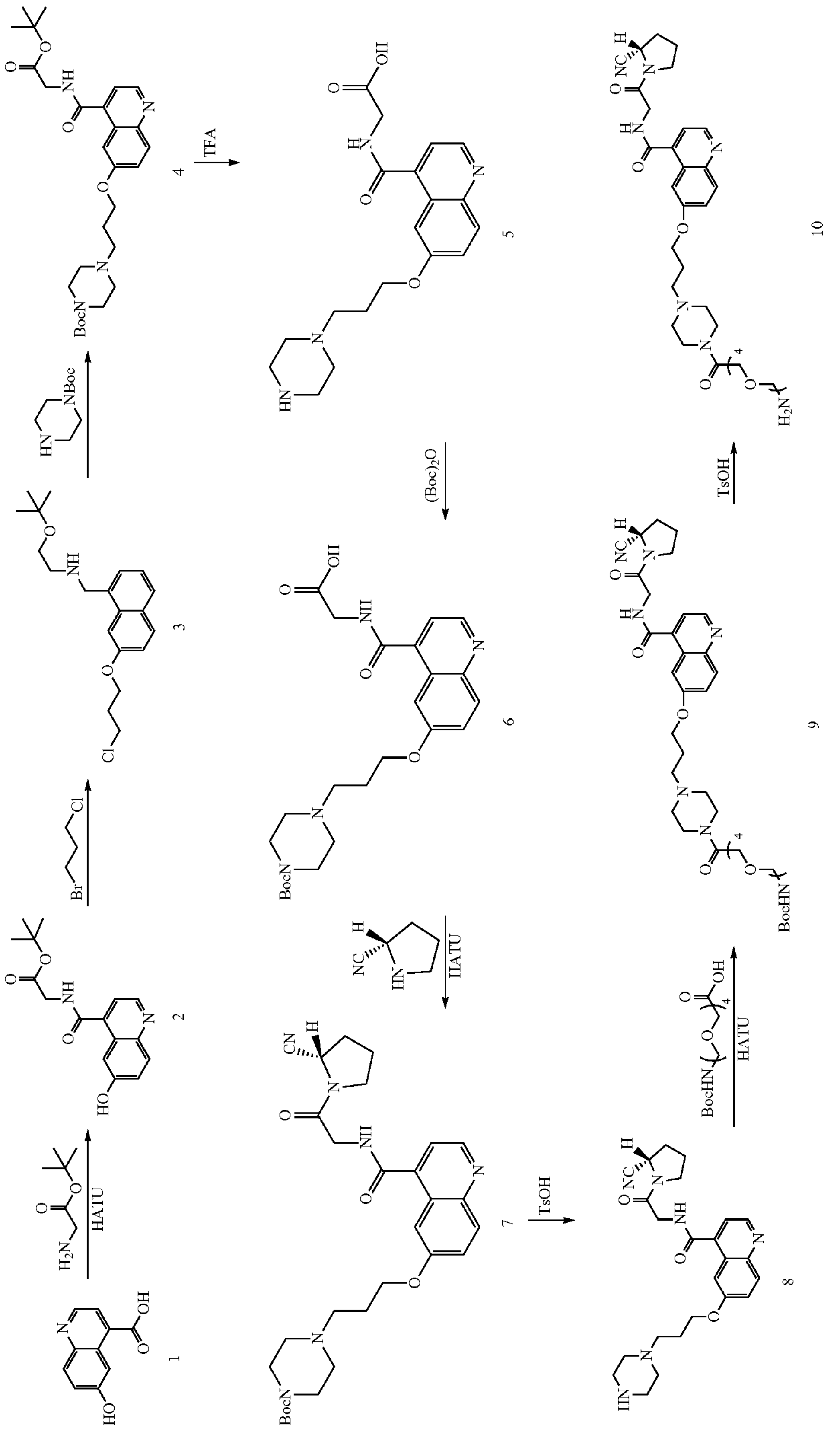
1 2 3 4 5 6 7 8 9 10

-continued
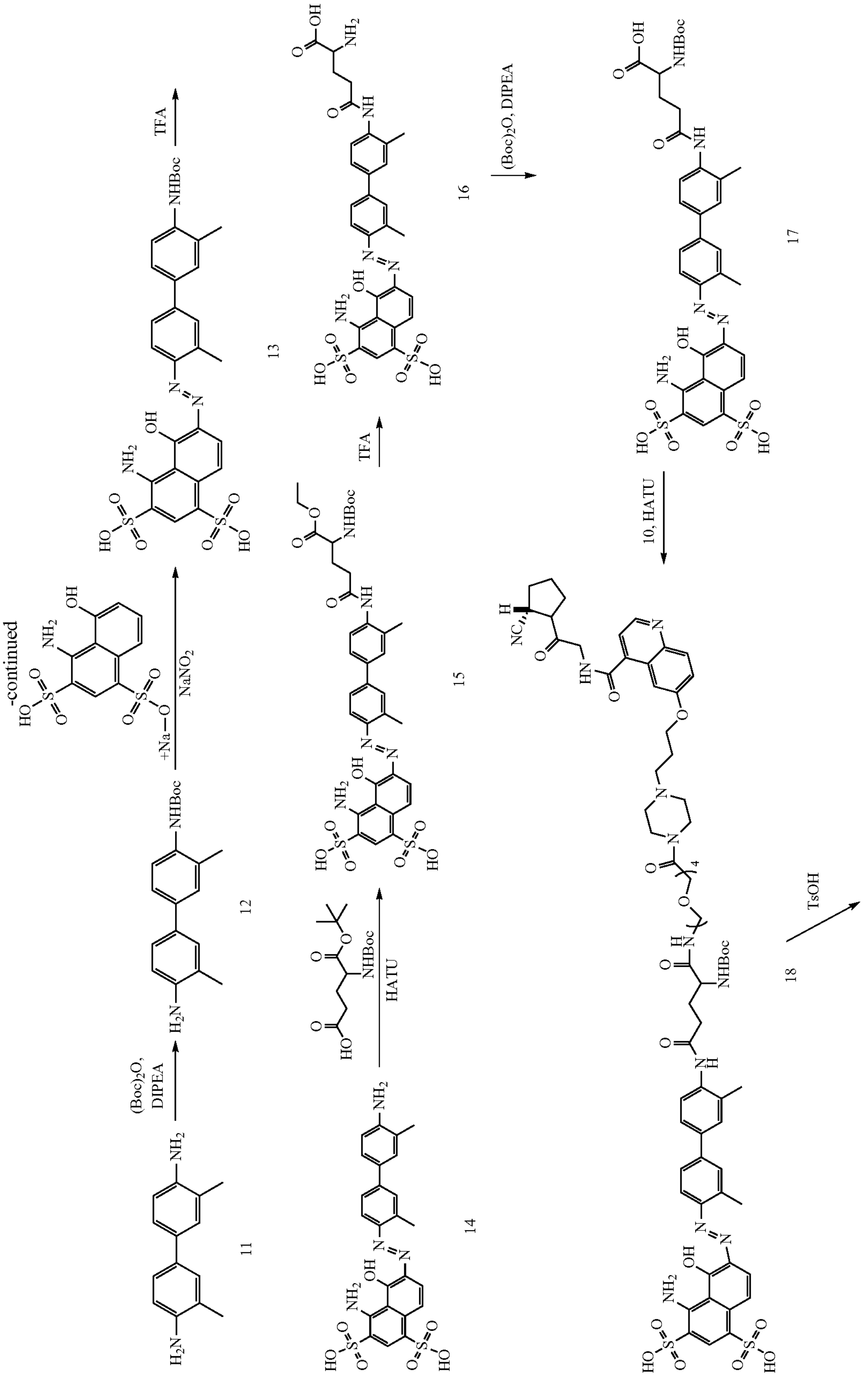
11
12
13
14
15
16
17
18

-continued
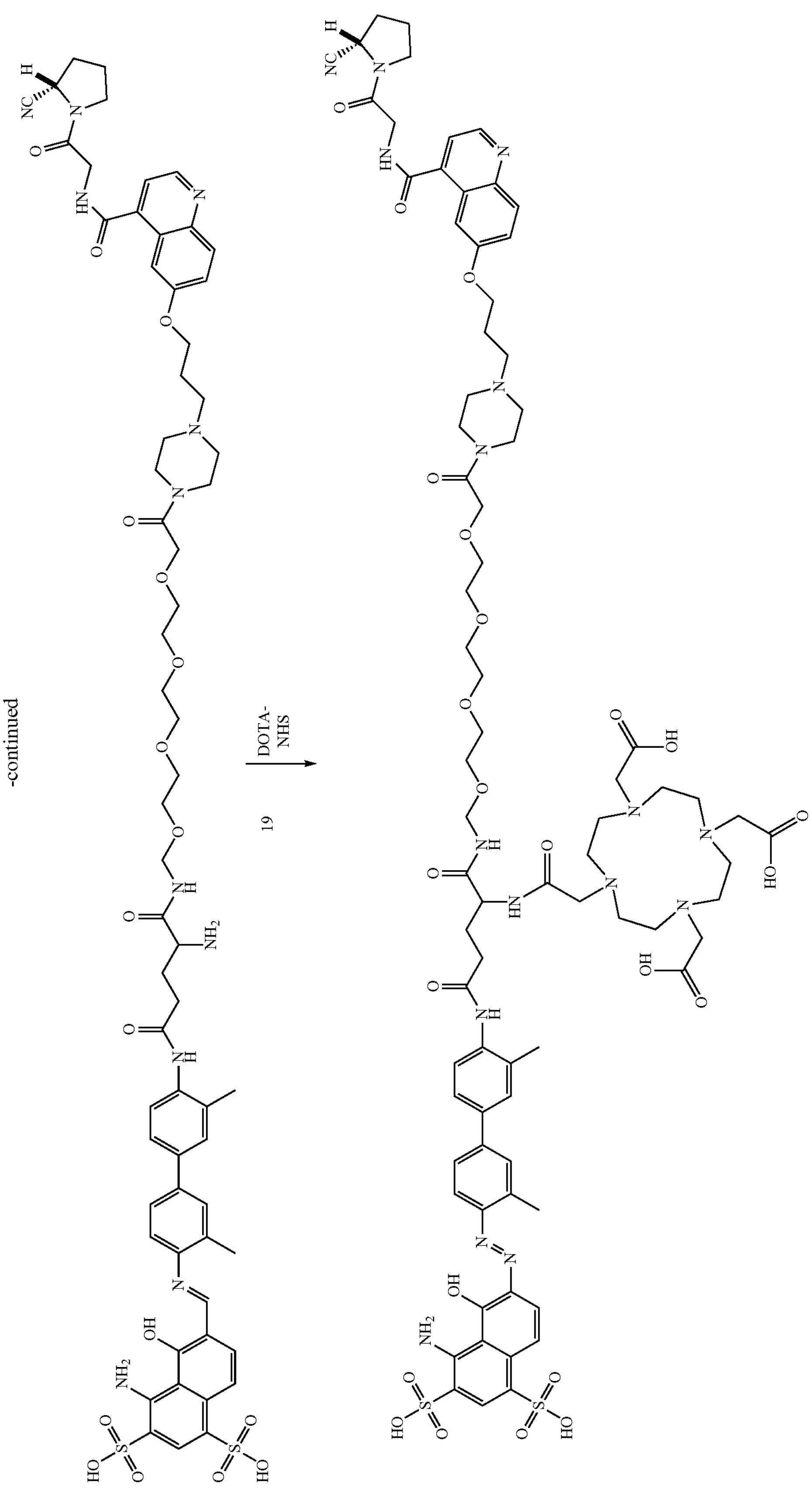
19
20

Preparation methods of other tEB-FAPI compounds in solutions of the present disclosure are similar to the preparation method of the compound 20, and preparation can be carried out basically based on an existing conventional means with reference to the synthesis route of the compound 20.

In another aspect, the present disclosure further provides a radiolabeled tEB-FAPI complex. The complex is obtained by using the compound shown in Formula (I) of the present disclosure as a ligand and labeling the ligand with a radionuclide. The radiolabeled complex can be used as a novel radioactive diagnostic and therapeutic probe for tumors, namely, a radionuclide diagnostic probe or a radionuclide therapeutic probe. The radionuclide may be selected from any one of $^{177}$Lu, $^{90}$Y $^{18}$F, $^{64}$Cu, $^{68}$Ga, $^{62}$Cu, $^{67}$Cu, $^{86}$Y, $^{89}$Zr, $^{99m}$Tc, $^{89}$Sr, $^{153}$Sm, $^{149}$Tb, $^{161}$Tb, $^{186}$Re, $^{188}$Re, $^{212}$Pb, $^{213}$Bi, $^{223}$Ra, $^{225}$Ac, $^{226}$Th, $^{227}$Th, $^{131}$I, $^{211}$At, or $^{111}$In, and is preferably $^{68}$Ga, $^{177}$Lu, or $^{90}$Y.

The complex of the present disclosure preferably has the following structure shown in Formula (IV):

X is selected from N, C, O, S, or the following structures:

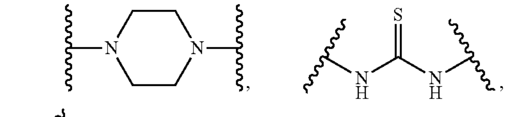

and

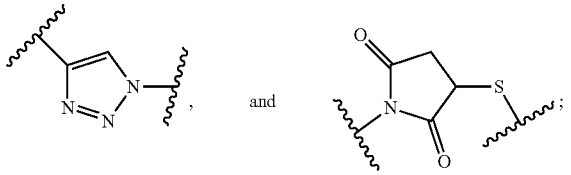

$R_3$ and $R_4$ are the same or different, and are independently selected from H or F;

and M is a radionuclide selected from any one of $^{68}$Ga, $^{177}$Lu, or $^{90}$Y.

In a preferred solution of the complex of the present disclosure, the $L_2$ in Formula (IV) is —$(CH_2)_n$—; n is an integer from 0 to 16, is more preferably an integer from 0 to 12, and is further preferably 0, 3, or 10; wherein each —$CH_2$— may be individually substituted or unsubstituted with —O—, —NH—, or —(CO)—, provided that no two adjacent —$CH_2$— groups are substituted. More preferably, the $L_2$ is —$(CH_2)_0$, —NH—$CH_2$—(CO)—, —NH—$CH_2$—$(CH_2OCH_2)_2$—$CH_2$—(CO)—, —NH—$CH_2$—$(CH_2OCH_2)_4$ —$CH_2$(CO)—, —(CO)—$CH_2$—(CO)—, —(CO)—$(CH_2)_2$—(CO)—, —(CO)—$CH_2$—$(CH_2OCH_2)_2$ —$CH_2$(CO)—, or —(CO)—$CH_2$—$(CH_2OCH_2)_4$—$CH_2$(CO)—.

In a preferred solution of the complex of the present disclosure, the $L_3$ in Formula (IV) is —$(CH_2)_m$—; m is an integer from 0 to 20, is more preferably an integer from 1 to 6, and is further preferably 2 or 3; wherein each —$CH_2$— may be individually substituted or unsubstituted with —O—, provided that no two adjacent —$CH_2$— groups are substituted. More preferably, the $L_3$ is —$(CH_2)_3$—.

Formula (IV)

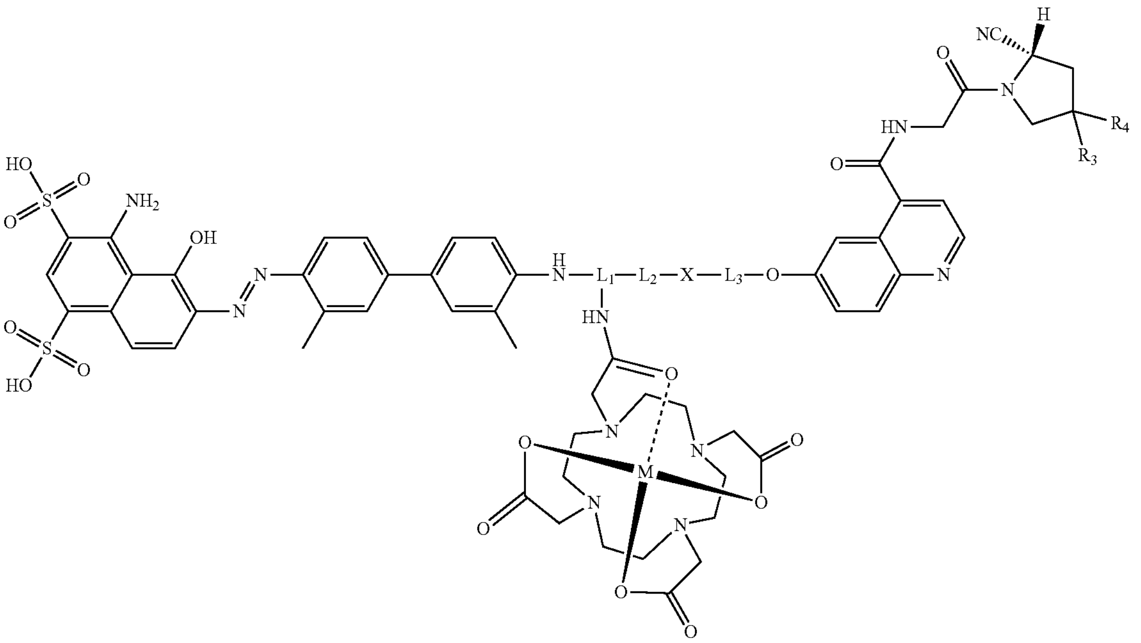

wherein $L_1$ is a lysine or glutamic acid structure, or a derivative compound structure containing a lysine or glutamic acid structure;

$L_2$ is —$(CH_2)_n$—, wherein n is an integer from 0 to 30, wherein each $CH_2$ may be individually substituted or unsubstituted with —O—, —NH—, —(CO)—, —NH(CO)—, or —(CO)—NH—, provided that no two adjacent $CH_2$ groups are substituted;

$L_3$ is —$(CH_2)_m$—, wherein m is an integer from 0 to 30, wherein each $CH_2$ may be individually substituted or unsubstituted with —O— or —(CO)—, provided that no two adjacent $CH_2$ groups are substituted;

The radiolabeled complex of the present disclosure can be prepared from a compound containing a radionuclide and the compound shown in Formula (I) of the present disclosure by a variety of existing labeling methods. A labeling method of the present disclosure preferably includes the following wet method or freeze-drying method.

A wet labeling solution includes: dissolving an appropriate amount of the compound shown in Formula (I) of the present disclosure in a buffer solution or deionized water; and adding a radionuclide solution to the obtained solution for a reaction under closed conditions for 5-40 min to produce a radionuclide labeled complex.

Alternatively, a freeze-drying labeling solution includes: dissolving an appropriate amount of the compound shown in Formula (I) of the present disclosure in a buffer solution or deionized water; treating the obtained solution by aseptic filtration, followed by dividing and separately loading into containers, freeze-drying and sealing with a stopper to obtain a freeze-dried medicine box; and then adding an appropriate amount of an acetic acid solution or a buffer solution to the freeze-dried medicine box for dissolution, and adding a corresponding radionuclide solution for a reaction under closed conditions for 5-40 min to produce a radionuclide labeled complex. The container for loading is preferably a frozen storage tube or a controlled antibiotic bottle. An excipient, such as mannitol and ascorbic acid, can also be added to the medicine box according to the forming situation of a freeze-dried powder in the medicine box, and the medicine box can achieve an optimal forming effect by adjusting the dose of the compound shown in Formula (I) of the present disclosure and the excipient.

Products obtained according to the wet labeling solution and the freeze-drying labeling solution can be further prepared into injections by conventional treatment (such as chromatographic separation and purification, rotary evaporation to remove the solvent, dissolution of residues with PBS or water or normal saline, and aseptic filtration).

In a preferred specific embodiment of the present disclosure, with the compound 20 shown in Formula (II-1) as a ligand, a preferred preparation method of a radiolabeled compound 20 is a wet labeling method. The method includes the following steps: dissolving the compound 20 in a buffer solution or deionized water; adding a fresh radioactive solution for a reaction under closed conditions at 37-90° C. for 5-40 min, followed by cooling; adding water for diluting a reaction solution, followed by separation and purification with a Sep-Pak C18 chromatographic column; rinsing the chromatographic column with a buffer solution or water to remove unreacted radioactive ions; and conducting rinsing with a hydrochloric acid-ethanol solution or an ethanol solution, and conducting dilution with normal saline or PBS, followed by aseptic filtration to obtain an injection of a radiolabeled complex having the structure shown in Formula (IV-1), where a radionuclide M is $^{68}$Ga, $^{177}$Lu, or $^{90}$Y Formula (IV-1)

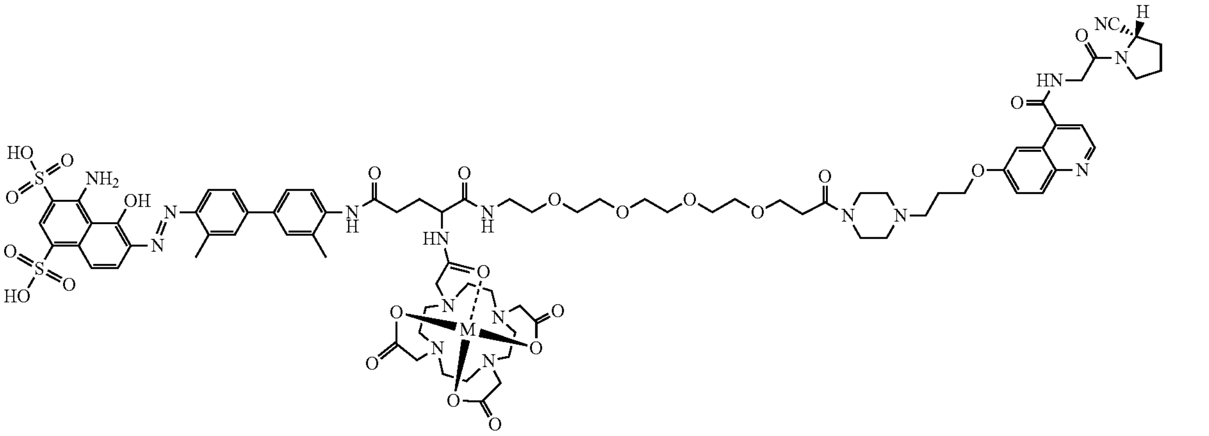

Another preferred preparation method of a radiolabeled compound 20 of the present disclosure is a freeze-drying labeling method. The method includes: dissolving the compound 20 and other necessary reagents in a buffer solution, and treating the obtained solution by aseptic filtration, followed by loading into a frozen storage tube, freeze-drying and sealing to obtain a freeze-dried medicine box; adding an appropriate amount of a buffer solution to the freeze-dried medicine box for dissolution, and adding a newly prepared radioactive solution for a reaction under closed conditions at 37-120° C. for 5-40 min, followed by cooling; adding water for diluting a reaction solution, followed by separation and purification with a Sep-Pak C18 chromatographic column; rinsing the chromatographic column with a buffer solution or water to remove unreacted radioactive ions; and conducting rinsing with a hydrochloric acid-ethanol solution or an ethanol solution, and conducting dilution with normal saline or PBS, followed by aseptic filtration to obtain an injection of a radiolabeled complex having the structure shown in Formula (IV-1), where a radionuclide M is $^{68}$Ga, $^{177}$Lu, or $^{90}$Y.

Other chemicals used in the above synthesis steps are commercially available products.

The buffer solution is a substance for stabilizing the pH value of a reaction solution, and may be acetate, lactate, tartrate, malate, maleate, succinate, ascorbate, carbonate, phosphate and a mixture thereof.

In another aspect, the present disclosure also provides application of the tEB-FAPI compound shown in Formula (I) or a pharmacologically acceptable salt thereof in preparation of medicines in nuclide therapy or imaging of tumors with high expression of FAP.

The present disclosure also provides application of the radiolabeled tEB-FAPI complex shown in Formula (IV) in nuclide therapy and imaging of tumors with high expression of FAP.

In preferred application of the present disclosure, the complex is formulated as an injection, and then intravenously injected into patients with tumors with high expression of FAP.

In the application of the present disclosure, the tumors with high expression of FAP include, but are not limited to, breast cancer, ovarian cancer, lung cancer, colorectal cancer, gastric cancer or pancreatic cancer.

The present disclosure provides a truncated Evans Blue modified fibroblast activation protein inhibitor tEB-FAPI and a radionuclide labeled complex thereof, and also provides a preparation method and a labeling method of the compound. Biological test results show that the inhibitor has the characteristics of significantly prolonging the half-life in blood circulation, improving the uptake and accumulation in tumors and prolonging the retention time. Such novel properties are not available in other FAPI imaging agents at present, and the inhibitor is suitable for nuclide therapy and imaging of tumors with high expression of FAP.

DETAILED DESCRIPTION OF EMBODIMENTS

Technical solutions of the present disclosure are further explained and described below in conjunction with specific embodiments and attached drawings.

Example 1: Preparation of a tEB-FAPI Conjugates Connector (Compound 20)

Synthesis of Compound 2

Figure 1:
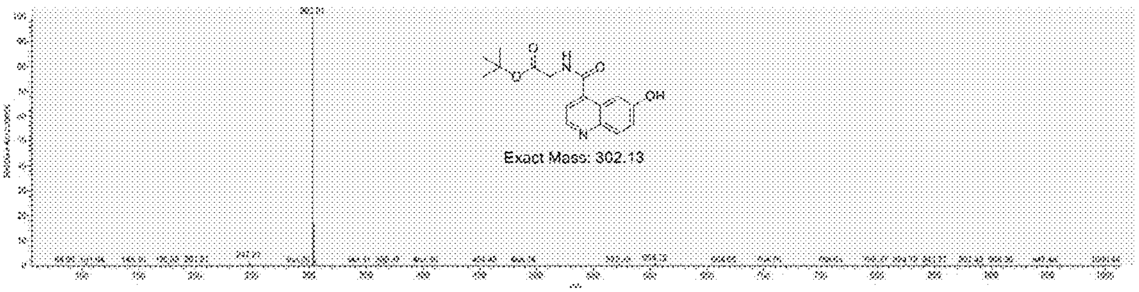
FIG. 1 is a diagram showing mass spectrum of compound 2 in Example 1 of the present disclosure.
Figure 2:
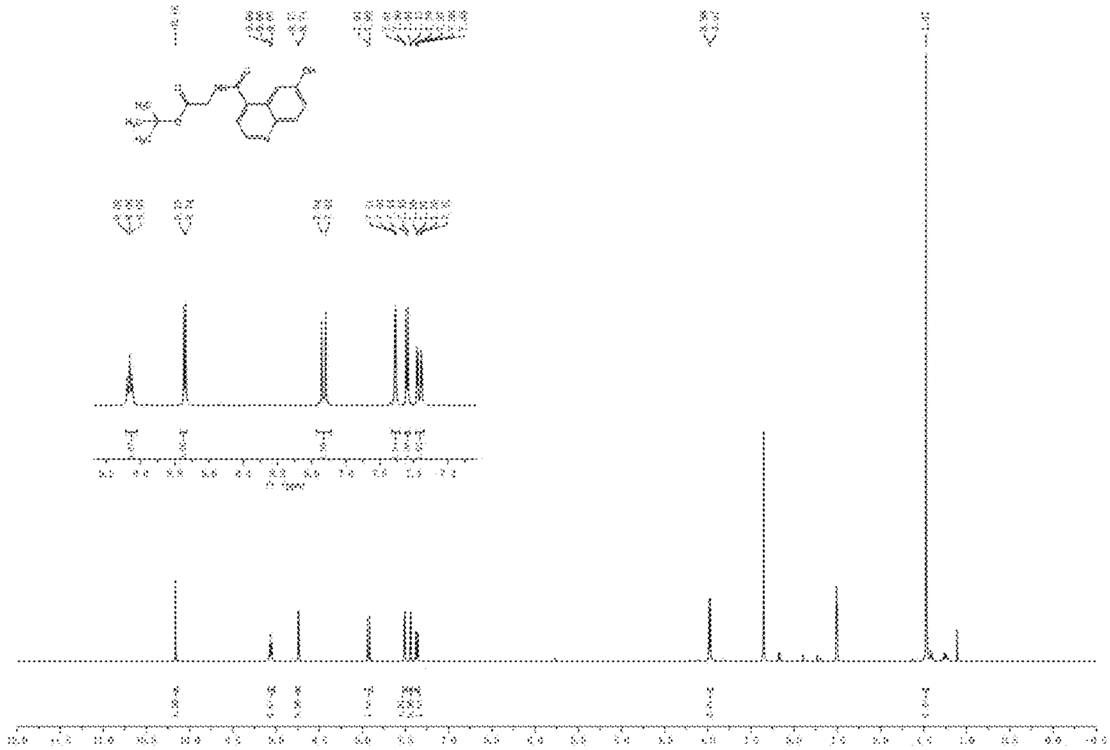
FIG. 2 shows nuclear magnetic hydrogen spectrum of compound 2 in Example 1 of the present disclosure.
Figure 3:
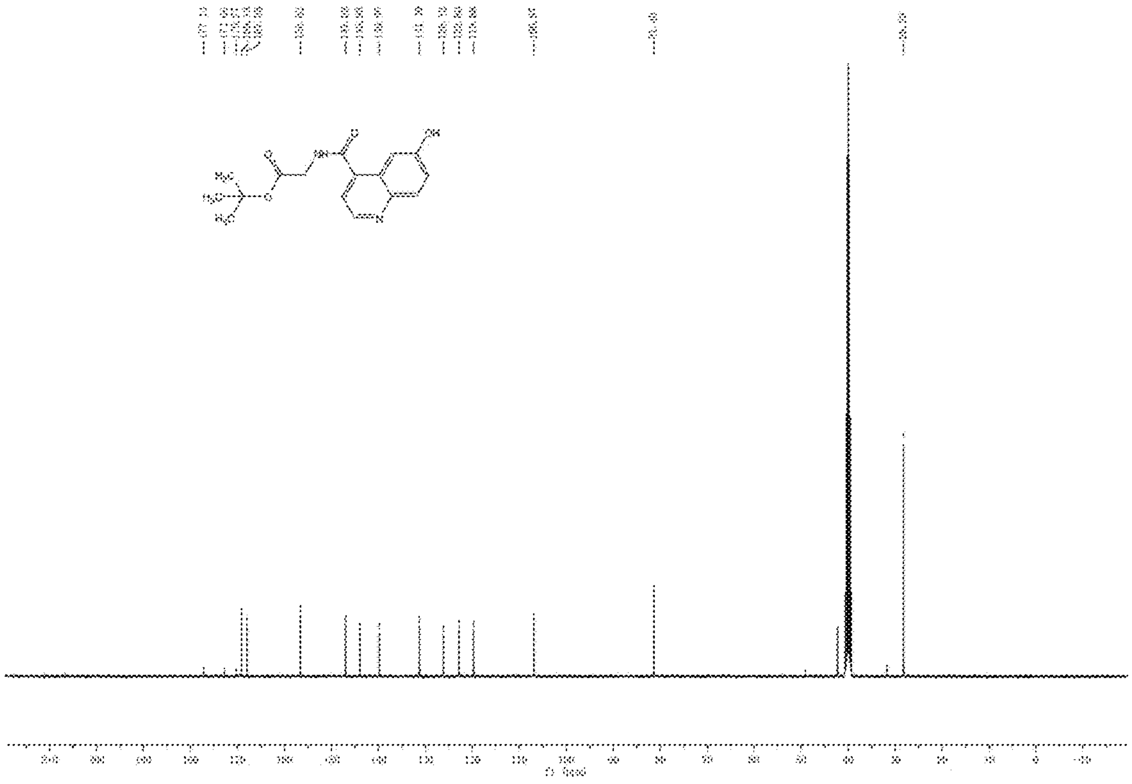
FIG. 3 shows nuclear magnetic carbon spectrum of compound 2 in Example 1 of the present disclosure.

Compound 1 (6-hydroxy-4-quinolinecarboxylic acid, 1.89 g, 10.0 mmol), tert-butyl glycinate (1.89 g, 10.0 mmol), HATU (3.8 g, 10.0 mmol) and N,N-diisopropylethylamine (2.6 g, 20.0 mmol) were sequentially put into 30 mL of N,N-dimethylformamide in a 100 mL flask. A reaction mixture was stirred overnight, and reduced pressure distillation was conducted to remove the solvent to obtain a crude product. Then purification was conducted with a silica gel column (a ratio of dichloromethane to methanol was 30:1) to obtain a white solid compound 2 with a yield of 87%. FIG. 1 is a diagram showing the mass spectrum of compound 2. FIG. 2 shows nuclear magnetic hydrogen spectrum of the compound 2. FIG. 3 shows the nuclear magnetic carbon spectrum of compound 2.

Synthesis of Compound 3

Figure 4:
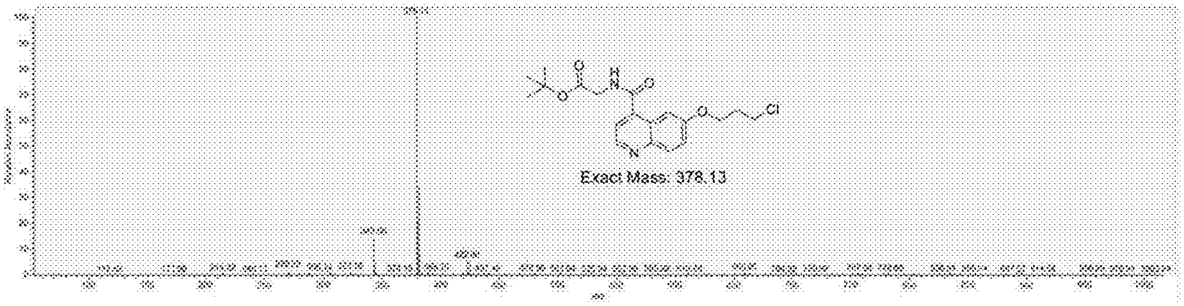
FIG. 4 is a diagram showing mass spectrum of compound 3 in Example 1 of the present disclosure.
Figure 5:
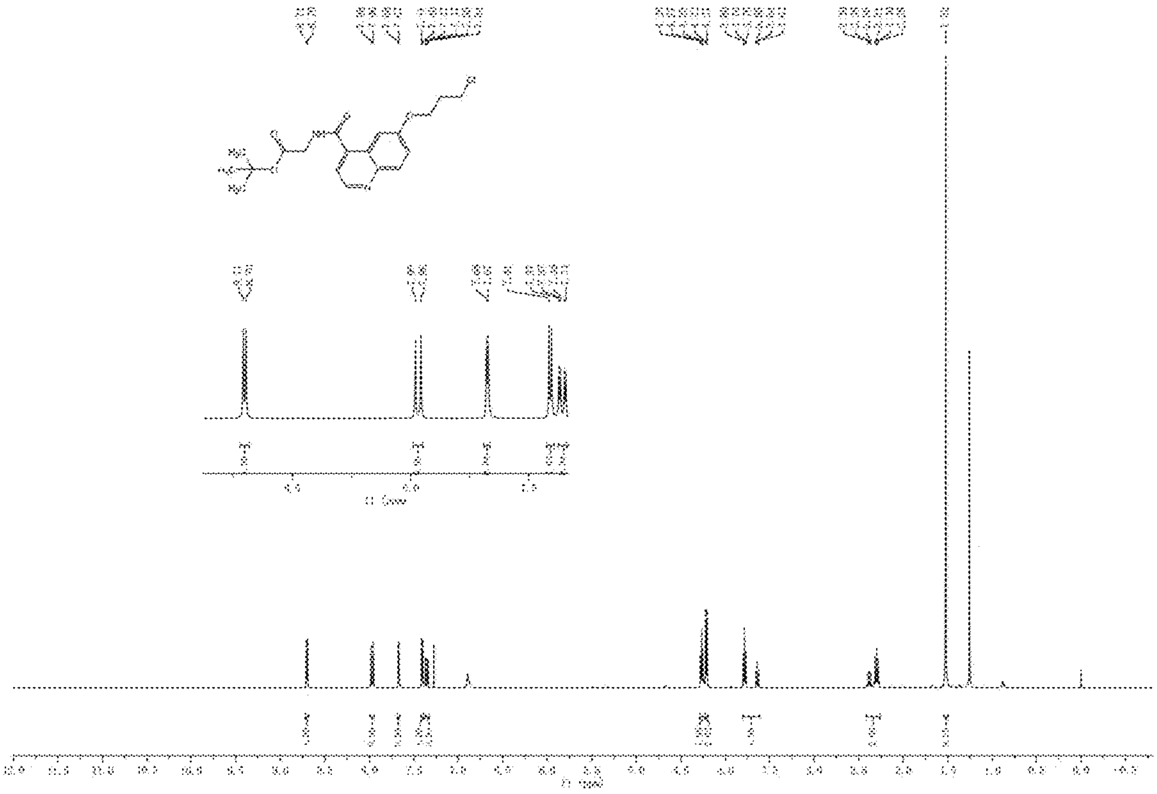
FIG. 5 shows nuclear magnetic hydrogen spectrum of compound 3 in Example 1 of the present disclosure.

Compound 2 (1.51 g, 5.0 mmol), 1-bromo-3-chloropropane (1.55 g, 10.0 mmol) and potassium carbonate (1.38 g, 10.0 mmol) were sequentially put into 50 mL of N,N-dimethylformamide in a 100 mL flask. The system was heated to 60° C. and stirred overnight at 60° C., and reduced pressure distillation was conducted to remove the solvent to obtain a crude product. Then purification was conducted with a silica gel column (a ratio of dichloromethane to methanol was 50:1) to obtain a white solid compound 3 with a yield of 63%. FIG. 4 is a diagram showing the mass spectrum of compound 3. FIG. 5 shows nuclear magnetic hydrogen spectrum of compound 3.

Synthesis of Compound 4

Figure 6:
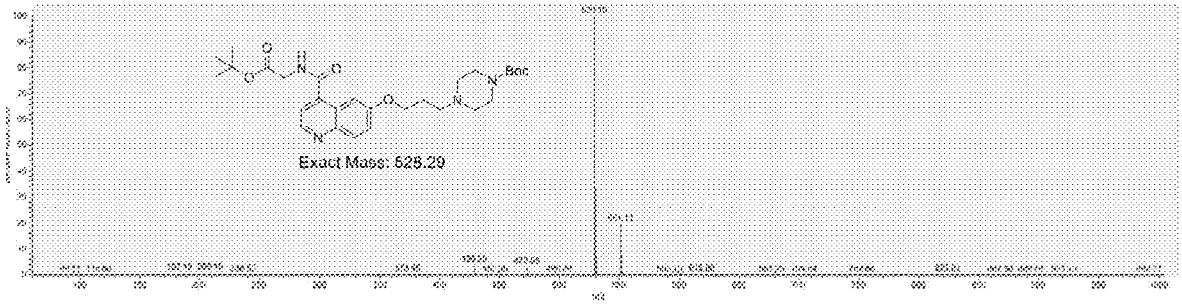
FIG. 6 is a diagram showing mass spectrum of compound 4 in Example 1 of the present disclosure.
Figure 7:
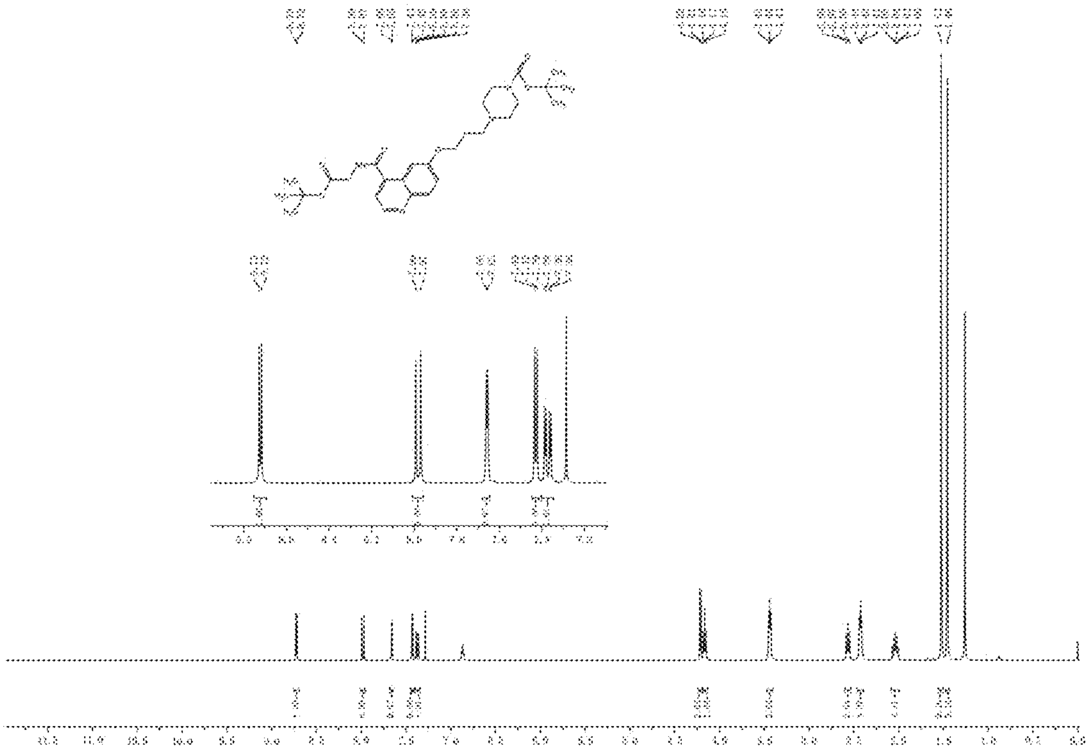
FIG. 7 shows nuclear magnetic hydrogen spectrum of compound 4 in Example 1 of the present disclosure.
Figure 8:
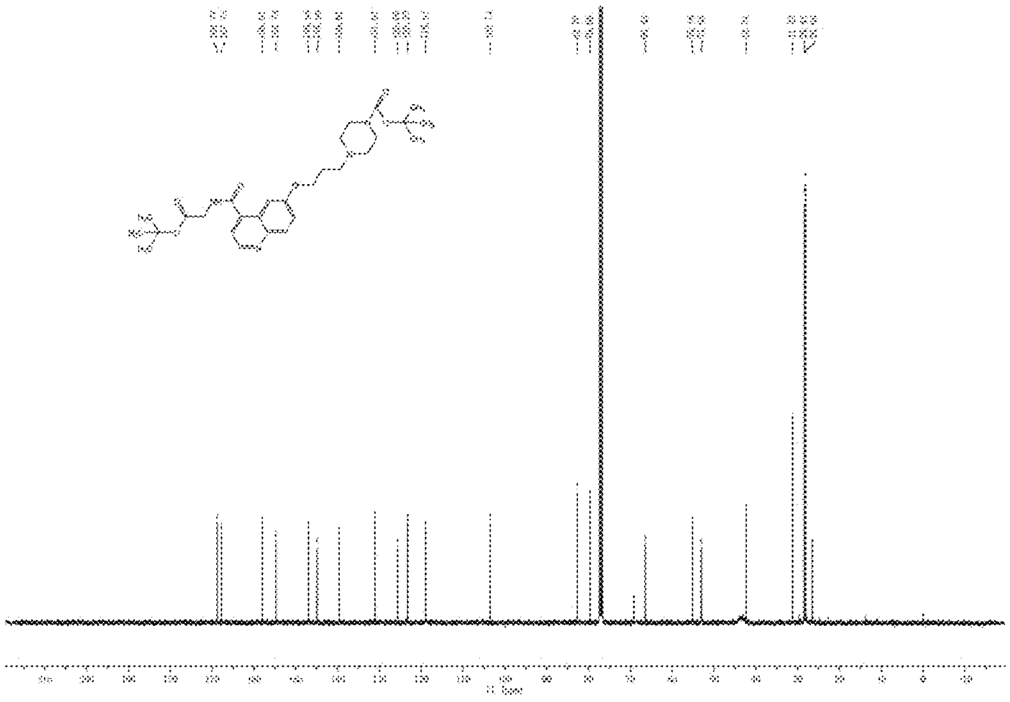
FIG. 8 shows nuclear magnetic carbon spectrum of compound 4 in Example 1 of the present disclosure.

Compound 3 (0.76 g, 2.0 mmol), tert-butyl 1-piperazinecarboxylate (0.55 g, 3.0 mmol) and potassium iodide (0.49 g, 3.0 mmol) were sequentially put into 30 mL of acetonitrile in a 100 mL flask. The system was heated to 60° C. and stirred overnight at 60° C., and reduced pressure distillation was conducted to remove the solvent to obtain a crude product. Then purification was conducted with a silica gel column (a ratio of dichloromethane to methanol was 30:1) to obtain a white solid compound 4 with a yield of 58%. MS(ESI)$_m$/z calculated for [$C_{28}H_{40}N_4O_6$]: 528.29; found: 529.10 $[M+H]^+$. FIG. 6 is a diagram showing the mass spectrum of compound 4. FIG. 7 shows nuclear magnetic hydrogen spectrum of compound 4. FIG. 8 shows the nuclear magnetic carbon spectrum of compound 4.

Synthesis of Compound 5

Compound 4 (0.52 g, 1.0 mmol) was dissolved in 10 mL of a mixed solution of dichloromethane and trifluoroacetic acid (at a volume ratio of 9:1) in an ice bath. The system was heated to room temperature for a reaction for 2 h, and after the reaction was completed, reduced pressure distillation was conducted to remove the solvent. Then the resulting product was dissolved in 10 mL of N,N-dimethylformamide for later use.

Synthesis of Compound 6

Di-tert-butyl dicarbonate (0.22 g, 1.0 mmol) and N,N-diisopropylethylamine (0.39 g, 3.0 mmol) were separately added to an N,N-dimethylformamide solution of the compound 5. The system was stirred overnight at room temperature, and reduced pressure distillation was conducted to remove the solvent to obtain a crude product. Then purification was conducted with a silica gel column (a ratio of dichloromethane to methanol was 10:1) to obtain a white solid compound 6 with a yield of 72%.

Synthesis of Compound 7

Figure 9:
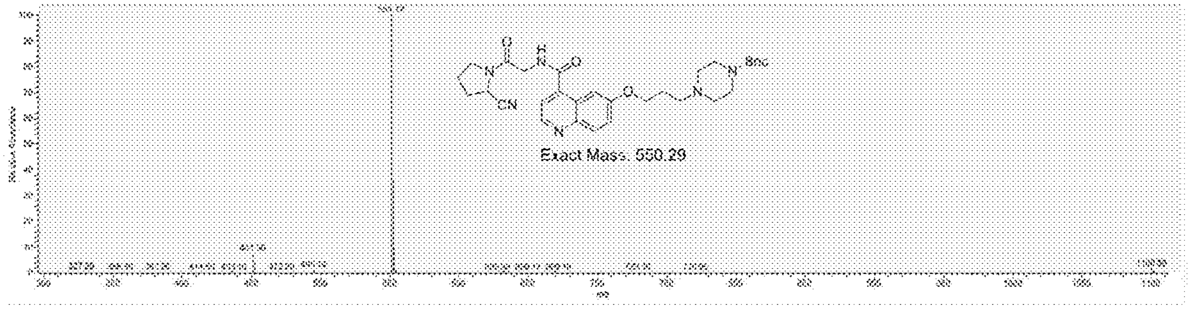
FIG. 9 is a diagram showing mass spectrum of compound 7 in Example 1 of the present disclosure.
Figure 10:
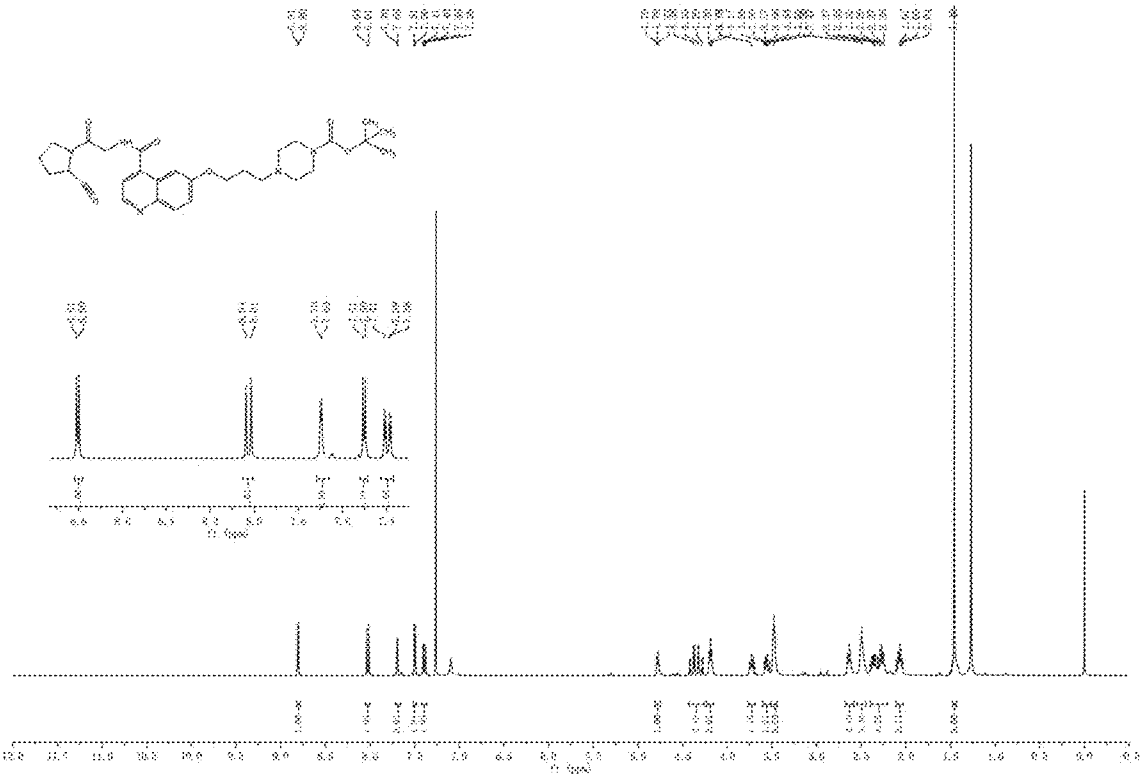
FIG. 10 shows nuclear magnetic hydrogen spectrum of compound 7 in Example 1 of the present disclosure.
Figure 11:
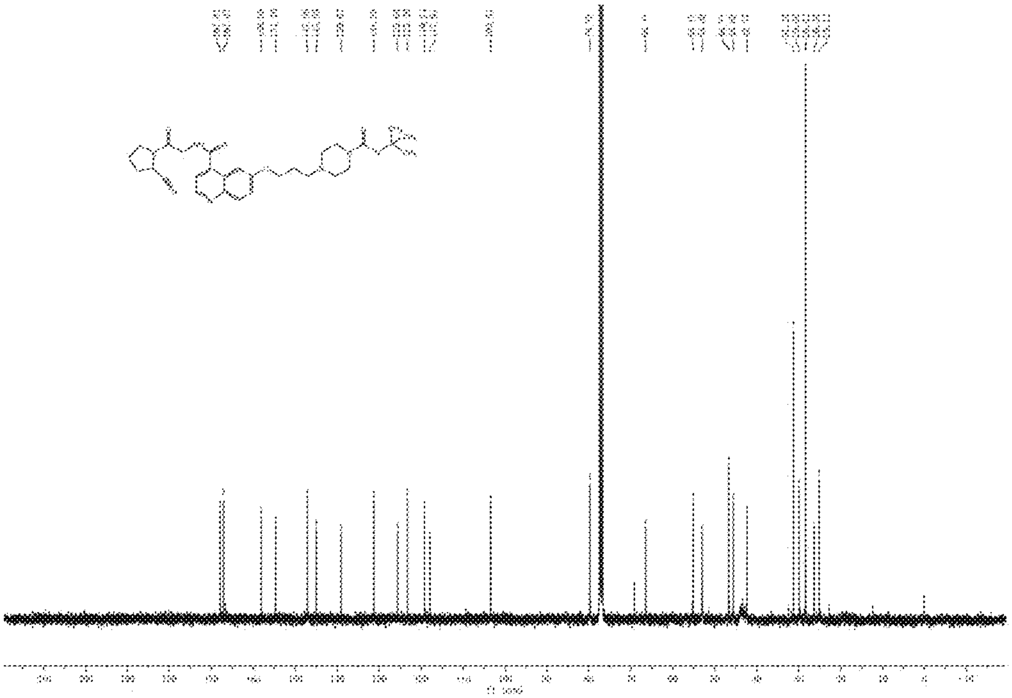
FIG. 11 shows nuclear magnetic carbon spectrum of compound 7 in Example 1 of the present disclosure.

Compound 6 (0.47 g, 1.0 mmol), (S)-pyrrolidene-2-carbonitrile hydrochloride (0.13 g, 10.0 mmol), HATU (0.38 g, 1.0 mmol) and N,N-diisopropylethylamine (0.26 g, 2.0 mmol) were sequentially put into 10 mL of N,N-dimethylformamide in a 100 mL flask. A reaction mixture was stirred at room temperature until a reaction was completed, and reduced pressure distillation was conducted to remove the solvent to obtain a crude product. Then purification was conducted with a silica gel column (a ratio of dichloromethane to methanol was 50:1) to obtain a white solid compound 7 with a yield of 85%. FIG. 9 is a diagram showing mass spectrum of compound 7. FIG. 10 shows nuclear magnetic hydrogen spectrum of compound 7. FIG. 11 shows the nuclear magnetic carbon spectrum of compound 7.

Synthesis of Compound 8

Compound 7 (0.55 g, 1.0 mmol) and p-toluenesulfonic acid monohydrate (0.27 g, 1.5 mmol) were sequentially put into 10 mL of acetonitrile in a 100 mL flask. The reaction system was heated to 60° C. and stirred until a reaction was completed, and reduced pressure distillation was conducted to remove the solvent to obtain a crude product.

Synthesis of a Compound 9

5,8,11,14-tetraoxa-2-azaheptadecanedioic acid-1-tert-butyl ester (0.19 g, 1.0 mmol), HATU (0.38 g, 1.0 mmol), N,N-diisopropylethylamine (0.26 g, 2.0 mmol) and 10 mL of N,N-dimethylformamide were separately put into the reaction flask of compound 8. A reaction mixture was stirred overnight, and reduced pressure distillation was conducted to remove the solvent to obtain a crude product. Then purification was conducted with a silica gel column (ratio of dichloromethane to methanol was 50:1) to obtain a white solid compound 9 with a yield of 64%.

Synthesis of Compound 10

Figure 12:
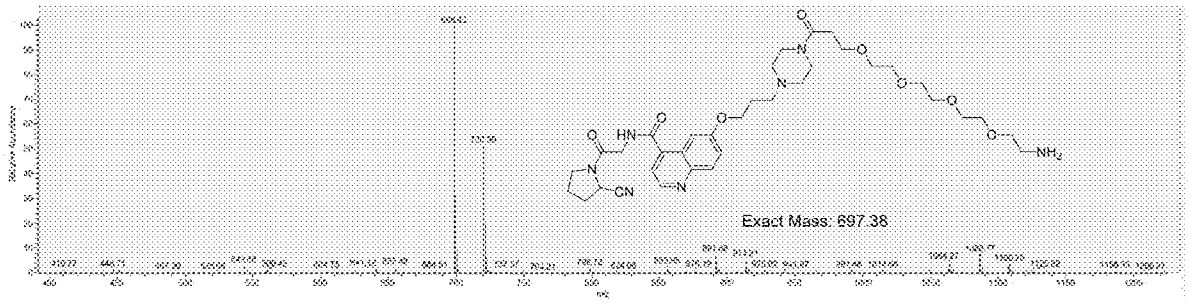
FIG. 12 is a diagram showing mass spectrum of compound 10 in Example 1 of the present disclosure.

Compound 9 (0.61 g, 1.0 mmol) and p-toluenesulfonic acid monohydrate (0.27 g, 1.5 mmol) were sequentially put into 10 mL of acetonitrile in a 100 mL flask. The reaction system was heated to 60° C. and stirred until a reaction was completed, and reduced pressure distillation was conducted to remove the solvent to obtain a crude product. Then purification was conducted with a silica gel column (ratio of dichloromethane to methanol was 10:1) to obtain a white solid compound 10 with a yield of 59%. MS(ESI) m/z calculated for [$C_{35}H_{51}N_7O_8$]: 697.38; found: 698.43 $[M+H]^+$. FIG. 12 is a diagram showing the mass spectrum of the compound 10.

A synthesis route in the above steps is as follows:

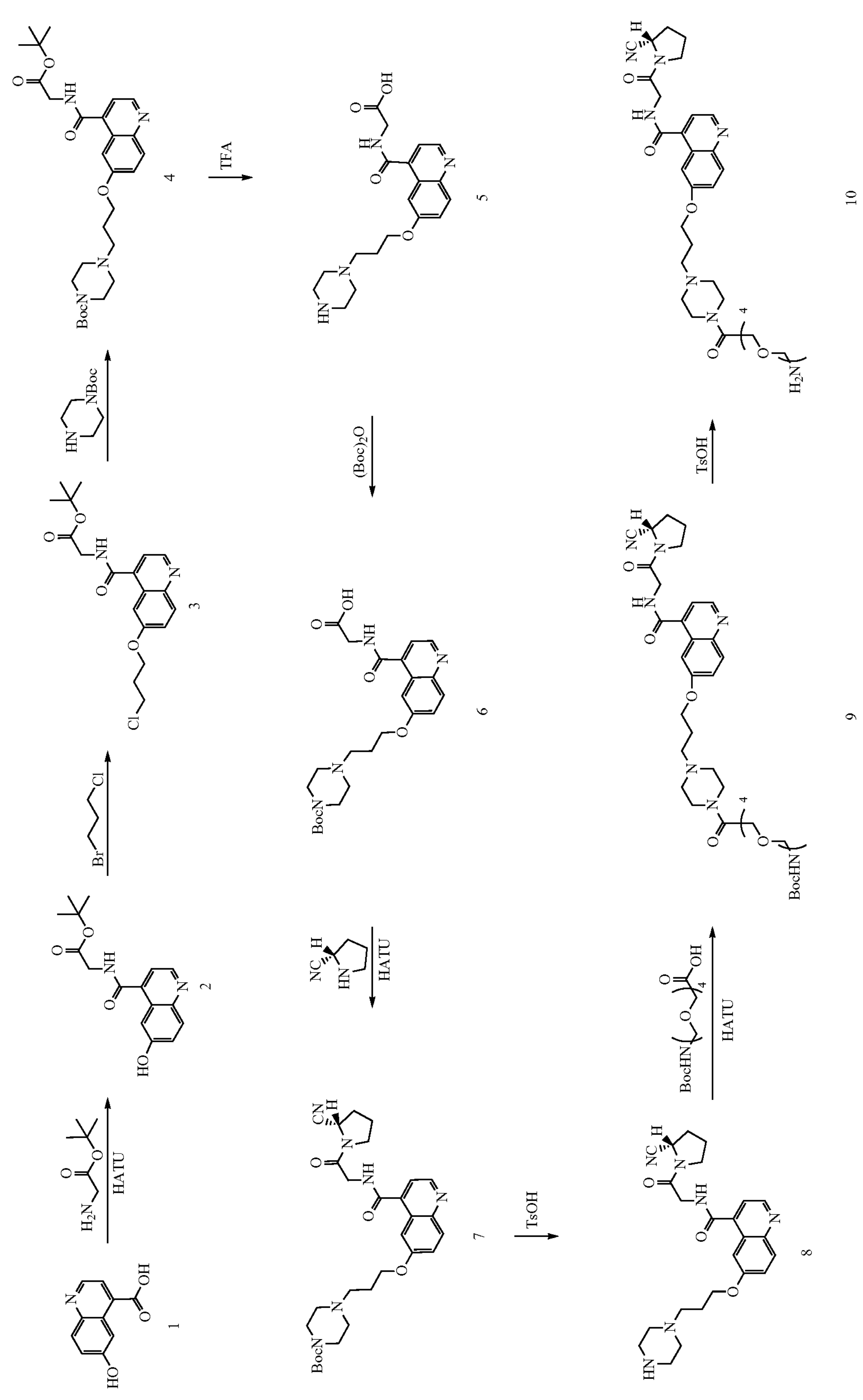
1
HATU
2
3
4
TFA
5
$(Boc)_2O$
6
HATU
7
TsOH
8
HATU
9
TsOH
10

Synthesis of Compound 12

4,4'-Diamino-3,3'-dimethyl biphenyl (compound 11) (2.12 g, 10.0 mmol), di-tert-butyl dicarbonate (2.2 g, 10.0 mmol), N,N-diisopropylethylamine (1.3 g, 10.0 mmol) and 20 mL of dichloromethane were separately put into a 100 mL flask, and stirred overnight at room temperature. After monitoring by HPLC that a reaction was completed (r.t. was 10.13 min), reduced pressure distillation was conducted to remove the solvent to obtain a crude product. Then purification was conducted with a silica gel column (ratio of petroleum ether to ethyl acetate was 5:1) to obtain a white solid compound 12 with a yield of 59%.

Synthesis of Compound 13

Compound 12 (0.31 g, 1.0 mmol) and 4 mL of acetonitrile were separately put into a 50 mL flask in an ice bath, 1.5 mL of 2 M hydrochloric acid was added dropwise to the reaction flask for a reaction for 15 min, and sodium nitrite (0.068 g, 1.0 mmol) was added to 2 mL of water for dissolution and then added dropwise to the reaction flask for reaction for half an hour to obtain a solution A for later use. Monosodium 1-amino-8-naphthol-2,4-disulfonate (0.33 g, 1.0 mmol), sodium carbonate (0.105 g, 1.0 mmol) and 5 mL of water were added to another 50 mL reaction flask in an ice bath to obtain a solution B, and the solution A was slowly added dropwise to the solution B and stirred for reaction for 2 h in the ice bath. Then purification was conducted with a reversed phase column, followed by freeze-drying to obtain pure compound 13 with a yield of 47%.

Synthesis of Compound 14

Compound 13 (0.52 g, 1.0 mmol) was dissolved in trifluoroacetic acid in an ice bath. The system was heated to room temperature for a reaction for 2 h, and after the reaction was completed, reduced pressure distillation was conducted to remove the solvent to obtain a crude product. Then purification was conducted on the crude product with a reversed phase column, followed by freeze-drying to obtain pure compound 14 with a yield of 73%.

Synthesis of Compound 15

Compound 14 (0.54 g, 1.0 mmol), N-tert-butyloxycarbonyl-L-glutamic acid-1-tert-butyl ester (0.30 g, 1.0 mmol), HATU (0.38 g, 1.0 mmol), N,N-diisopropylethylamine (0.26 g, 2.0 mmol) and 10 mL of N,N-dimethylformamide were separately put into a 100 mL flask. A reaction mixture was stirred until a reaction was completed, and reduced pressure distillation was conducted to remove the solvent to obtain a crude product. Then purification was conducted on the crude product with a reversed phase column, followed by freeze-drying to obtain pure compound 15 with a yield of 52%.

Synthesis of Compound 16

Tert-butyl and Boc protective groups were removed using a mixture of thioanisole, 1,2-ethanedithiol, anisole and TFA (at a ratio of 5:3:2:90) at room temperature. After a reaction was completed, the TFA was removed by an argon flow, and the resulting product was dissolved in 10 mL of N,N-dimethylformamide for later use.

Synthesis of Compound 17

Di-tert-butyl dicarbonate (0.22 g, 1.0 mmol) and N,N-diisopropylethylamine (0.39 g, 3.0 mmol) were separately added to an N,N-dimethylformamide solution of the compound 16. The system was stirred overnight at room temperature, and a reaction was completed according to monitoring by HPLC (r.t. was 10.84 min). Reduced pressure distillation was conducted to remove the solvent to obtain a crude product. Then purification was conducted on the crude product with a reversed phase column, followed by freeze-drying to obtain pure compound 17 with a yield of 43% in two steps.

Synthesis of Compound 18

Compound 17 (0.77 g, 1.0 mmol), compound 10 (0.51 g, 1.0 mmol), HATU (0.38 g, 1.0 mmol), N,N-diisopropylethylamine (0.26 g, 2.0 mmol) and 10 mL of N,N-dimethylformamide were separately put into a 50 mL flask. A reaction mixture was stirred for a reaction, and the reaction was completed according to monitoring by HPLC (r.t. was 12.16 min). Reduced pressure distillation was conducted to remove the solvent to obtain a crude product. Then purification was conducted on the crude product with a reversed phase column, followed by freeze-drying to obtain pure compound 18 with a yield of 55%.

Synthesis of Compound 19

Compound 15 (0.13 g, 0.1 mmol) and p-toluenesulfonic acid monohydrate (0.05 g, 0.3 mmol) were sequentially put into 5 mL of acetonitrile in a 25 mL flask. The reaction system was heated to 60° C. and stirred for reaction, and the process of removing protective groups was monitored by HPLC until the reaction was completed (r.t. was 10.47 min). Reduced pressure distillation was conducted to remove the solvent to obtain a crude product. Then purification was conducted on the crude product with a reversed phase column, followed by freeze-drying to obtain pure compound 19 with a yield of 61%.

Synthesis of Compound 20

Figure 13:
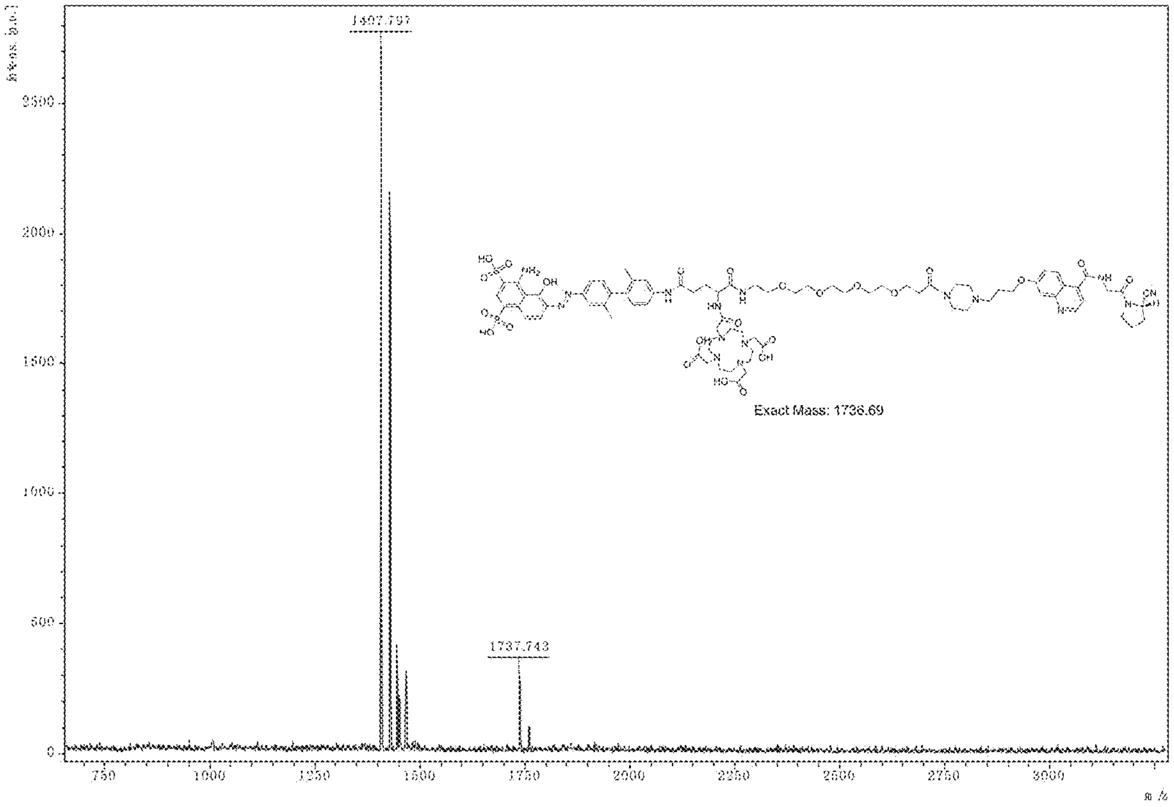
FIG. 13 is a diagram showing mass spectrum of compound 20 in Example 1 of the present disclosure.

Compound 19 (0.12 g, 0.1 mmol), DOTA-NHS (0.05 g, 0.1 mmol) and N,N-diisopropylethylamine (0.04 g, 0.3 mmol) were sequentially put into 5 mL of N,N-dimethylformamide in a 25 mL flask. The reaction system was stirred for reaction at room temperature, and the process of removing protective groups was monitored by HPLC until the reaction was completed (r.t. was 11.35 min). Reduced pressure distillation was conducted to remove the solvent to obtain a crude product. Then purification was conducted on the crude product with a reversed phase column, followed by freeze-drying to obtain pure compound 20 with a yield of 53%. MS(ESI)$_m$/z calculated for [$C_{80}H_{104}N_{16}O_{24}S_2$]: 1736.69; found: 1737.743 $[M+H]^+$. FIG. 13 is a diagram showing mass spectrum of compound 20.

A synthesis route in the above steps is as follows:

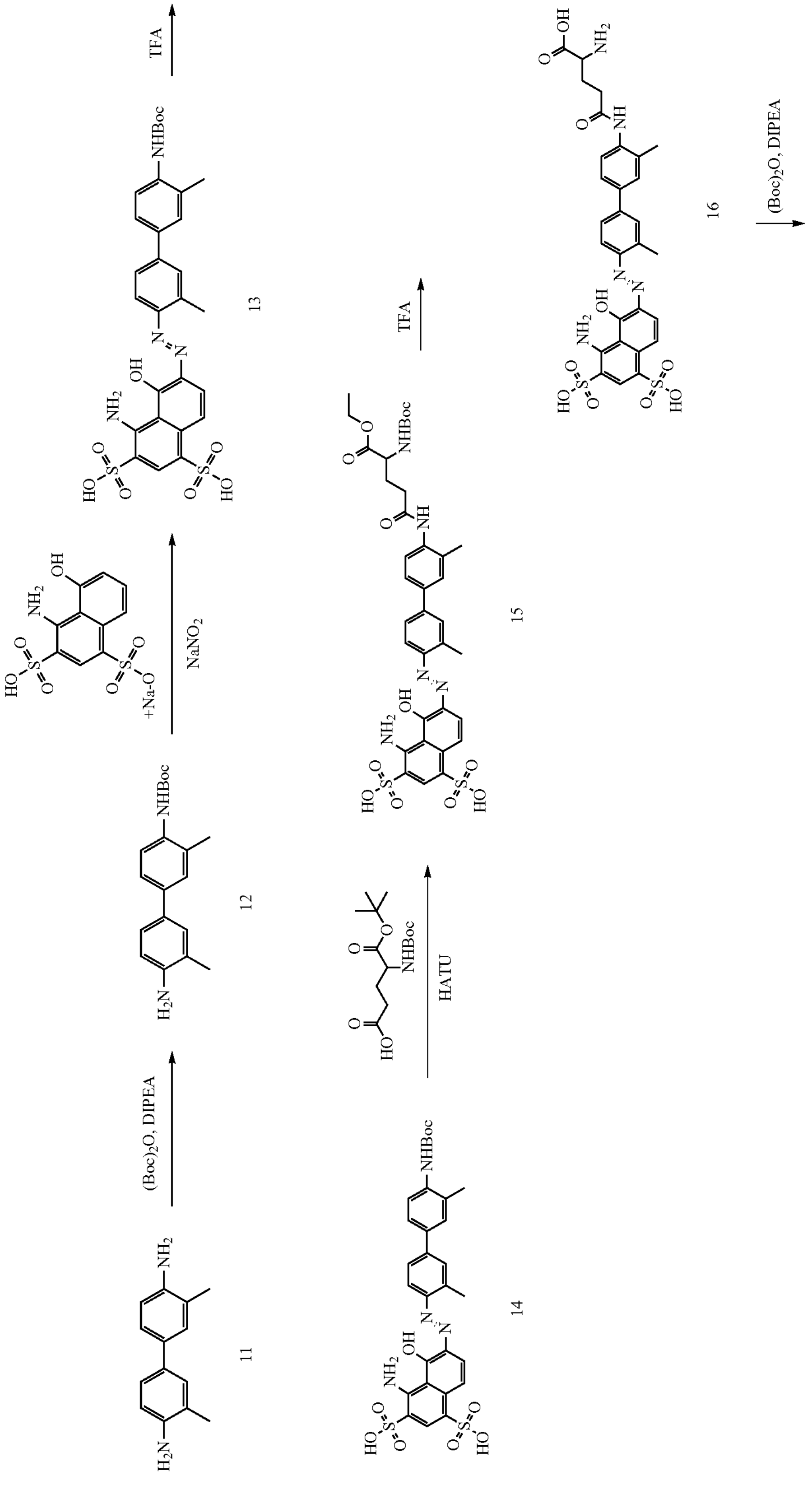
(Boc)$_2$O, DIPEA
11
12
NaNO$_2$
13
TFA
HATU
14
15
TFA
16
(Boc)$_2$O, DIPEA -continued
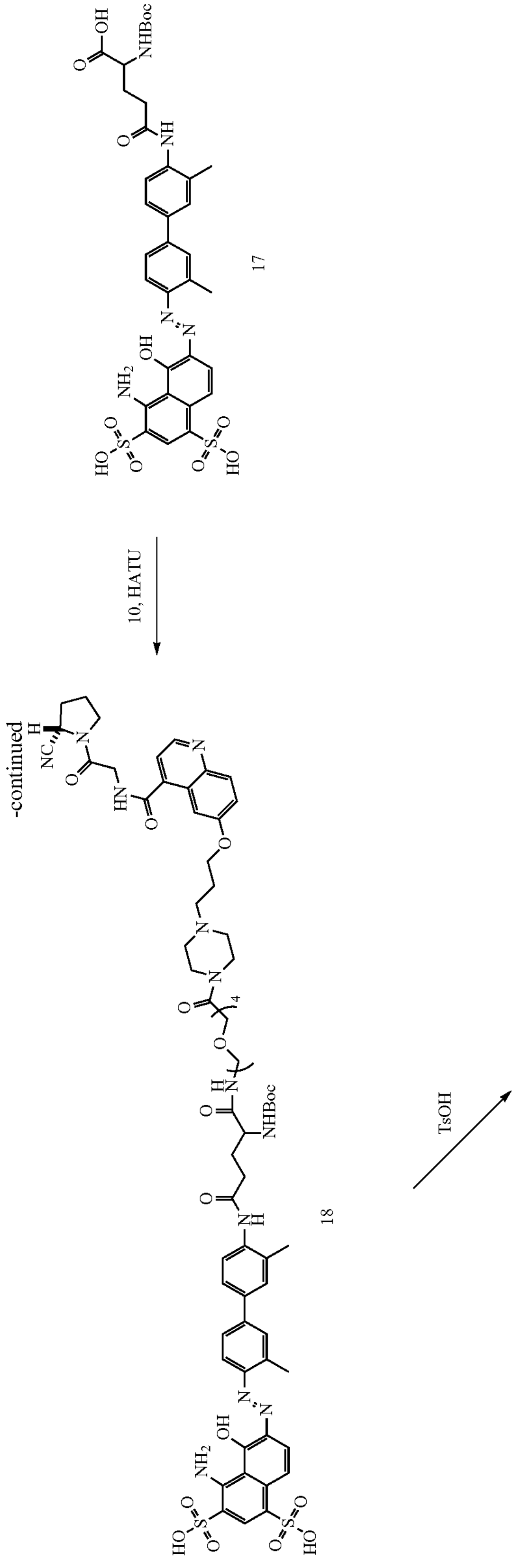
17
18

-continued
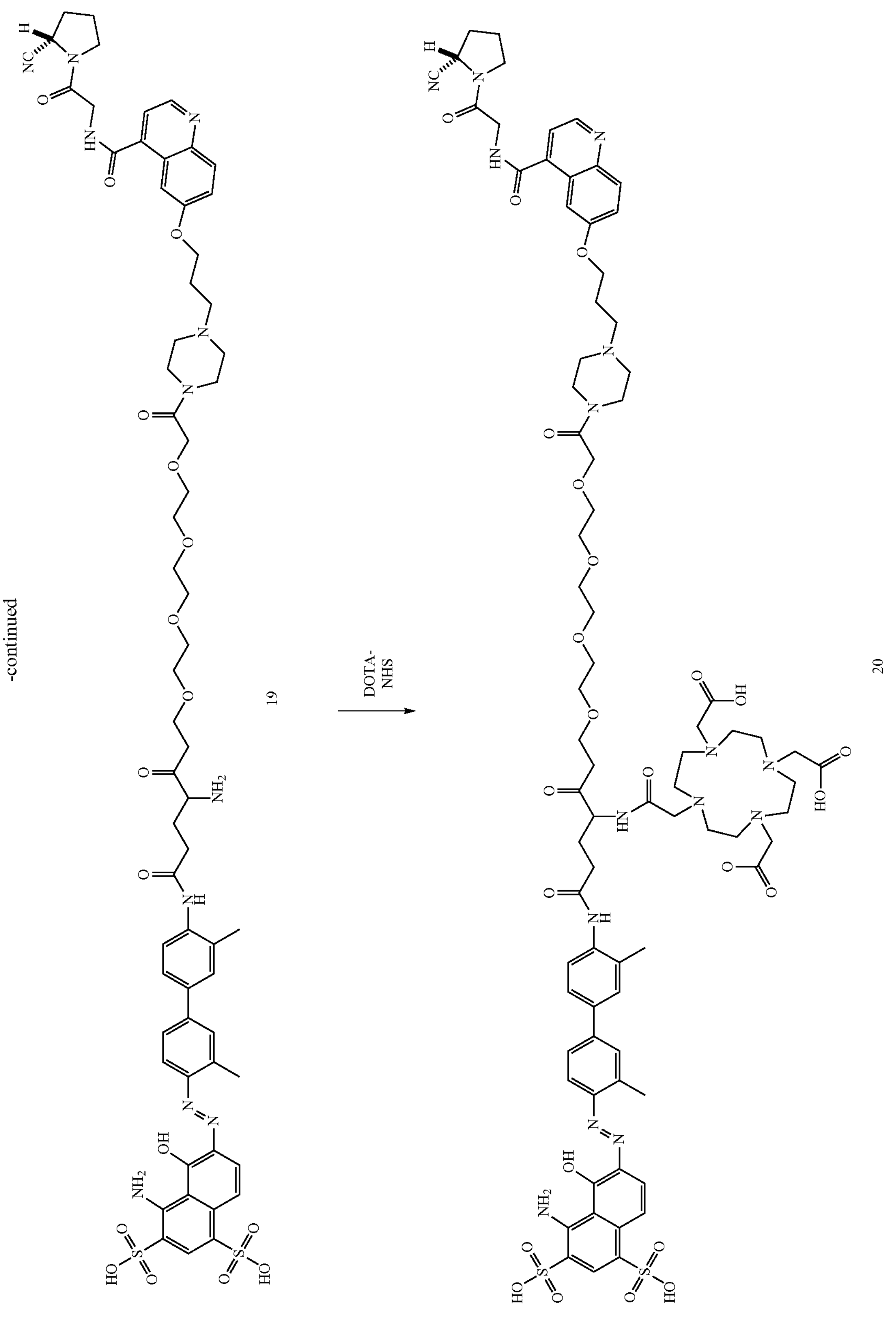
19
20

Examples 2-Examples 16

Compounds in Examples 2-Examples 16 have structures shown in Formula (II-2) to Formula (II-16) respectively, and preparation methods of the compounds can refer to the preparation method in Example 1. The glutamic acid structure reacting with the compound 14 was substituted with a lysine structure, or the 5,8,11,14-tetraoxa-2-azaheptadecanedioic acid-1-tert-butyl ester reacting with the compound 8 was substituted with 5,8,11-trioxa-2-azatridecanediic acid-1-tert-butyl ester, tert-butyl 9-amino-4,7-dioxazononate, tert-butyl glycinate or other suitable compounds, or the (S)-pyrrolidene-2-carbonitrile hydrochloride reacting with the compound 6 was substituted with 3,3-difluoropyrrolidene hydrochloride, or the above compounds were substituted at the same time to obtain corresponding structures as follows:

Formula (II-2)

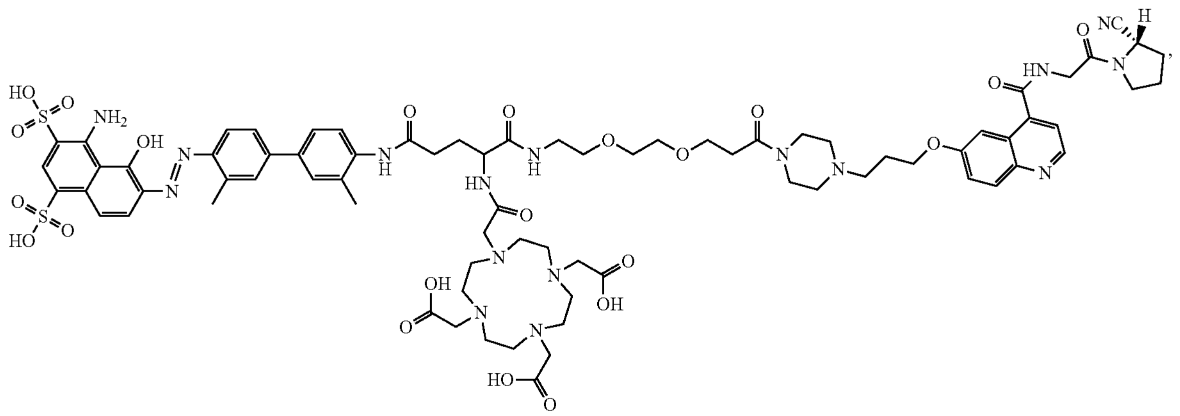

Formula (II-3)

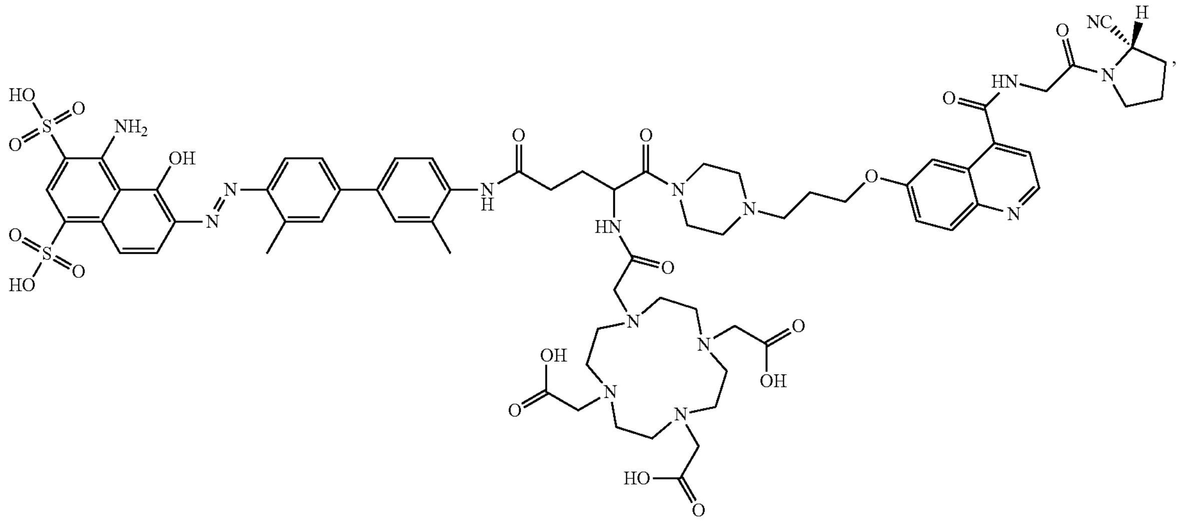

-continued
Formula (II-4)
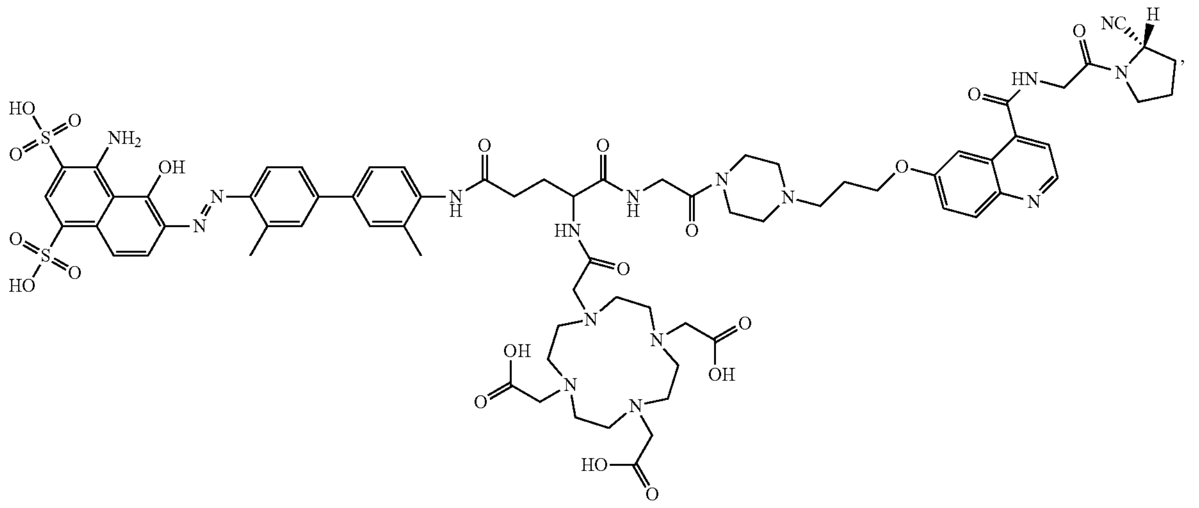
Formula (II-5)
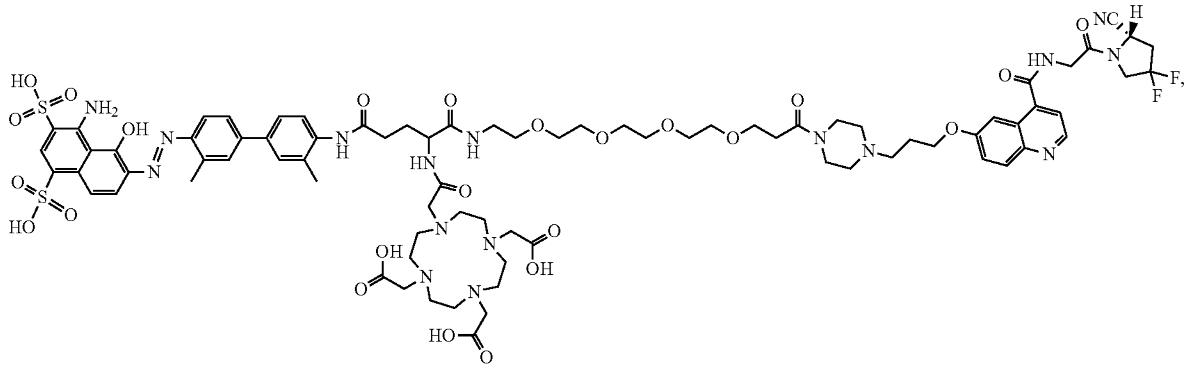
Formula (II-6)
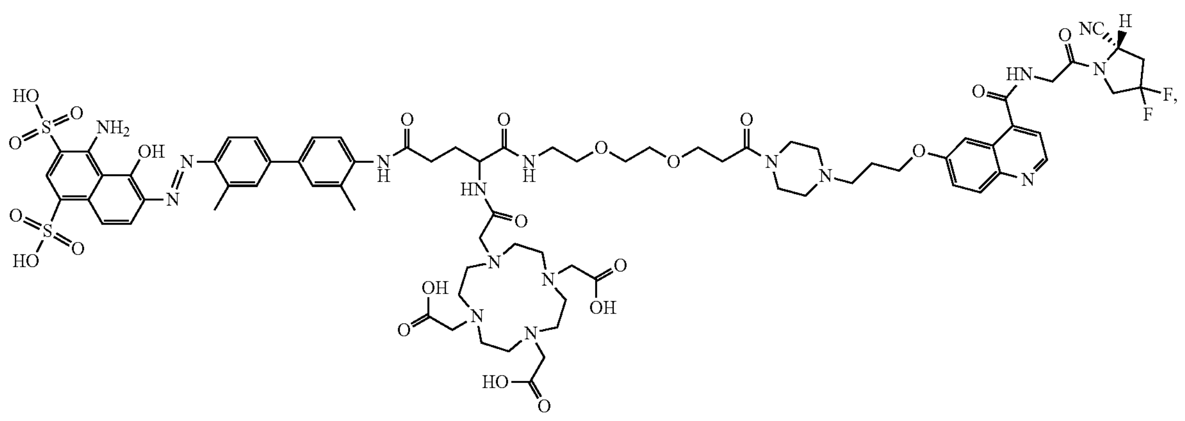

-continued
Formula (II-7)
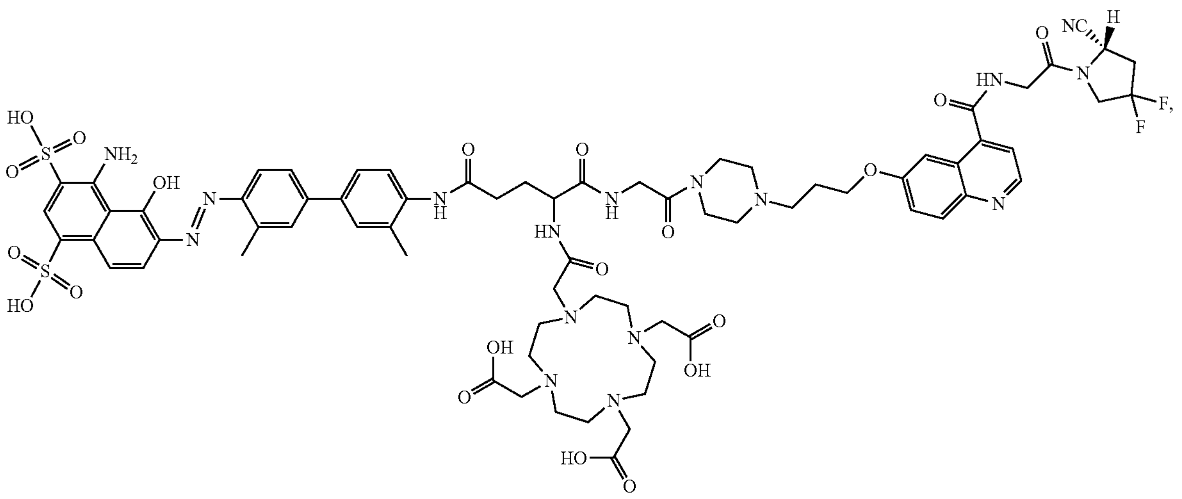
Formula (II-8)
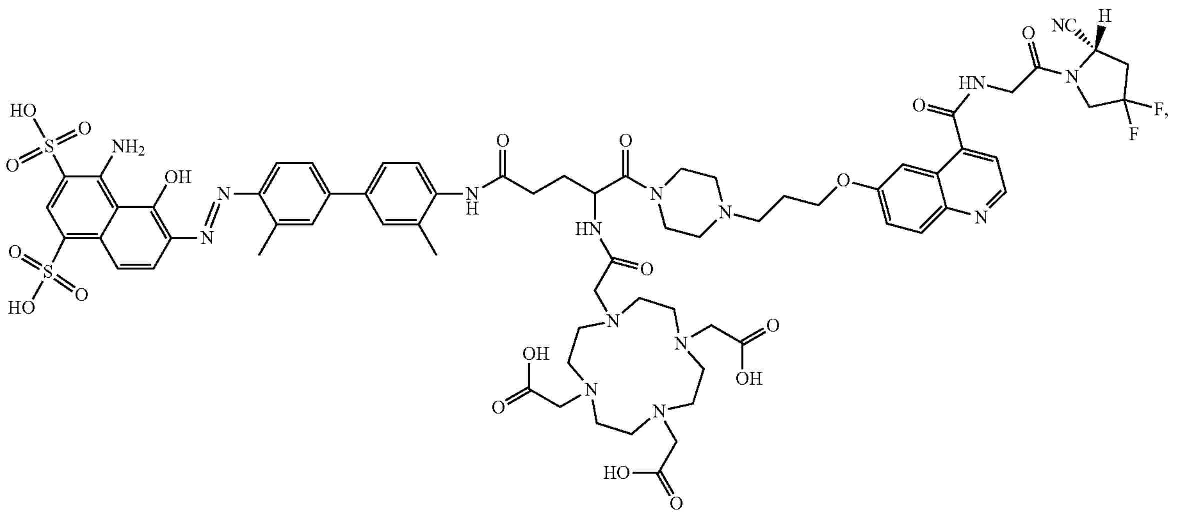
Formula (II-9)
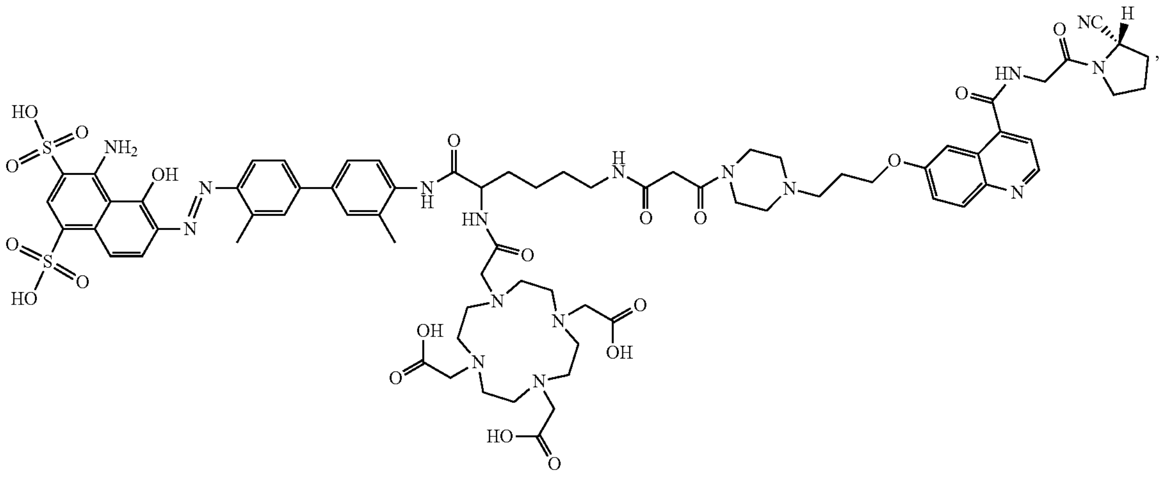

-continued
Formula (II-10)
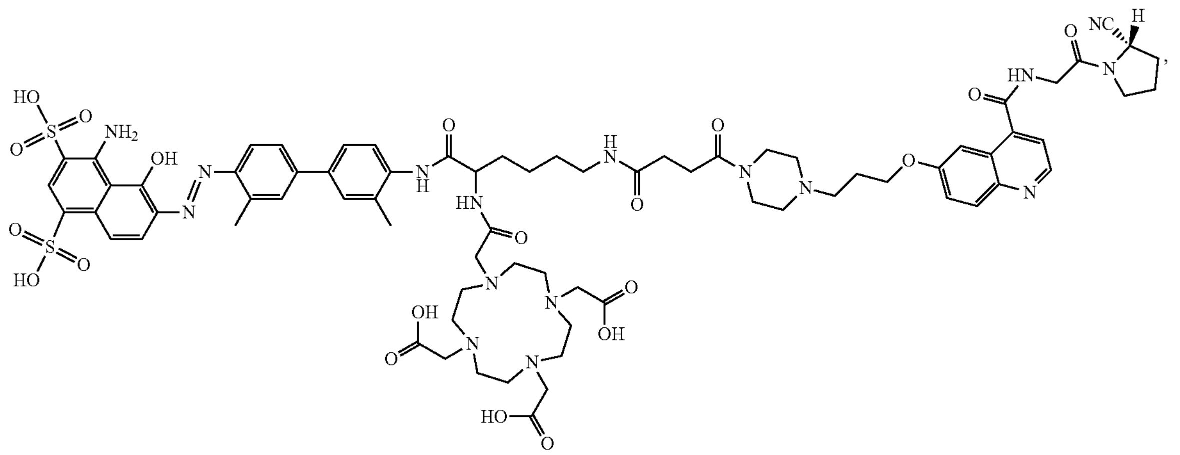
Formula (II-11)
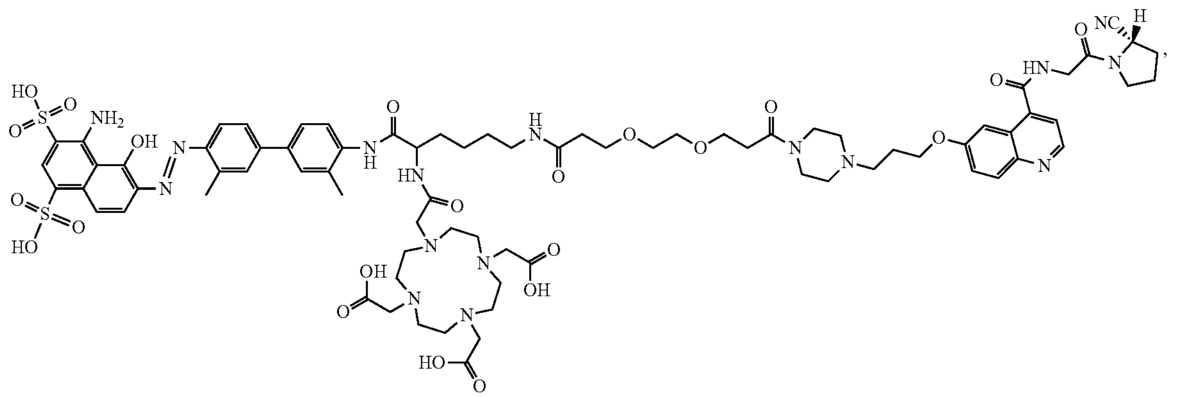
Formula (II-12)
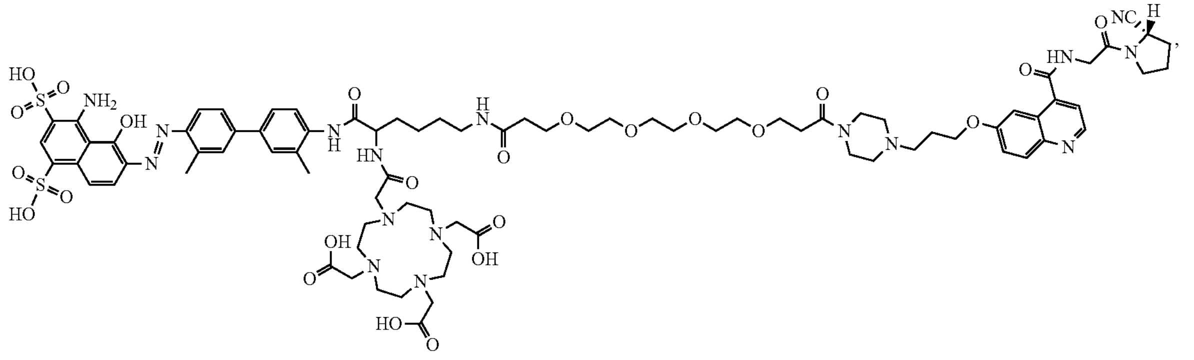

Figure 14:
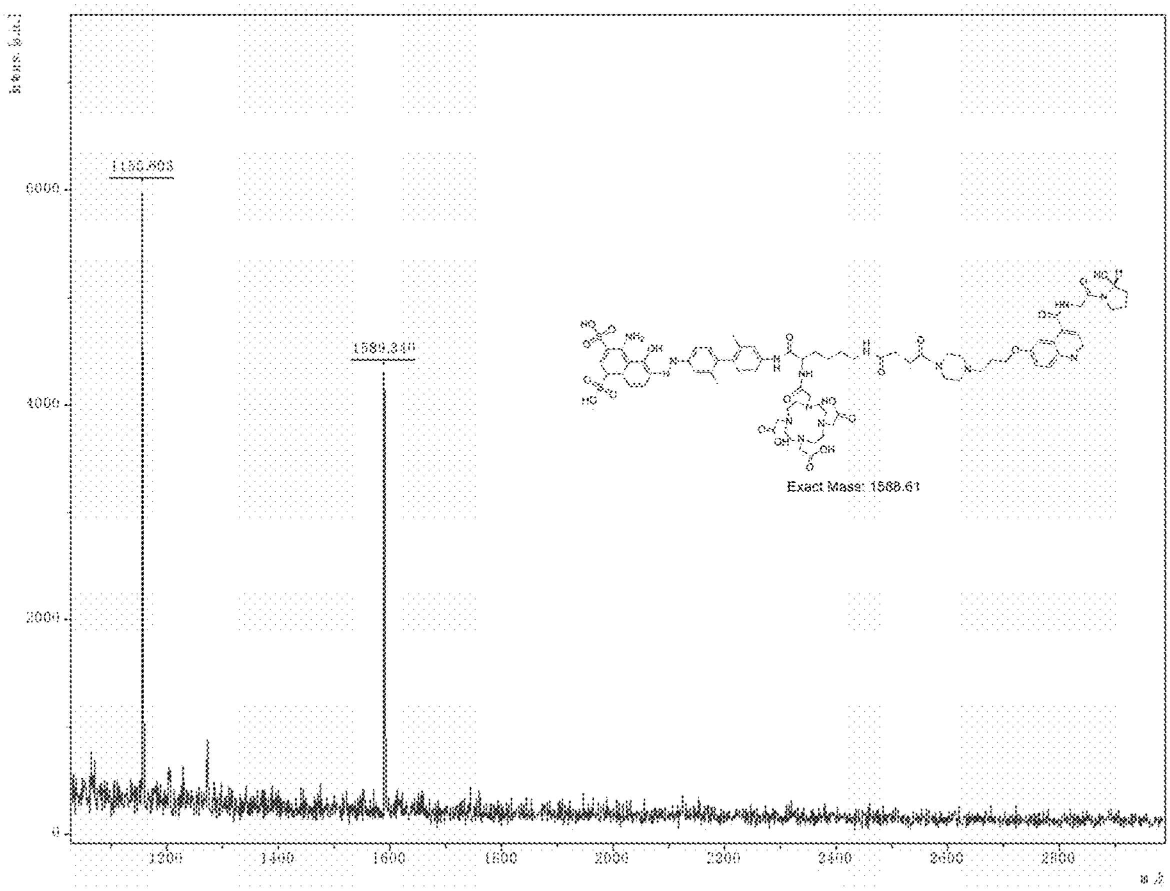
FIG. 14 is a diagram showing mass spectrum of compound in Example 10 of the present disclosure.
Figure 15:
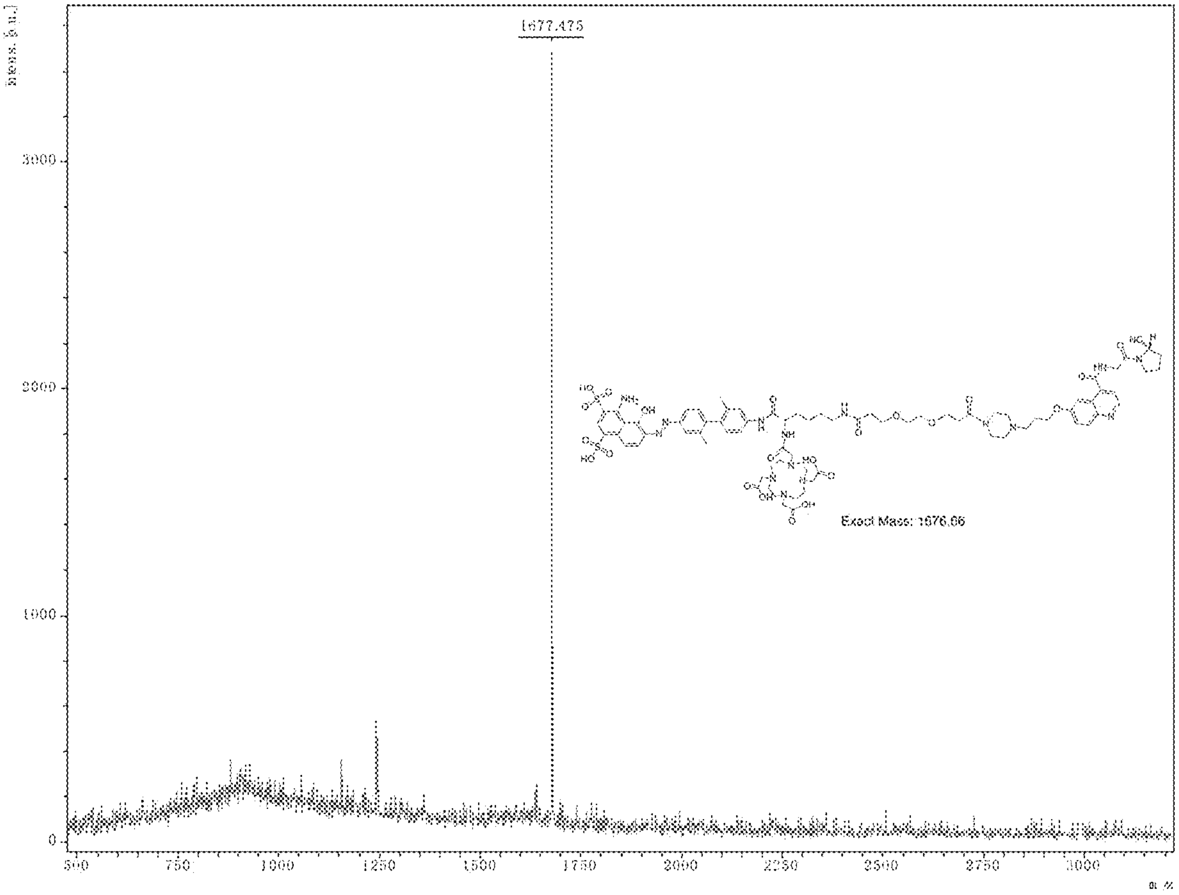
FIG. 15 is a diagram showing the mass spectrum of a compound in Example 11 of the present disclosure.
Figure 16:
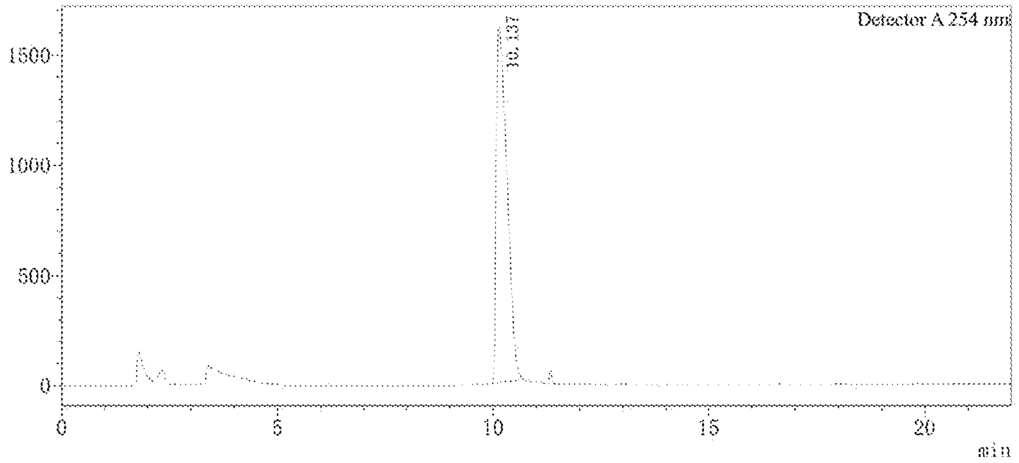
FIG. 16 is an HPLC chromatogram of compound 10 in Example 1 of the present disclosure.
Figure 17:
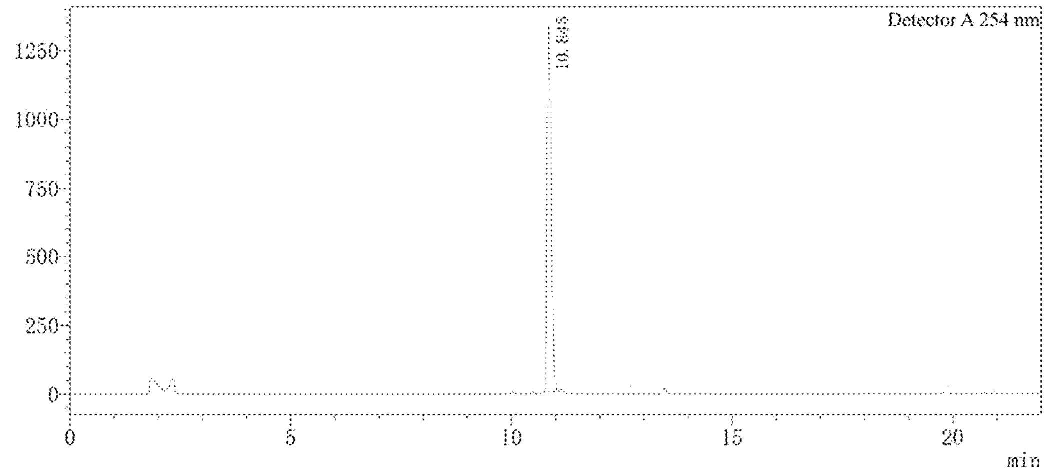
FIG. 17 is an HPLC chromatogram of compound 17 in Example 1 of the present disclosure.
Figure 18:
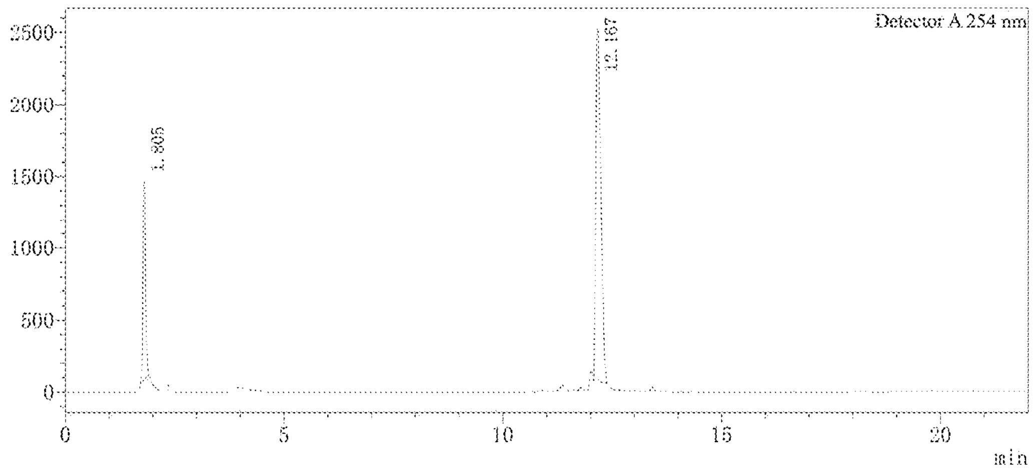
FIG. 18 is an HPLC chromatogram of a reaction system of compound 17 and compound 10 in Example 1 of the present disclosure.
Figure 19:
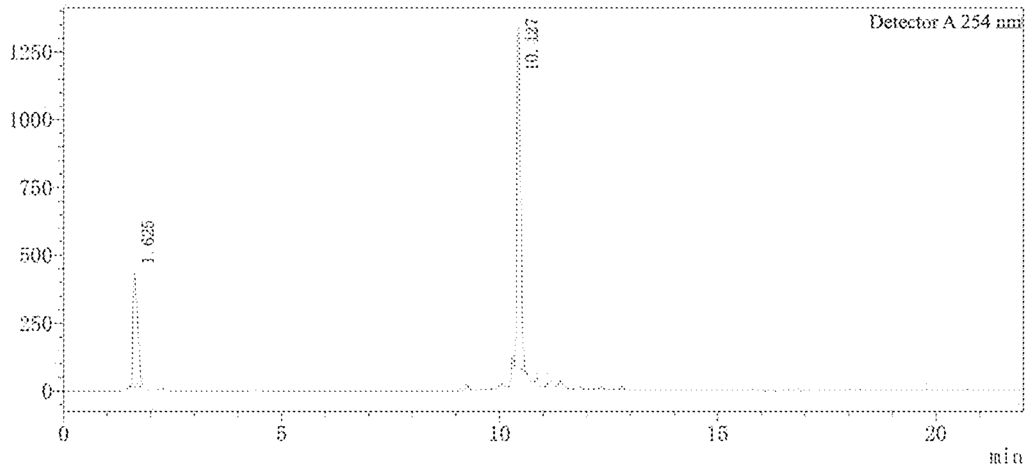
FIG. 19 is an HPLC chromatogram of compound 19 in Example 1 of the present disclosure.
Figure 20:
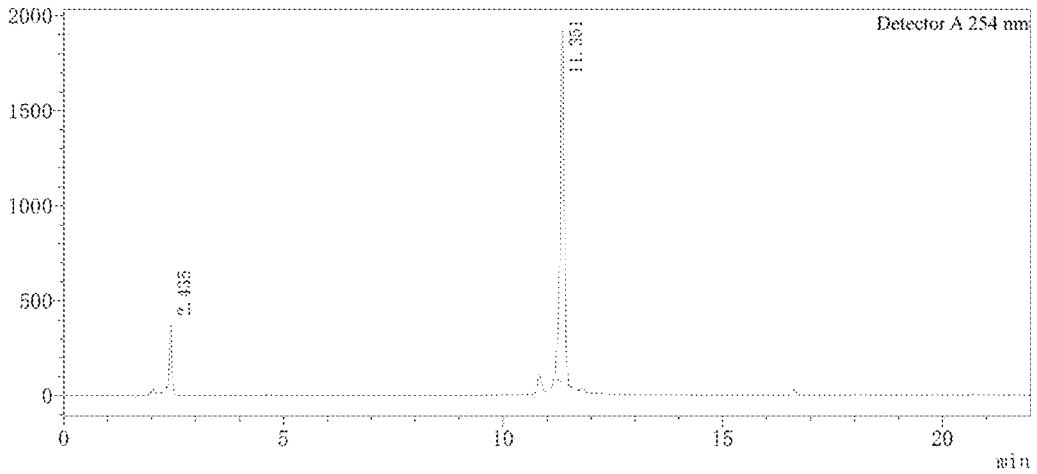
FIG. 20 is an HPLC chromatogram of a reaction system of compound 19 and DOTA-NHS in Example 1 of the present disclosure.

-continued
Formula (II-13)
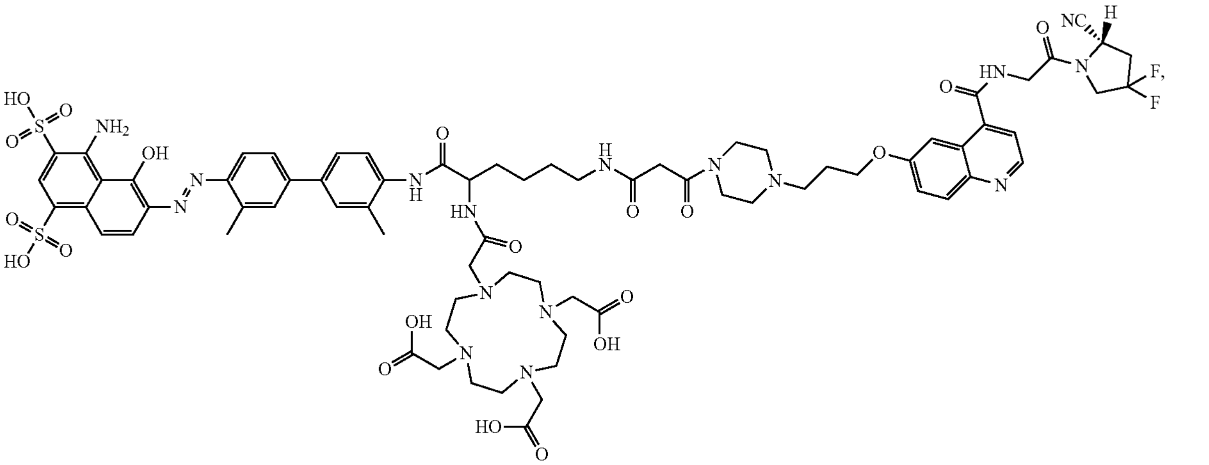
Formula (II-14)
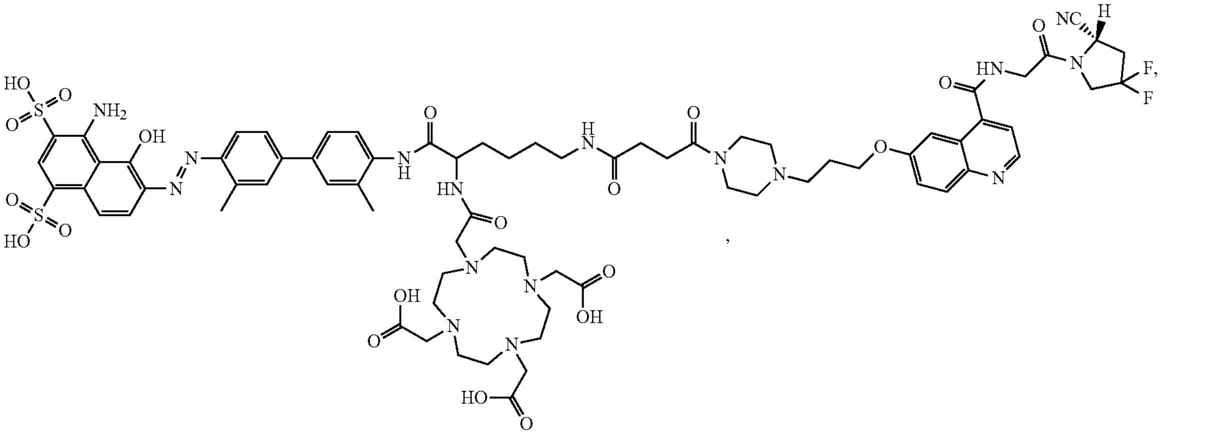
,
Formula (II-15)
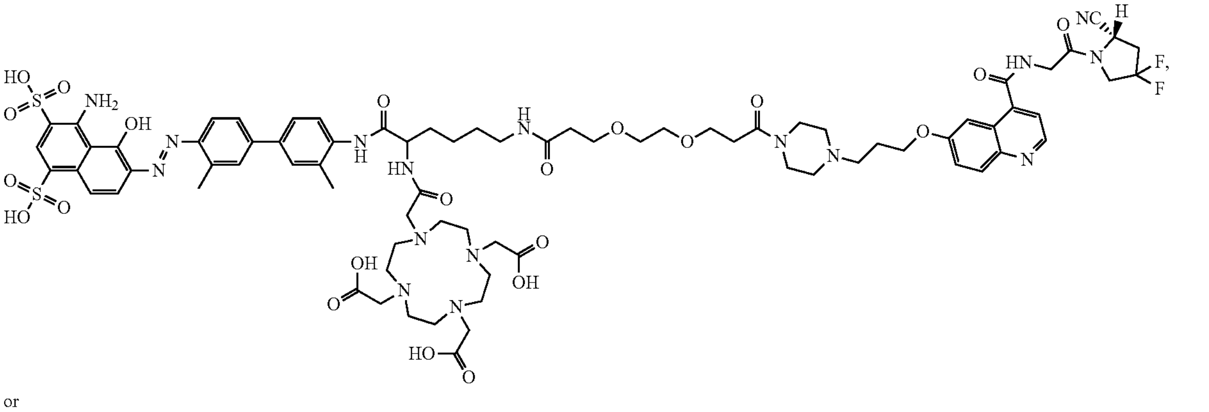
or -continued
Formula (II-16)
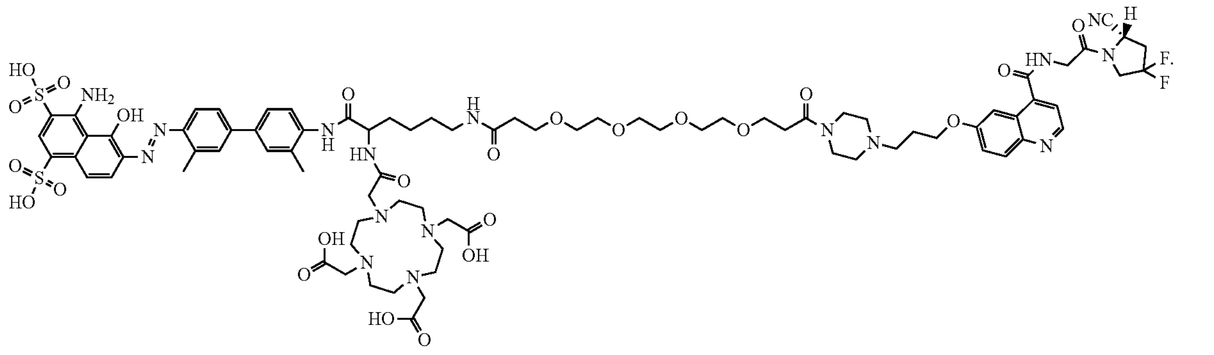
The mass spectrum of compound (11-10) in Example 10 is shown in FIG. 14. The mass spectrum of compound (II-11) in Example 11 is shown in FIG. 15.
Examples 17-Examples 38
With reference to the preparation methods in Examples 1-Examples 16, a tEB-FAPI compound shown in the following Formula (I) was prepared.
Formula (I)
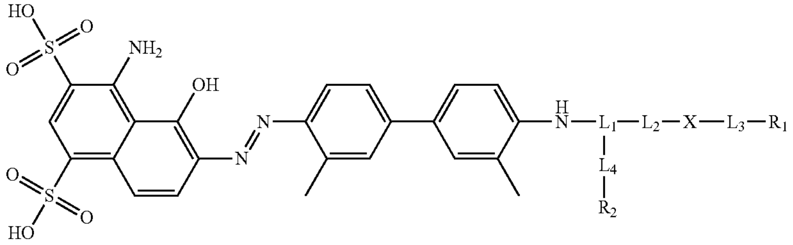
| Example | X | $L_1$ |
|---|---|---|
| 17 | 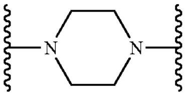 [SMILES: *N1CCN(*)CC1] | 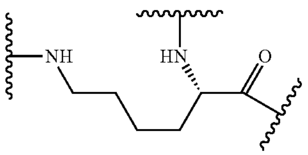 [SMILES: *NCCCC[C@H](N*)C(*)=O] |
| 18 | 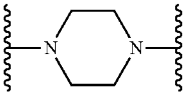 [SMILES: *N1CCN(*)CC1] | 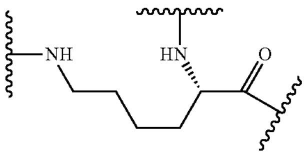 [SMILES: *NCCCC[C@H](N*)C(*)=O] |
| 19 | 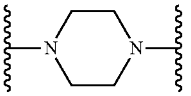 [SMILES: *N1CCN(*)CC1] | 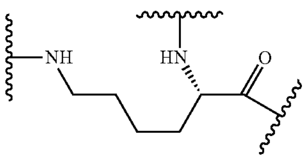 [SMILES: *NCCCC[C@H](N*)C(*)=O] |

-continued
| | | |
|---|---|---|
| 20 | 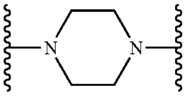 [SMILES: *N1CCN(*)CC1] | 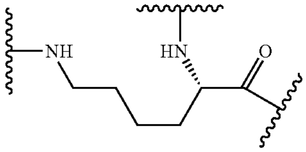 [SMILES: *NCCCC[C@H](N*)C(*)=O] |
| 21 | 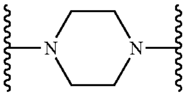 | 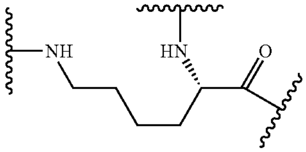 [SMILES: *NCCCC[C@H](N*)C(*)=O] |
| 22 | 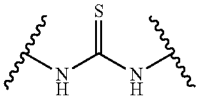 | 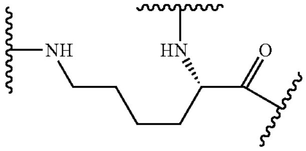 [SMILES: *NCCCC[C@H](N*)C(*)=O] |
| 23 | 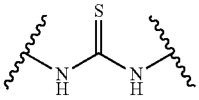 [SMILES: *NC(=S)N*] | 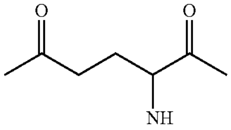 |
| 24 | 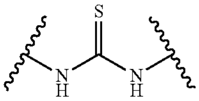 [SMILES: *NC(=S)N*] | 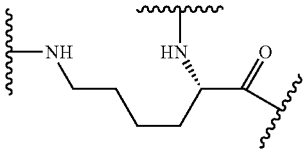 [SMILES: *NCCCC[C@H](N*)C(*)=O] |
| 25 | 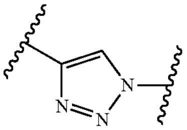 [SMILES: *c1cn(*)nn1] | 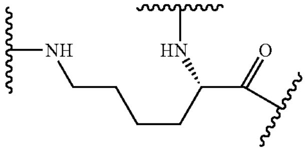 [SMILES: *NCCCC[C@H](N*)C(*)=O] |
| 26 | 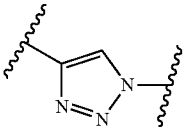 [SMILES: *c1cn(*)nn1] | 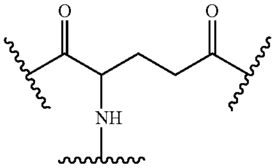 [SMILES: *NC(CCC(*)=O)C(*)=O] |
| 27 | 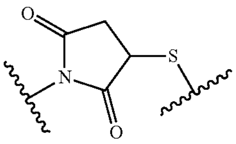 [SMILES: *SC1CC(=O)N(*)C1=O] | 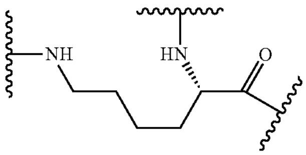 [SMILES: *NCCCC[C@H](N*)C(*)=O] |
| 28 | 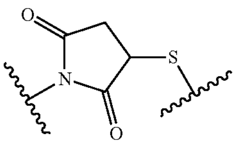 [SMILES: *SC1CC(=O)N(*)C1=O] | 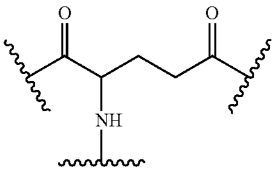 [SMILES: *NC(CCC(*)=O)C(*)=O] |
| 29 | N | 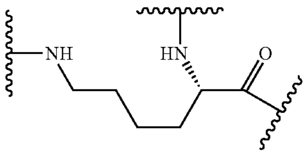 [SMILES: *NCCCC[C@H](N*)C(*)=O] |

-continued
| | | |
|---|---|---|
| 30 | S | 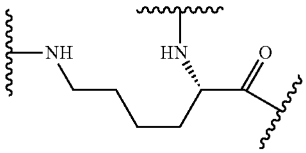 [SMILES: *NCCCC[C@H](N*)C(*)=O] |
| 31 | O | 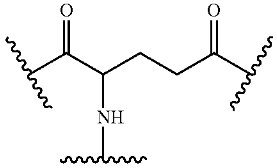 [SMILES: *NC(CCC(*)=O)C(*)=O] |
| 32 | C | 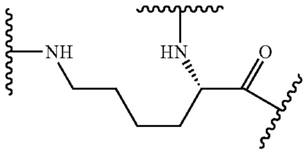 [SMILES: *NCCCC[C@H](N*)C(*)=O] |
| 33 | 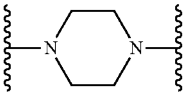 | 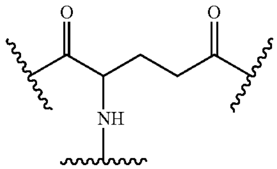 [SMILES: *NC(CCC(*)=O)C(*)=O] |
| 34 | 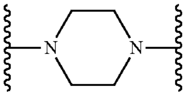 [SMILES: *N1CCN(*)CC1] | 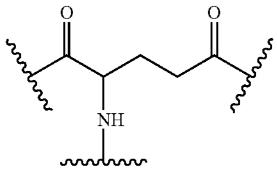 [SMILES: *NC(CCC(*)=O)C(*)=O] |
| 35 | 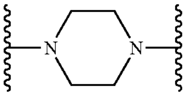 | 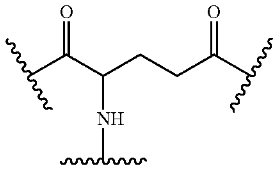 [SMILES: *NC(CCC(*)=O)C(*)=O] |
| 36 | 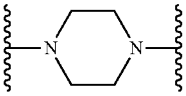 [SMILES: *N1CCN(*)CC1] | 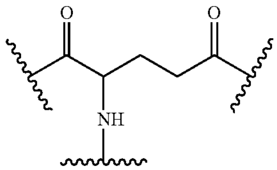 [SMILES: *NC(CCC(*)=O)C(*)=O] |
| 37 | 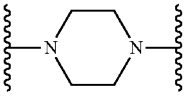 [SMILES: *N1CCN(*)CC1] | 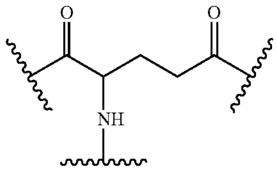 [SMILES: *NC(CCC(*)=O)C(*)=O] |
| 38 | 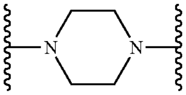 | 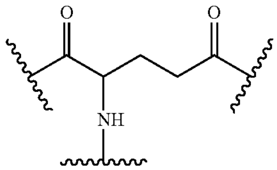 [SMILES: *NC(CCC(*)=O)C(*)=O] |

-continued
| Example | $L_2$ | $L_3$ |
|---|---|---|
| 17 | 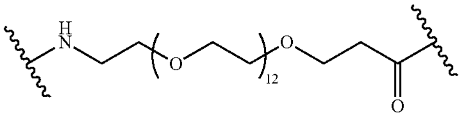 | 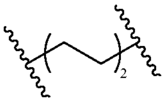 |
| 18 | 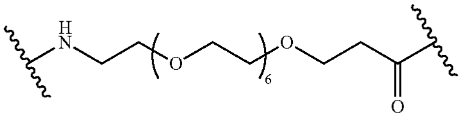 | 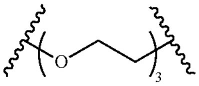 |
| 19 | 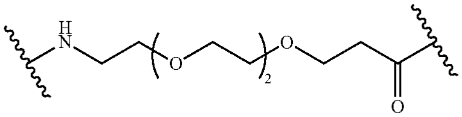 | 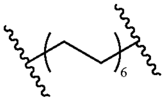 |
| 20 | 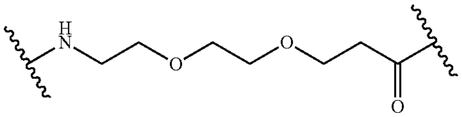 [SMILES: *NCCOCCOCCC(*)=O] | 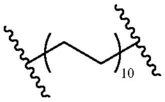 |
| 21 | 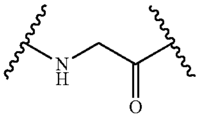 [SMILES: *NCC(*)=O] | 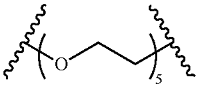 |
| 22 | 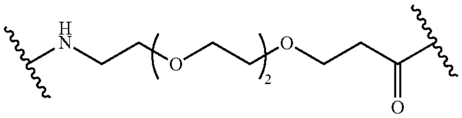 | 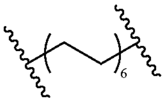 |
| 23 | 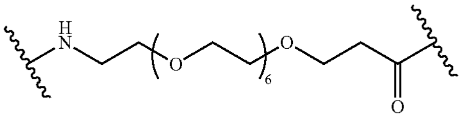 | 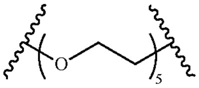 |
| 24 | 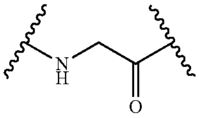 [SMILES: *NCC(*)=O] | 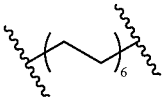 |
| 25 | 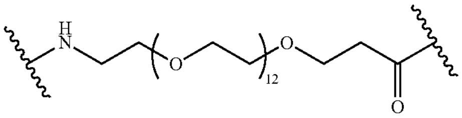 | 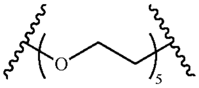 |
| 26 | 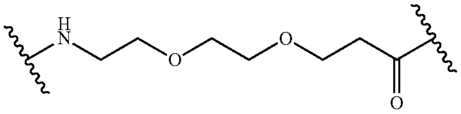 [SMILES: *NCCOCCOCCC(*)=O] | 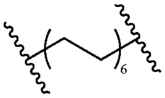 |
| 27 | 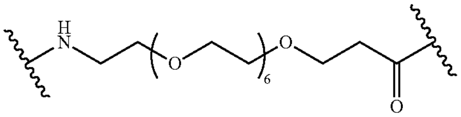 | 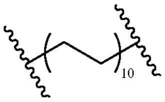 |

-continued
| | | |
|---|---|---|
| 28 | 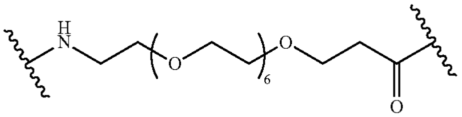 | 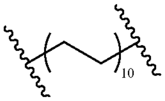 |
| 29 | — | — |
| 30 | 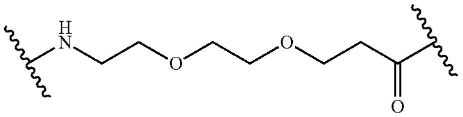 [SMILES: *NCCOCCOCCC(*)=O] | 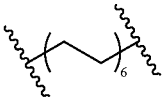 |
| 31 | 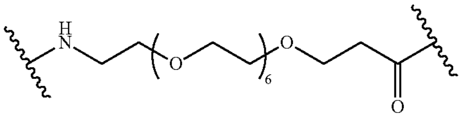 | 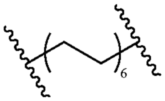 |
| 32 | 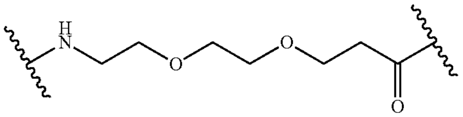 [SMILES: *NCCOCCOCCC(*)=O] | 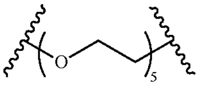 |
| 33 | — | 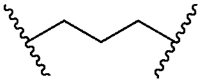 |
| 34 | 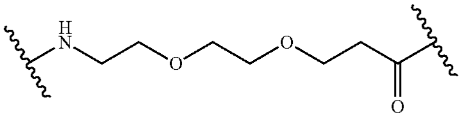 [SMILES: *NCCOCCOCCC(*)=O] | 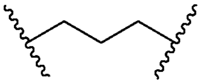 [SMILES: *CCC*] |
| 35 | 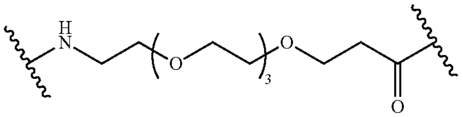 | 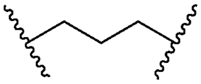 [SMILES: *CCC*] |
| 36 | — | 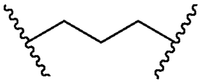 [SMILES: *CCC*] |
| 37 | 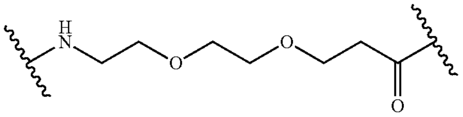 [SMILES: *NCCOCCOCCC(*)=O] | 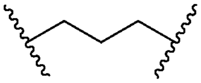 [SMILES: *CCC*] |
| 38 | 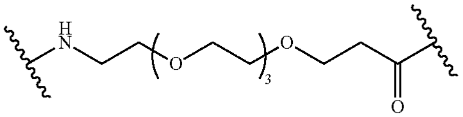 | 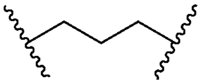 [SMILES: *CCC*] |
| Ex-am-ple | $L_4$ | $R_1$ |
|---|---|---|
| 17 | 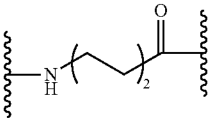 | 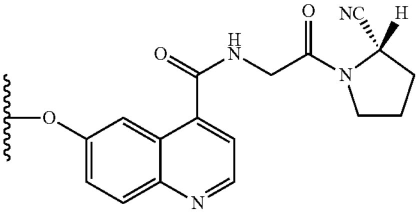 [SMILES: *Oc1ccc2nccc(C(=O)NCC(=O)N3CCC[C@H]3C#N)c2c1] |

-continued
| | | |
|---|---|---|
| 18 | 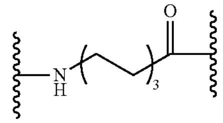 | 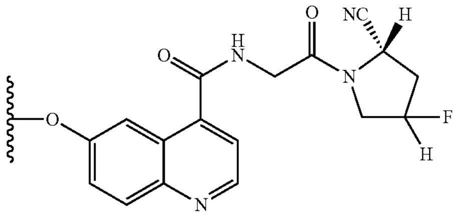 [SMILES: *Oc1ccc2nccc(C(=O)NCC(=O)N3CC(F)C[C@H]3C#N)c2c1] |
| 19 | 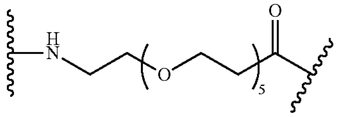 | 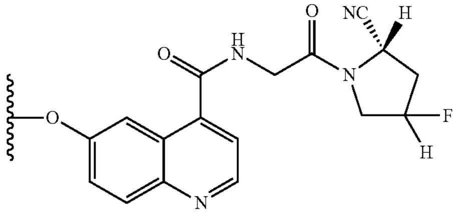 |
| 20 | 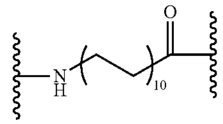 | 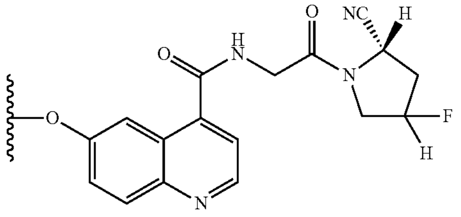 [SMILES: *Oc1ccc2nccc(C(=O)NCC(=O)N3CC(F)C[C@H]3C#N)c2c1] |
| 21 | 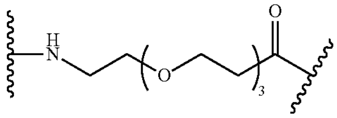 | 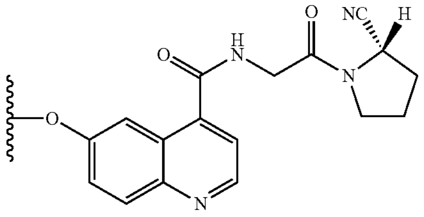 [SMILES: *Oc1ccc2nccc(C(=O)NCC(=O)N3CCC[C@H]3C#N)c2c1] |
| 22 | 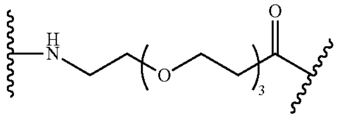 | 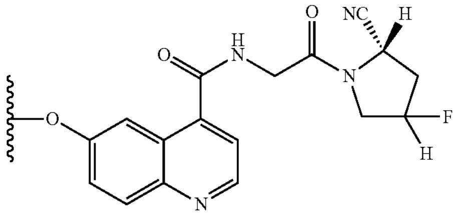 [SMILES: *Oc1ccc2nccc(C(=O)NCC(=O)N3CC(F)C[C@H]3C#N)c2c1] |
| 23 | 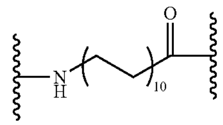 | 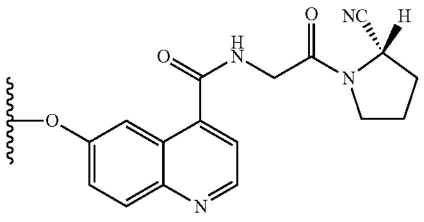 [SMILES: *Oc1ccc2nccc(C(=O)NCC(=O)N3CCC[C@H]3C#N)c2c1] |
| 24 | 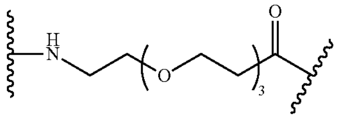 | 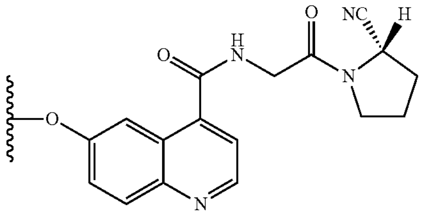 [SMILES: *Oc1ccc2nccc(C(=O)NCC(=O)N3CCC[C@H]3C#N)c2c1] |

-continued
| | | |
|---|---|---|
| 25 | 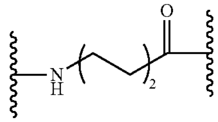 | 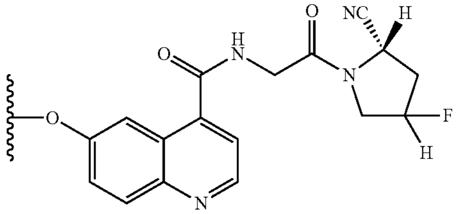 [SMILES: *Oc1ccc2nccc(C(=O)NCC(=O)N3CC(F)C[C@H]3C#N)c2c1] |
| 26 | 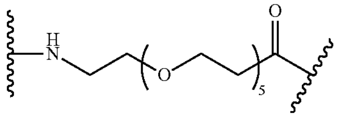 | 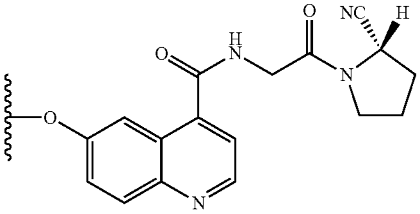 [SMILES: *Oc1ccc2nccc(C(=O)NCC(=O)N3CCC[C@H]3C#N)c2c1] |
| 27 | 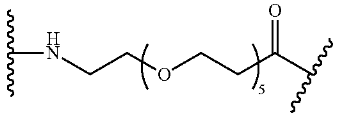 | 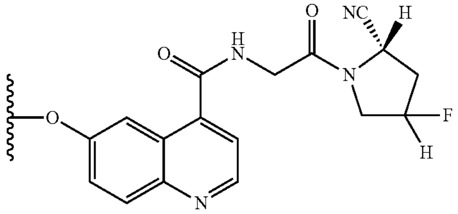 |
| 28 | 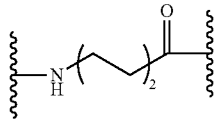 | 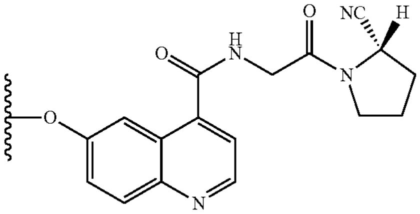 [SMILES: *Oc1ccc2nccc(C(=O)NCC(=O)N3CCC[C@H]3C#N)c2c1] |
| 29 | — | 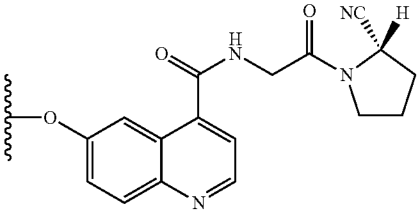 [SMILES: *Oc1ccc2nccc(C(=O)NCC(=O)N3CCC[C@H]3C#N)c2c1] |
| 30 | 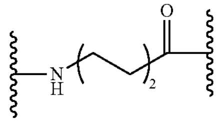 | 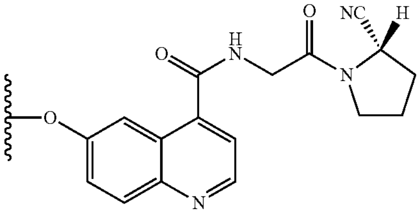 [SMILES: *Oc1ccc2nccc(C(=O)NCC(=O)N3CCC[C@H]3C#N)c2c1] |
| 31 | 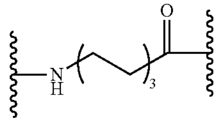 | 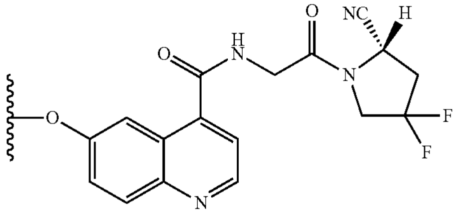 [SMILES: *Oc1ccc2nccc(C(=O)NCC(=O)N3CC(F)(F)C[C@H]3C#N)c2c1] |

-continued
| | | |
|---|---|---|
| 32 | 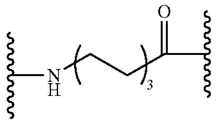 | 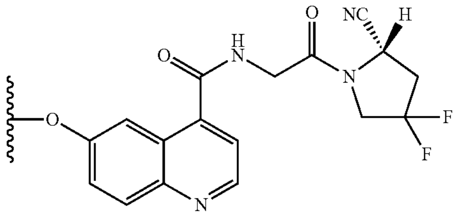 [SMILES: *Oc1ccc2nccc(C(=O)NCC(=O)N3CC(F)(F)C[C@H]3C#N)c2c1] |
| 33 | — | 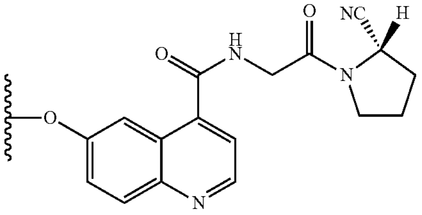 [SMILES: *Oc1ccc2nccc(C(=O)NCC(=O)N3CCC[C@H]3C#N)c2c1] |
| 34 | — | 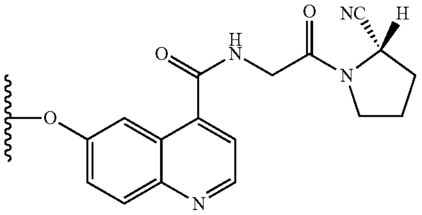 [SMILES: *Oc1ccc2nccc(C(=O)NCC(=O)N3CCC[C@H]3C#N)c2c1] |
| 35 | — | 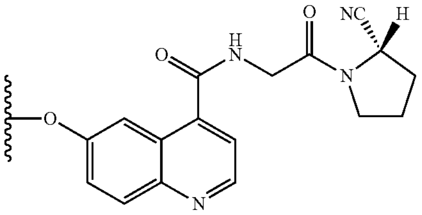 [SMILES: *Oc1ccc2nccc(C(=O)NCC(=O)N3CCC[C@H]3C#N)c2c1] |
| 36 | — | 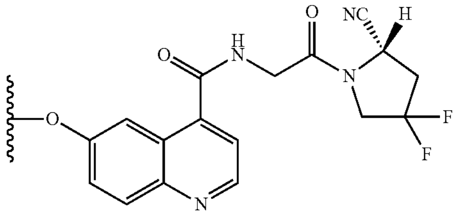 |
| 37 | — | 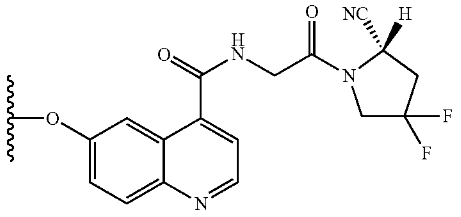 |
| 38 | — | 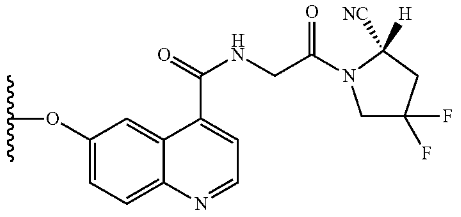 [SMILES: *Oc1ccc2nccc(C(=O)NCC(=O)N3CC(F)(F)C[C@H]3C#N)c2c1] |

-continued
| Example | $R_2$ |
|---|---|
| 17 | 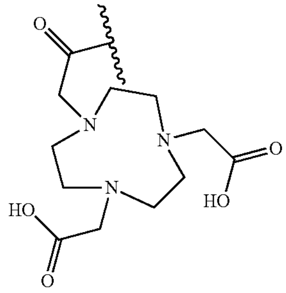 [SMILES: *C(=O)CN1CCN(CC(=O)O)CCN(CC(=O)O)CC1] |
| 18 | 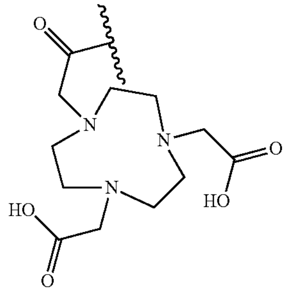 [SMILES: *C(=O)CN1CCN(CC(=O)O)CCN(CC(=O)O)CC1] |
| 19 | 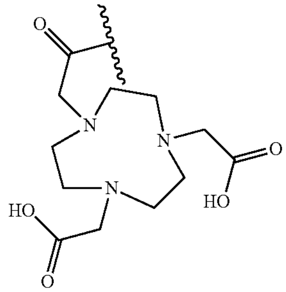 [SMILES: *C(=O)CN1CCN(CC(=O)O)CCN(CC(=O)O)CC1] |
| 20 | 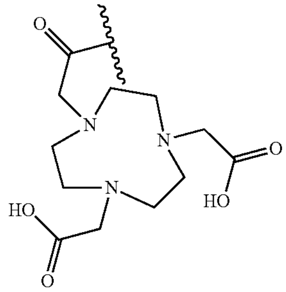 [SMILES: *C(=O)CN1CCN(CC(=O)O)CCN(CC(=O)O)CC1] |
| 21 | 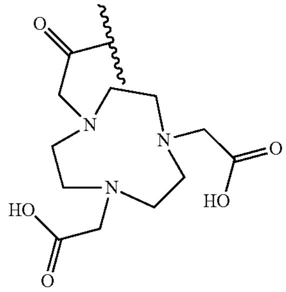 [SMILES: *C(=O)CN1CCN(CC(=O)O)CCN(CC(=O)O)CC1] |

-continued
22
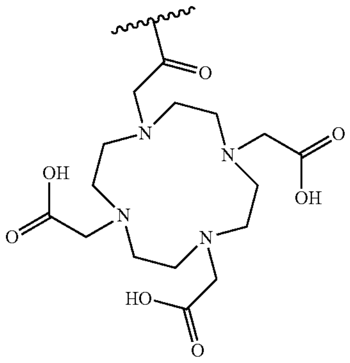 [SMILES: *C(=O)CN1CCN(CC(=O)O)CCN(CC(=O)O)CCN(CC(=O)O)CC1]
23
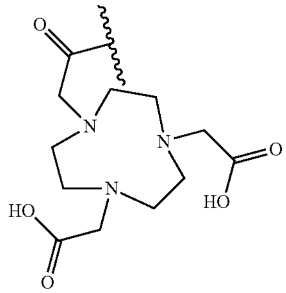 [SMILES: *C(=O)CN1CCN(CC(=O)O)CCN(CC(=O)O)CC1]
24
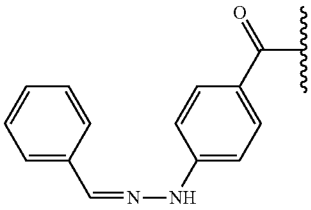 [SMILES: *C(=O)c1ccc(NN=Cc2ccccc2)cc1]
25
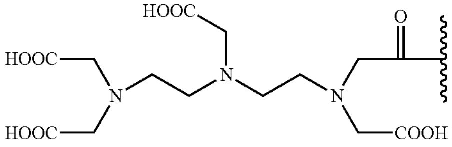 [SMILES: *C(=O)CN(CCN(CCN(CC(=O)O)CC(=O)O)CC(=O)O)CC(=O)O]
26
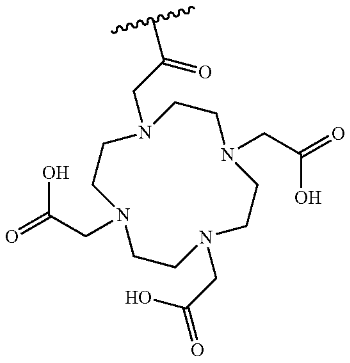 [SMILES: *C(=O)CN1CCN(CC(=O)O)CCN(CC(=O)O)CCN(CC(=O)O)CC1]

-continued
27
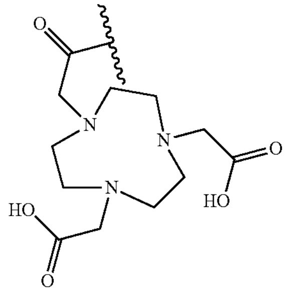 [SMILES: *C(=O)CN1CCN(CC(=O)O)CCN(CC(=O)O)CC1]
28
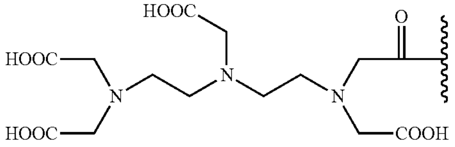 [SMILES: *C(=O)CN(CCN(CCN(CC(=O)O)CC(=O)O)CC(=O)O)CC(=O)O]
29
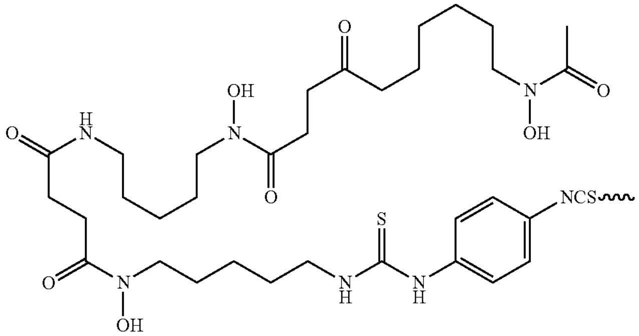
30
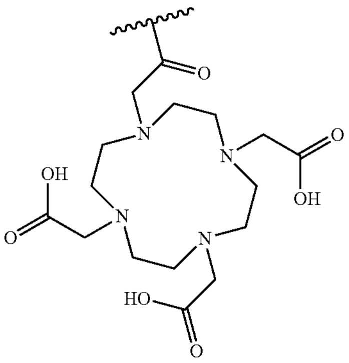 [SMILES: *C(=O)CN1CCN(CC(=O)O)CCN(CC(=O)O)CCN(CC(=O)O)CC1]
31
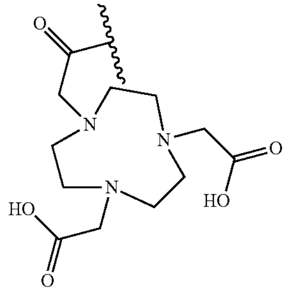 [SMILES: *C(=O)CN1CCN(CC(=O)O)CCN(CC(=O)O)CC1]
32
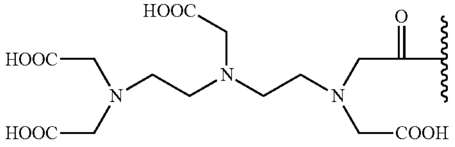 [SMILES: *C(=O)CN(CCN(CCN(CC(=O)O)CC(=O)O)CC(=O)O)CC(=O)O]

-continued
33
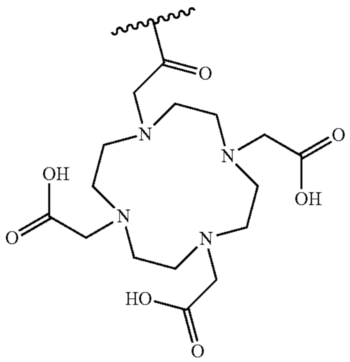 [SMILES: *C(=O)CN1CCN(CC(=O)O)CCN(CC(=O)O)CCN(CC(=O)O)CC1]
34
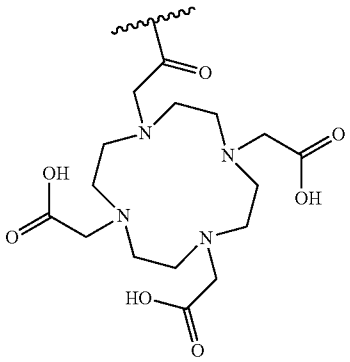 [SMILES: *C(=O)CN1CCN(CC(=O)O)CCN(CC(=O)O)CCN(CC(=O)O)CC1]
35
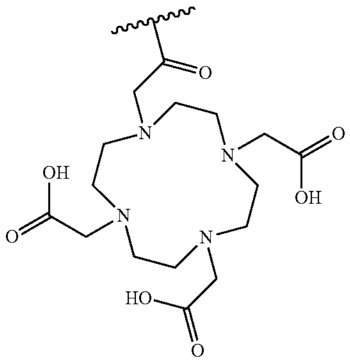 [SMILES: *C(=O)CN1CCN(CC(=O)O)CCN(CC(=O)O)CCN(CC(=O)O)CC1]
36
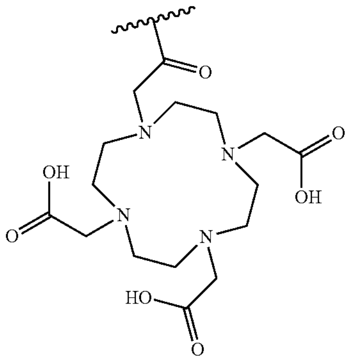 [SMILES: *C(=O)CN1CCN(CC(=O)O)CCN(CC(=O)O)CCN(CC(=O)O)CC1]

-continued

37

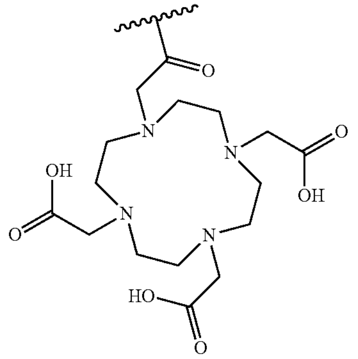 [SMILES: *C(=O)CN1CCN(CC(=O)O)CCN(CC(=O)O)CCN(CC(=O)O)CC1]

38

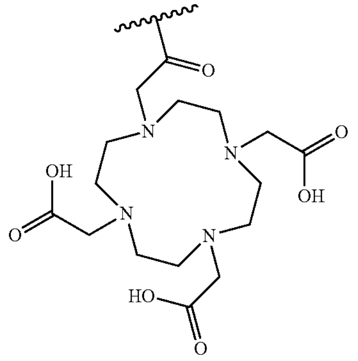 [SMILES: *C(=O)CN1CCN(CC(=O)O)CCN(CC(=O)O)CCN(CC(=O)O)CC1]

Example 39: Preparation of a Radioactive $^{68}$Ga Labeled tEB-FAPI Complex

Wet method: A hydrochloric acid solution of about 18.5-1,850 MBq of $^{68}GaCl_3$ (rinsed from a germanium-gallium generator) was added to an acetic acid-acetate solution (1.0 g/L) containing 0.5 mL of compound 20 prepared in Example 1 in a centrifuge tube, and the reaction was carried out at 37° C. for 20 min. A small C18 separation column was slowly rinsed with 10 mL of anhydrous ethanol first, and then rinsed with 10 mL of water. A resulting labeled solution was diluted with 10 mL of water, and then sampled to the separation column. Unlabeled $^{68}$Ga ions were removed with 10 mL of water, and rinsing was conducted with 0.3 mL of a 10 mM ethanol solution of HCl to obtain $^{68}$Ga labeled tEB-FAPI complex. The rinsed solution was diluted with normal saline, followed by aseptic filtration to obtain an injection of the $^{68}$Ga labeled tEB-FAPI complex.

Freeze-drying method: A hydrochloric acid solution of about 18.5-1,850 MBq of $^{68}GaCl_3$ (rinsed with a germanium-gallium generator) was added to a freeze-dried medicine box containing the compound 20, and uniformly mixed for a reaction at 37° C. for 20 min. A small C18 separation column was slowly rinsed with 10 mL of anhydrous ethanol first, and then rinsed with 10 mL of water. A resulting labeled solution was diluted with 10 mL of water, and then sampled to the separation column. Unlabeled $^{68}$Ga ions were removed with 10 mL of water, and rinsing was conducted with 0.3 mL of a 10 mM ethanol solution of HCl to obtain a rinsed solution of a complex. The rinsed solution was diluted with normal saline, followed by aseptic filtration to obtain an injection of the $^{68}$Ga labeled tEB-FAPI complex.

Example 40: Preparation of a $^{177}$Lu Labeled tEB-FAPI Complex

Wet method: A sodium acetate solution of about 18.5-1,850 MBq of $^{177}LuCl_3$ was separately added to an acetic acid-acetate solution (1.0 g/L) containing 0.5 mL of compound 20 in Example 1, the compound (Formula (II-2)) in Example 2 and the compound (Formula (II-3)) in Example 3 in three centrifuge tubes, and reaction was carried out at 90° C. for 20 min. A small C18 separation column was slowly rinsed with 10 mL of anhydrous ethanol first, and then rinsed with 10 mL of water. Resulting labeled solution was diluted with 10 mL of water, and then sampled to the separation column. Unlabeled $^{177}$Lu ions were removed with 10 mL of water, and rinsing was conducted with 0.3 mL of a 10 mM ethanol solution of HCl to obtain three $^{177}$Lu labeled tEB-FAPI complexes. The rinsed solutions were diluted with normal saline, followed by aseptic filtration to obtain injections of the three $^{177}$Lu labeled tEB-FAPI complexes.

Freeze-drying method: A sodium acetate solution of about 18.5-1,850 MBq of $^{177}LuCl_3$ was separately added to three freeze-dried medicine boxes containing compound 20 in Example 1, the compound (Formula (II-2)) in Example 2 and the compound (Formula (II-3)) in Example 3, and uniformly mixed for reactions at 90° C. for 20 min. A small C18 separation column was taken, slowly rinsed with 10 mL of anhydrous ethanol first, and then rinsed with 10 mL of water. Resulting labeled solutions were diluted with 10 mL of water, and then sampled to the separation column. Unlabeled $^{177}$Lu ions were removed with 10 mL of water, and rinsing was conducted with 0.3 mL of a 10 mM ethanol solution of HCl to obtain rinsed solutions of three $^{177}$Lu labeled tEB-FAPI complexes. The rinsed solutions were diluted with normal saline, followed by aseptic filtration to obtain injections of the three $^{177}$Lu labeled tEB-FAPI complexes.

Experimental Example: Analysis and Application Effect

1. HPLC Analysis and Identification

An HPLC system was as follows: SHIMADZULC-20A; and a C18 chromatographic column (YMC, 3 μm, 4.6*150 mm) was used for analysis. Detection was conducted at a wavelength of 254 nm and a flow rate of 1 mL/min according to the following rinsing gradient: at 0-3 min, 10% of acetonitrile and 90% of water (50 mM ammonium acetate) were remained unchanged; at 3-16 min, the system was increased to include 90% of acetonitrile and 10% of water (50 mM ammonium acetate); at 16-18 min, 90% of acetonitrile and 10% of water (50 mM ammonium acetate) were remained; at 18-20 min, the system was reduced to include 10% of acetonitrile and 90% of water (50 mM ammonium acetate); and at 20-22 min, 10% of acetonitrile and 90% of water (50 mM ammonium acetate) were retained.

Compound 10, compound 17, a reaction system of compound 10 and compound 17, compound 19 and a reaction system of compound 19 and DOTA-NHS in Example 1 were identified and analyzed according to the above system. Results obtained are shown in FIG. 16 to FIG. 20.

The two radiolabeled probes prepared in Example 39 and Example 40 were used as experimental agents below, and determination of properties of the probes is described as follows.

Figure 21A:
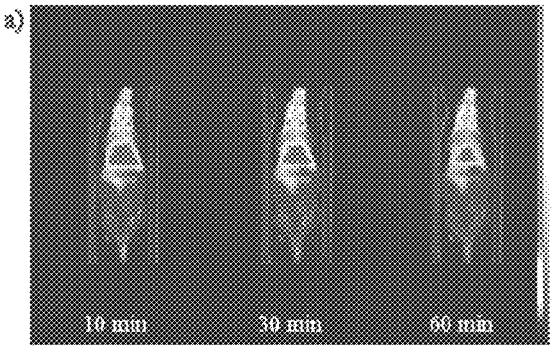
FIG. 21A and FIG. 21B show MicroPET imaging of a $^{68}$Ga labeled tEB-FAPI complex of the present disclosure and $^{68}$Ga labeled FAPI-02 in normal mice.
Figure 21B:
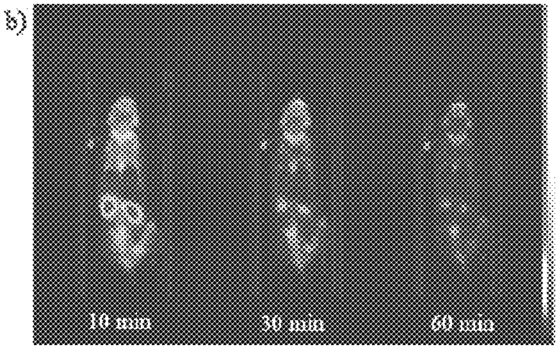

2. MicroPET Imaging of a $^{68}$Ga Labeled tEB-FAPI Complex in Normal Mice $^{68}$Ga-tEB-FAPI with a purity of greater than 95% was prepared by the method in Example 39. 3.7 MBq of the $^{68}$Ga-tEB-FAPI or $^{68}$Ga-FAPI-02 (as a control) was intravenously injected into tails of normal FVB mice anesthetized with isoflurane. Then MicroPET imaging was conducted after administration for 0-120 min. Results are shown in FIG. 21A and FIG. 21B. The results show that the $^{68}$Ga-tEB-FAPI complex in Example 39 has higher uptake in the cardiac blood pool of the mice (FIG. 21A), while the $^{68}$Ga-FAPI-02 is almost completely cleared in the test period (FIG. 21B), indicating that the half-life in blood circulation can be obviously prolonged by introducing truncated Evans Blue.

Figure 22:
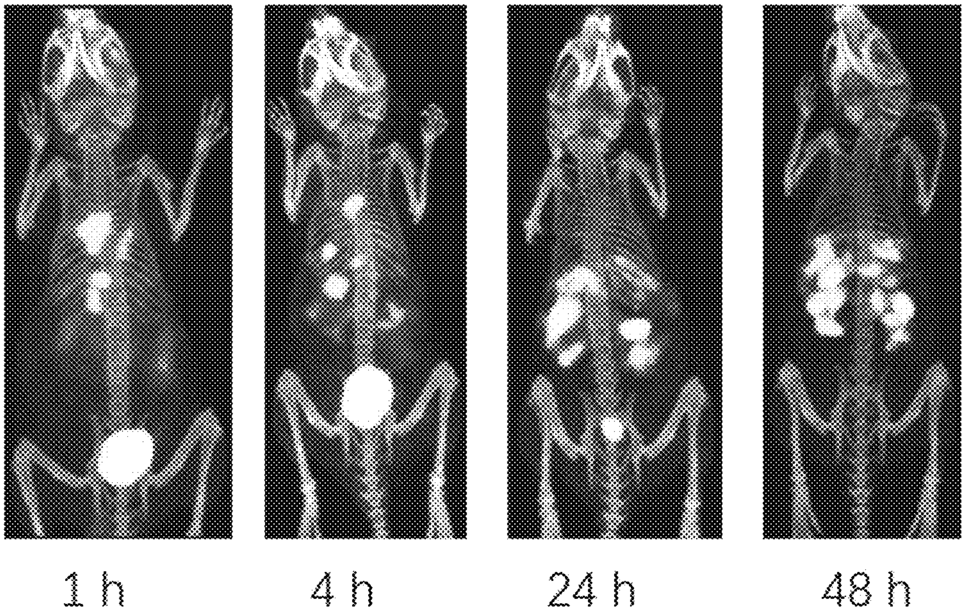
FIG. 22 shows SPECT imaging of $^{177}$Lu-tEB-FAPI prepared in Example 40 of the present disclosure in normal mice at different time points.
Figure 23:
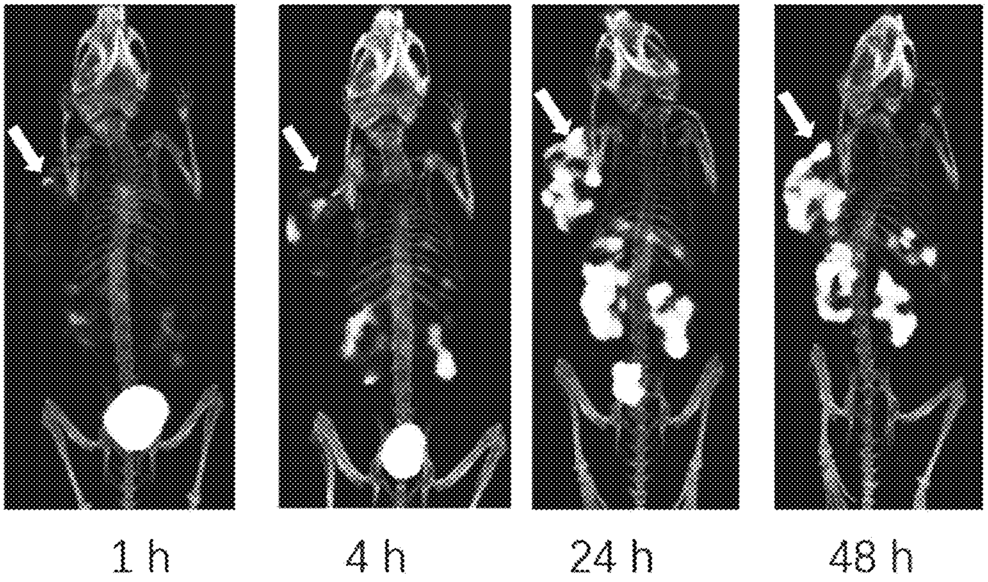
FIG. 23 shows SPECT imaging of $^{177}$Lu-tEB-FAPI prepared in Example 40 of the present disclosure in xenograft model mice with human pancreatic cancer at different time points.

3. Uptake Experiment of a $^{177}$Lu Labeled tEB-FAPI Complex in Tumors in Xenograft Model Mice with Human Pancreatic Cancer $^{177}$Lu-tEB-FAPI with a purity of greater than 95% was prepared by the method in Example 40. 1.3 MBq of the $^{177}$Lu-tEB-FAPI was intravenously injected into tails of normal mice and xenograft model mice with human pancreatic cancer separately. SPECT imaging was conducted at different time points after injection. Results are shown in FIG. 22 and FIG. 23. The results show that the $^{177}$Lu-tEB-FAPI has good pharmacokinetics in the normal mice, and can be continuously taken up by tumor tissues in the xenograft model mice with human pancreatic cancer and maintained for more than 48 h, indicating that the tEB-FAPI has the characteristics of significantly improving the uptake in tumors and prolonging the retention time, and can be used as a therapeutic agent and an imaging agent for tumors.

In summary, the truncated Evans Blue modified fibroblast activation protein inhibitor provided by the present disclosure can significantly prolong the half-life in blood circulation, improve the uptake and accumulation in tumors and prolong the tumor retention. Such novel properties are not available to other FAPI imaging agents. According to further preclinical animal level studies and clinical studies, it is proven that the inhibitor is expected to be used in radionuclide therapy and imaging of tumors with high expression of FAP.

Although the present disclosure has been described in detail by general descriptions, specific embodiments and tests above, it is obvious to persons skilled in the field that some modifications or improvements can be made on the basis of the present disclosure. Therefore, all the modifications or improvements made without departing from the spirit of the present disclosure shall fall within the protection scope of the present disclosure.

The invention claimed is:

1. A truncated Evans Blue modified fibroblast activation protein inhibitor compound or a pharmaceutically available salt thereof, wherein the molecular structure of the compound has the following structures shown in Formula (II-1):

Formula (II-1)

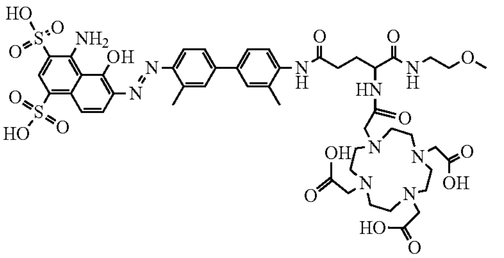

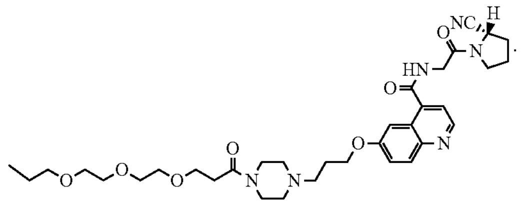

2. A truncated Evans Blue modified fibroblast activation protein inhibitor compound or a pharmaceutically available salt thereof, wherein the molecular structure of the compound has any one of the following structures shown in Formula (II-2) to Formula (II-8):

Formula (II-2)
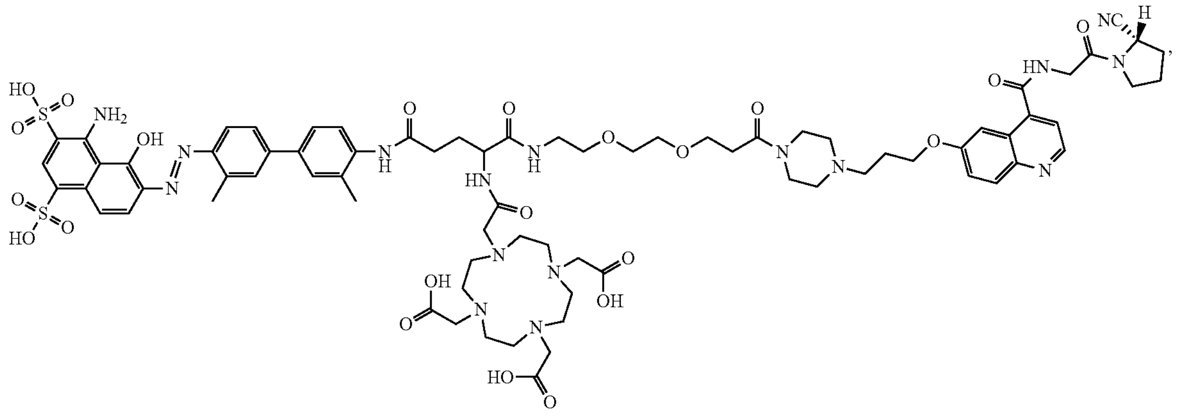
Formula (II-3)
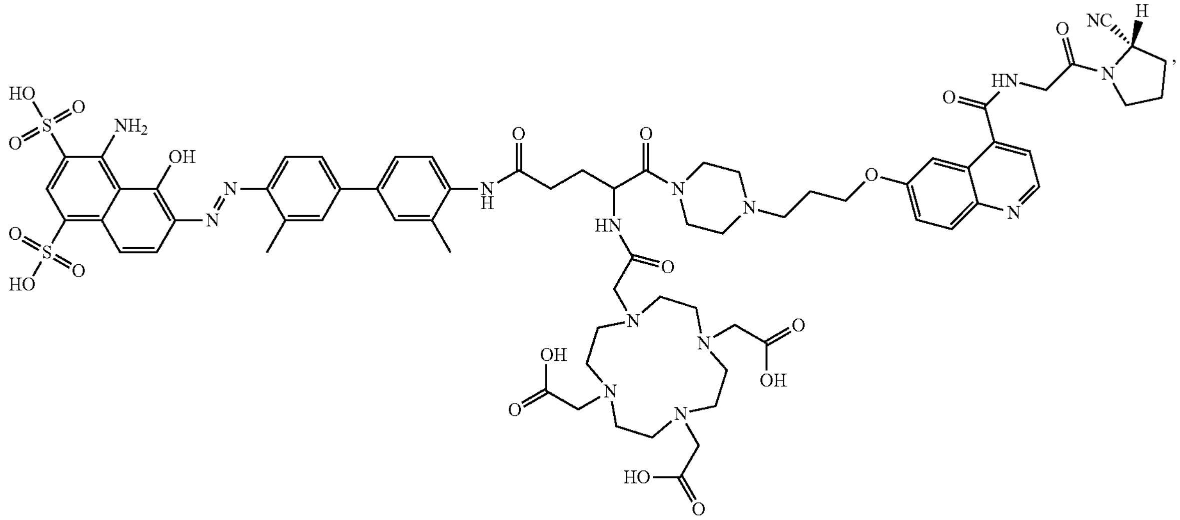
Formula (II-4)
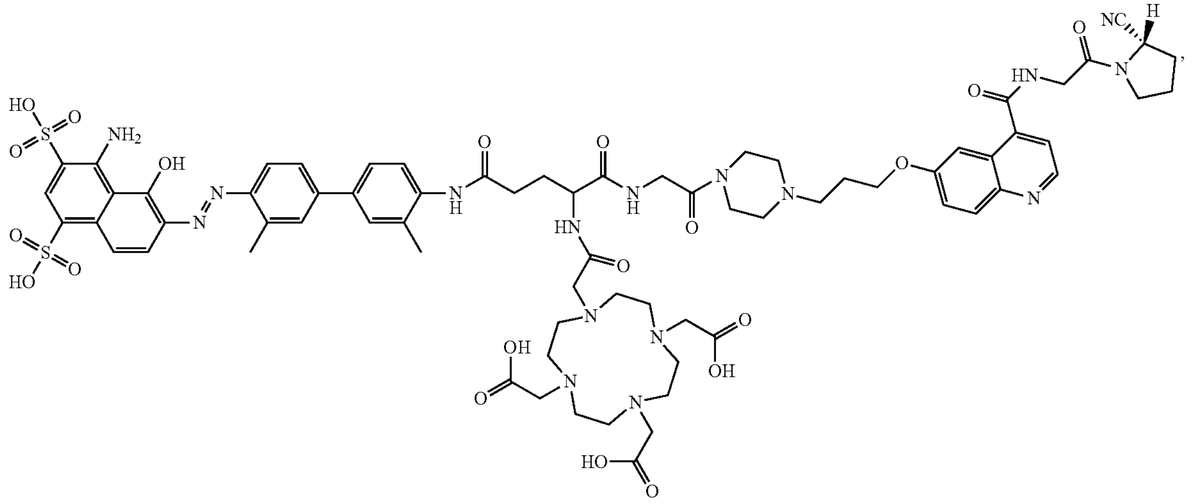

-continued
Formula (II-5)
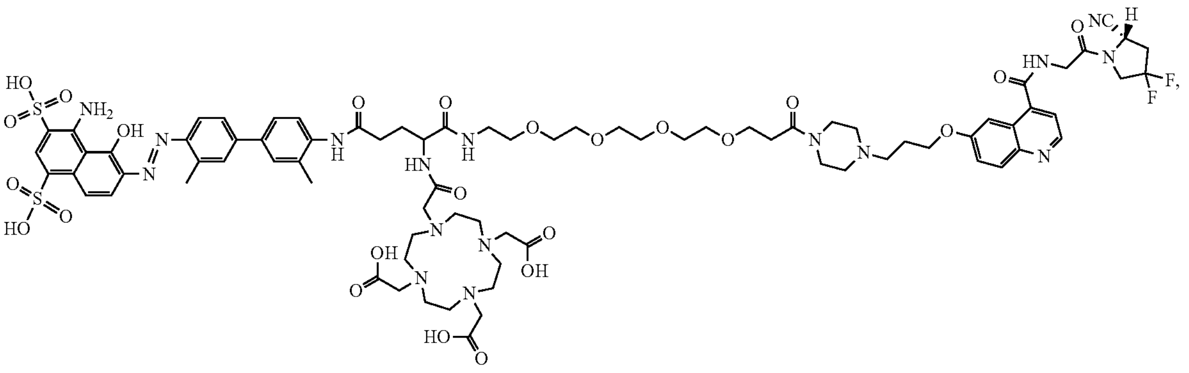
Formula (II-6)
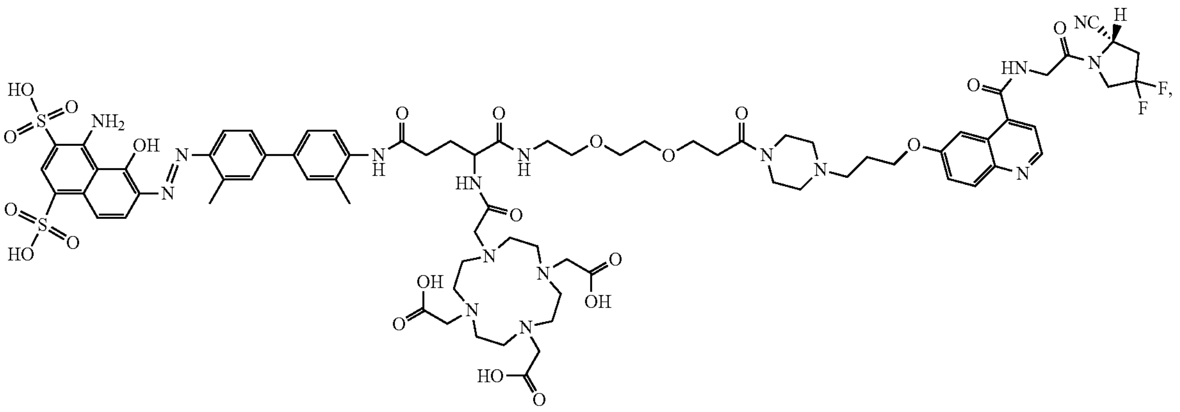
Formula (II-7)
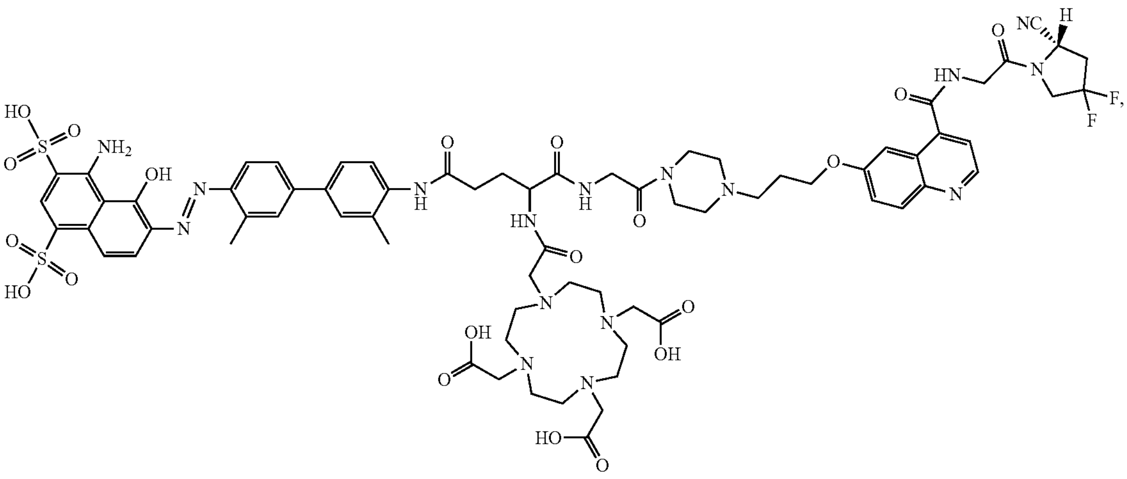
or -continued Formula (II-8)

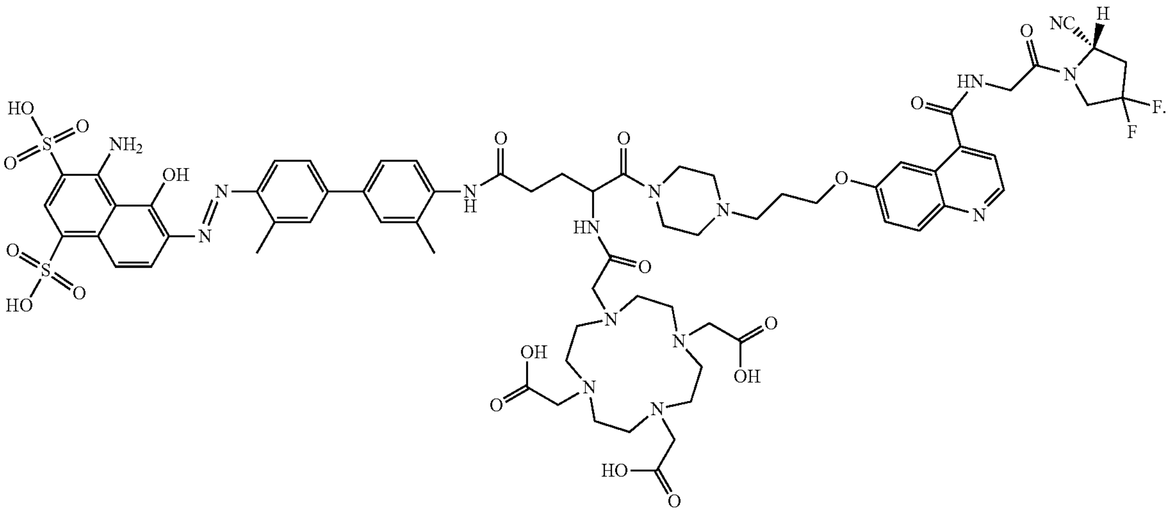

3. A method for preparing a truncated Evans Blue modified fibroblast activation protein inhibitor, comprising the following steps:

(1) reacting 6-hydroxy-4-quinolinecarboxylic acid with tert-butyl glycinate by amide condensation, followed by reactions with 1-bromo-3-chloropropane and tert-butyl 1-piperazinecarboxylate in sequence; then, removing Boc and tert-butyl protective groups under the action of TFA, and introducing a Boc protective group to amino, followed by an amide condensation reaction with (S)-pyrrolidene-2-carbonitrile hydrochloride; then, removing the Boc protective group using p-toluenesulfonic acid, followed by a condensation reaction with 5,8,11,14-tetraoxa-2-azaheptadecanedioic acid-1-tert-butyl ester; and removing the Boc protective group again under the action of p-toluenesulfonic acid to obtain an intermediate compound A:

compound A

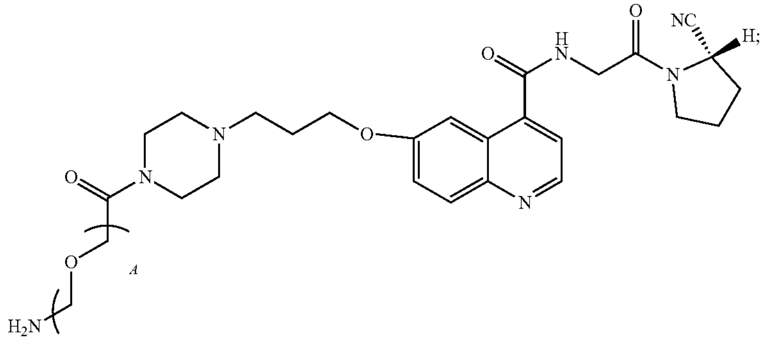

(2) introducing a Boc protective group to one end of 4,4'-diamino-3,3'-dimethyl biphenyl, followed by a reaction with monosodium 1-amino-8-naphthol-2,4-disulfonate to prepare a truncated Evans Blue derivative; removing the Boc protective group, followed by an amide condensation reaction with N-tert-butyloxycarbonyl-L-glutamic acid-1-tert-butyl ester; then, removing Boc and tert-butyl protective groups under the action of TFA; and then carrying out a reaction with di-tert-butyl dicarbonate, and introducing a Boc protective group to amino to obtain an intermediate compound B:

compound B

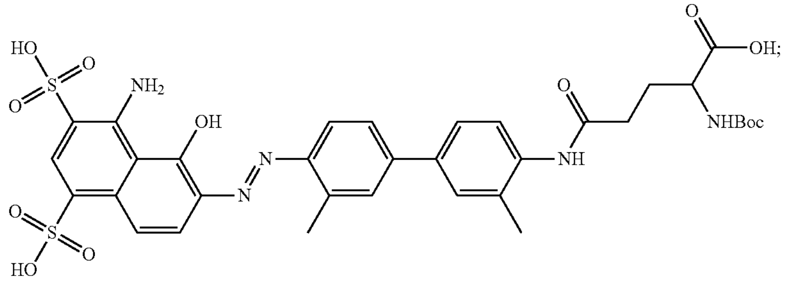

and (3) reacting the intermediate compound A obtained in step (1) with the intermediate compound B obtained in step (2) by amide condensation; then removing the Boc protective group using p-toluenesulfonic acid; and finally, carrying out a reaction with DOTA-NHS to obtain a truncated Evans Blue modified fibroblast activation protein inhibitor compound having the following structure shown in Formula (II-1)

Formula (II-1)

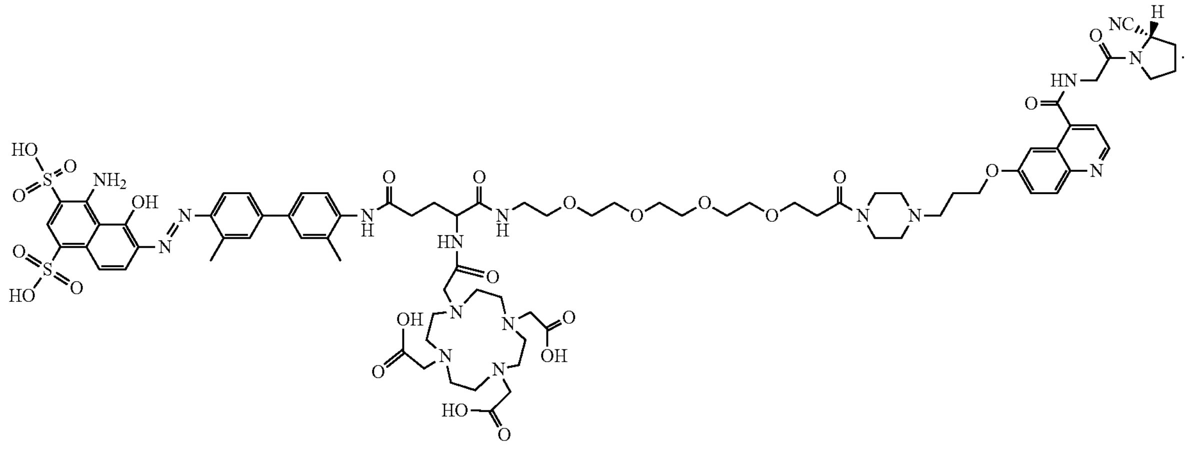

4. A radiolabeled complex of truncated Evans Blue modified Fibroblast activation protein inhibitor, having the following structure shown in Formula (IV):

Formula (IV)

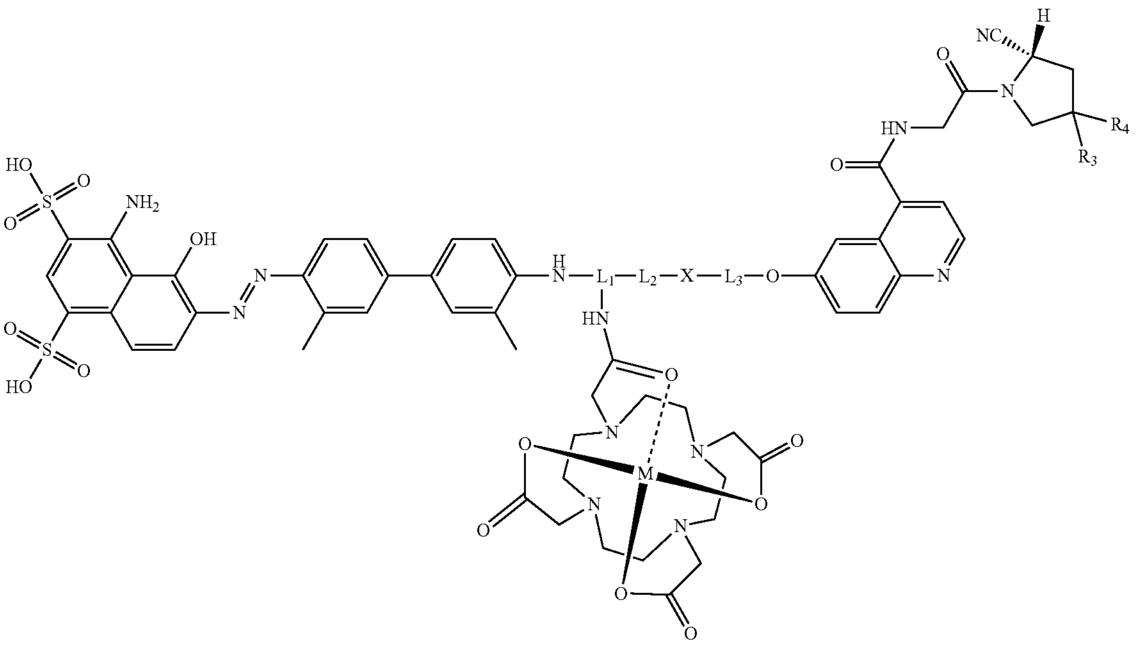

wherein $L_1$ is a glutamic acid structure;

$L_2$ is —$(CH_2)_0$—, —NH—$CH_2$—(CO)—, —NH—$CH_2$—$(CH_2OCH_2)_2$—$CH_2$—(CO)—, —NH—$CH_2$—$(CH_2OCH_2)_3$—$CH_2$(CO)—;

$L_3$ is —$(CH_2)_3$—;

X is

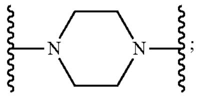 [SMILES: *N1CCN(*)CC1];

$R_3$ and $R_4$ are both H or both F;

and M is a radionuclide selected from any one of $^{68}$Ga, $^{177}$Lu, or $^{90}$Y.

5. A method for preparing a radiolabeled complex of truncated Evans Blue modified Fibroblast activation protein inhibitor, comprising the following steps: dissolving the compound shown in Formula (II-1) according to claim 1 in a buffer solution or deionized water; and adding a radionuclide solution to the obtained solution for a reaction under closed conditions for 5-40 min to produce a radionuclide labeled complex, or, comprising the following steps: dissolving the compound shown in Formula (II-1) according to claim 1 in a buffer solution or deionized water; treating the obtained solution by aseptic filtration, followed by loading into a container, freeze-drying and sealing with a stopper to obtain a freeze-dried medicine box; and then adding an appropriate amount of an acetic acid solution or a buffer solution to the freeze-dried medicine box for dissolution, and adding a corresponding radionuclide solution for a reaction under closed conditions for 5-40 min to produce a radionuclide labeled complex.

6. A method for nuclide therapy or imaging of tumors with high expression of FAP, comprising: radiolabeling the compound according to claim 1 or a pharmacologically acceptable salt thereof; and administering the radiolabeled compound or a pharmacologically acceptable salt thereof to a subject that is to receive nuclide therapy or imaging of tumors.

7. A method for a nuclide therapy or an imaging of tumors with high expression of FAP, comprising administrating the complex according to claim 4 or a pharmacologically acceptable salt thereof to a subject receiving the nuclide therapy or the imaging of tumors.

8. The method according to claim 6, wherein the compound or the pharmacologically acceptable salt thereof is formulated as an injection and then intravenously injected into patients with tumors with high expression of FAP.

* * * * *